US008258286B2

(12) United States Patent
Davidson et al.

(10) Patent No.: US 8,258,286 B2
(45) Date of Patent: Sep. 4, 2012

(54) REDUCTION OF OFF-TARGET RNA INTERFERENCE TOXICITY

(75) Inventors: Beverly L. Davidson, North Liberty, IA (US); Alejandro Mas Monteys, Iowa City, IA (US); Jodi L. McBride, Iowa City, IA (US); Ryan Boudreau, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 244 days.

(21) Appl. No.: 12/129,523

(22) Filed: May 29, 2008

(65) Prior Publication Data

US 2009/0130751 A1    May 21, 2009

Related U.S. Application Data

(63) Continuation-in-part of application No. 12/111,025, filed on Apr. 28, 2008, now abandoned.

(60) Provisional application No. 60/914,309, filed on Apr. 26, 2007, provisional application No. 60/932,468, filed on May 31, 2007, provisional application No. 61/038,685, filed on Mar. 21, 2008, provisional application No. 61/070,622, filed on Mar. 25, 2008.

(51) Int. Cl.
*C07H 21/04* (2006.01)
*C07H 21/02* (2006.01)
*C12N 15/63* (2006.01)

(52) U.S. Cl. ............... 536/24.5; 536/23.1; 435/320.1

(58) Field of Classification Search .................. None
See application file for complete search history.

(56) References Cited

U.S. PATENT DOCUMENTS

| | | | |
|---|---|---|---|
| 4,962,091 | A | 10/1990 | Eppstein |
| 5,139,941 | A | 8/1992 | Muzyczka et al. |
| 5,173,414 | A | 12/1992 | Lebkowski et al. |
| 5,350,674 | A | 9/1994 | Boenisch et al. |
| 5,585,362 | A | 12/1996 | Wilson et al. |
| 5,720,720 | A | 2/1998 | Laske et al. |
| 7,232,806 | B2 | 6/2007 | Tusch et al. |
| 7,902,352 | B2 | 3/2011 | Kaemmerer et al. |
| 2002/0114780 | A1 | 8/2002 | Bankiewicz et al. |
| 2002/0141980 | A1 | 10/2002 | Bankiewicz et al. |
| 2002/0187127 | A1 | 12/2002 | Bankiewicz et al. |
| 2004/0162255 | A1 | 8/2004 | Kaemmerer |
| 2006/0130176 | A1* | 6/2006 | Reyes-Taboada et al. .... 800/279 |
| 2006/0257912 | A1 | 11/2006 | Kaemmerer et al. |
| 2010/0008981 | A1 | 1/2010 | Kaemmerer et al. |
| 2010/0325746 | A9 | 12/2010 | Kaemmerer et al. |

FOREIGN PATENT DOCUMENTS

| | | |
|---|---|---|
| WO | WO 94/07529 | 4/1994 |
| WO | WO 94/07529 A2 | 4/1994 |
| WO | WO 2004/047872 | 6/2004 |
| WO | WO 2005/105995 | 11/2005 |
| WO | WO 2006/083800 | 8/2006 |
| WO | WO 2007/022506 A2 | 2/2007 |
| WO | WO 2007/089584 A2 | 8/2007 |
| WO | WO 2008/134646 A2 | 11/2008 |
| WO | WO 2008/134646 A3 | 11/2008 |

OTHER PUBLICATIONS

Harper et al., "RNA interference improves motor and neuropathological abnormalities in a Huntington's disease mouse model" PNAS, vol. 102, 5820-5825 (2005).
Han J et al., "Molecular basis for the recognition of primary microRNAs by the Drosha-DGCR8 Complex" Cell. vol. 125, 887-901 (2006).
International Search Report and Written Opinion of the International Searching Authority, May 4, 2009.
Boden, "Enhanced gene silencing of HIV-1 specific siRNA using microRNA designed hairpins," Nucleic Acids Res, 32, 1154-1158, (2004).
Denovan-Wright, "RNAi: a potential therapy for the dominantly inherited nucleotide repeat diseases", *Gene Therapy*, 13, 525-531, (2006).
De Paula, "Hydrophobization and bioconjugation for enhanced siRNA delivery and targeting", RNA, 13, 431-456, (2007).
Grimm, "Fatality in mice due to oversaturation of cellular microRNA/short hairpin RNA pathways," Nature, 441, 537-541, (2006).
Khvorova, "Functional siRNAs and miRNAs Exhibit strand Bias", Cell, 115, 209-216 (1 supplementary page), (2003).
Landgraf, "A Mammalian microRNA Expression Atlas Based on Small RNA Library Sequencing", *Cell*, 129, 1401-1414, (2007).
Li, "Defining the optimal parameters for hairpin-based knockdown constructs," RNA, 13, 1765-1774, (2007).
McMahon, "Optimisation of electrotransfer of plasmid into skeletal muscle by pretreatment with hyaluronidase—increased expression with reduced muscle damage " Gene Therapy 8, 1264-1270 (2001).
Miyagishi, "Optimization of an siRNA-expression system with an improved hairpin and its significant suppressive effects in mammalian cells", *J. Gene Med.*, 6, 714-723, (2004).
Silva, "Second-generation shRNA libraries covering the mouse and human genomes", Nature Genetics, 37, 1281-1288 (13 supplementary pages), (2005).
Stegmeier, "A lentiviral microRNA-based system for single-compy polymerase II-regulated RNA interference in mammalian cells", *PNAS*, 102, 13212-13219 (3 supplementary pages), (2005).
Vermeulen, "The contributions of dsRNA structure to Dicer specificity and efficiency," RNA, 11, 674-682, (2005).
Xia, "RNAi suppresses polyglutamine-induced neurodegeneration in a model of spinocerebellar ataxia", Nature Medicine, 10, 816-820 (4 supplementary pages), (2004).
Liu et al., "Specific inhibition of Huntington's disease gene expression by siRNAs in cultured cells", *Proc.Japan Acad.*, 79, *Ser. B*, No. 10, pp. 293-298, 2003.
McBride et al., "Artificial miRNAs mitigate shRNA-mediated toxicity in the brain: Implications for the therapeutic development of RNAi", *PNAS*, vol. 105, No. 15, pp. 5868-5873, 2008.
Rodriguez-Lebron, et al., "Intrastriatal rAAV-Mediated Delivery of Anti-huntingtin shRNAs Induces Partial Reversal of Disease Progression in R6/1 Huntington's Disease Transgenic Mice", *Molecular Therapy* vol. 12, No. 4, pp. 618-633, 2005.
Wang et al., "Clinico-pathological rescue of a model mouse of Huntington's disease by siRNA", *Neuroscience Research* 53, pp. 241-249, 2005.

* cited by examiner

*Primary Examiner* — Amy Bowman

(74) *Attorney, Agent, or Firm* — Viksnins Harris & Padys PLLP

(57) ABSTRACT

The present invention is directed to RNA interference (RNAi) molecules targeted against a nucleic acid sequence, and methods of using these RNAi molecules to reduce off-target toxicity.

38 Claims, 53 Drawing Sheets

Fig. 1
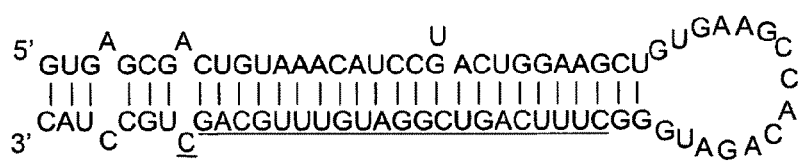
mir-30
SEQ ID NO:1
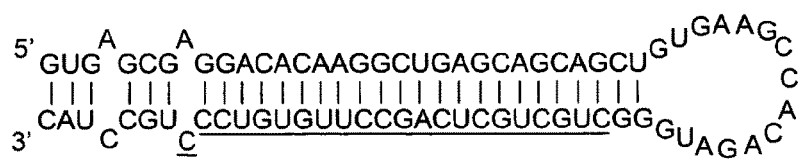
miSCA1
SEQ ID NO:2
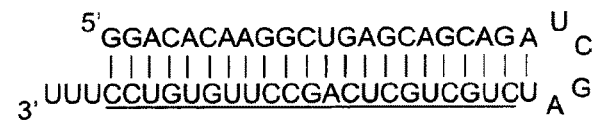
shSCA1
SEQ ID NO:3
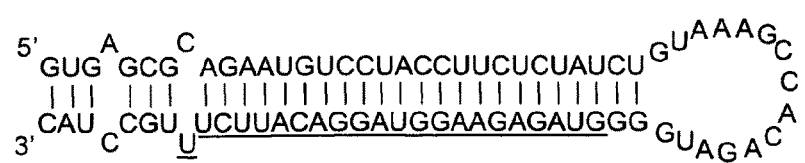
miJNK
SEQ ID NO:4
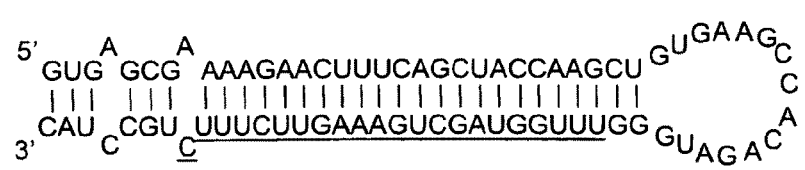
miHTT
SEQ ID NO:5

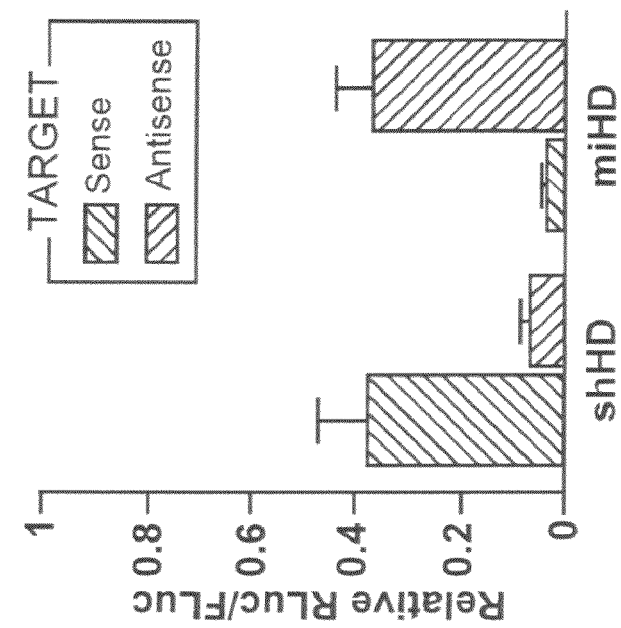
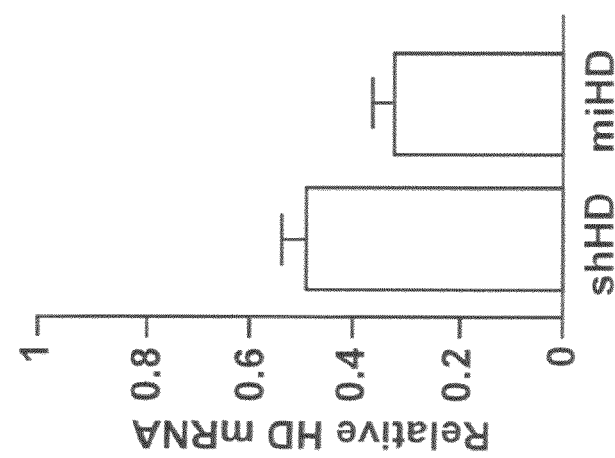
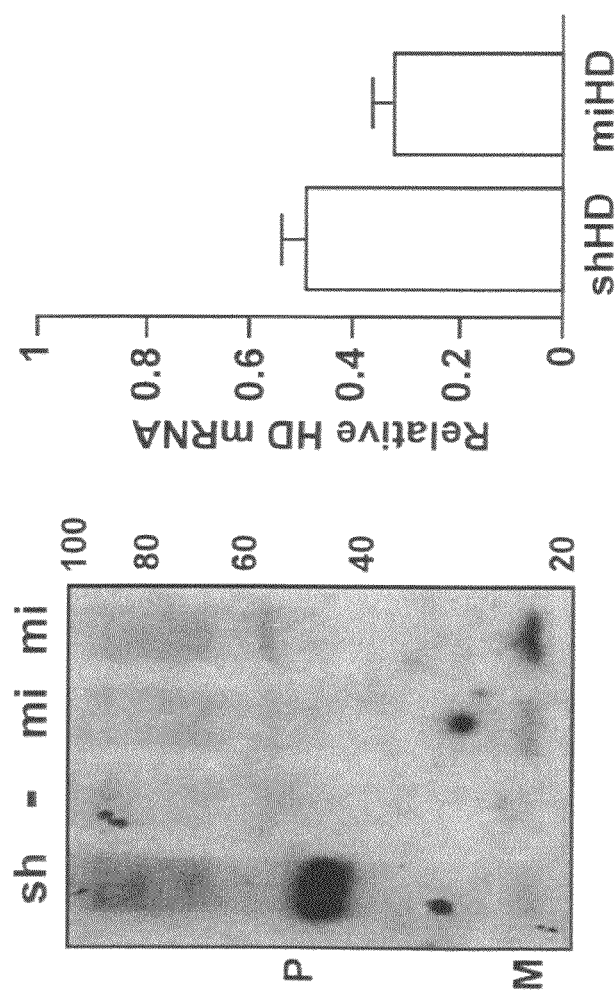

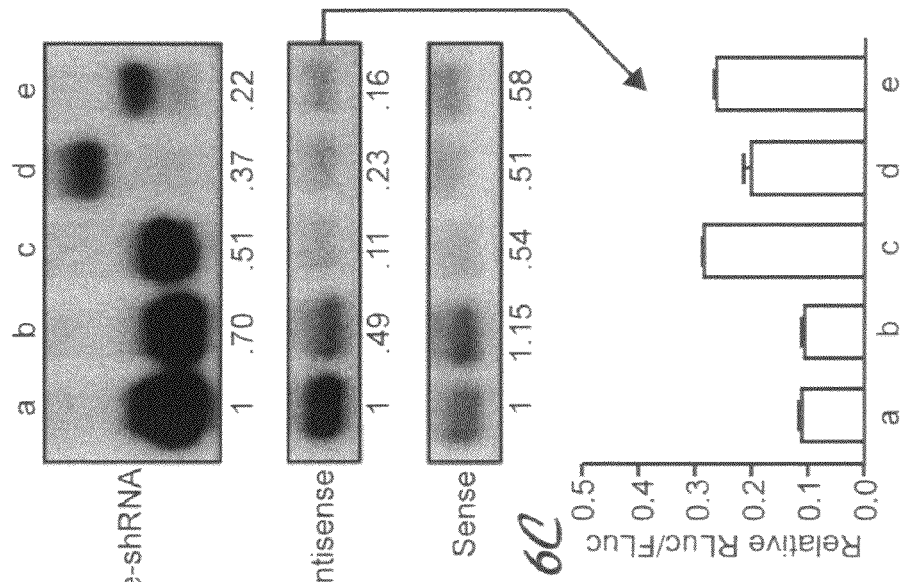
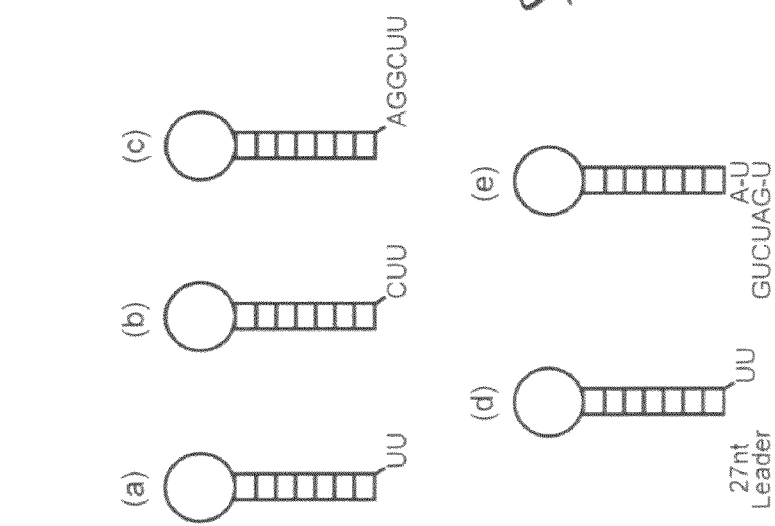
Fig. 6A  Fig. 6B  Fig. 6C

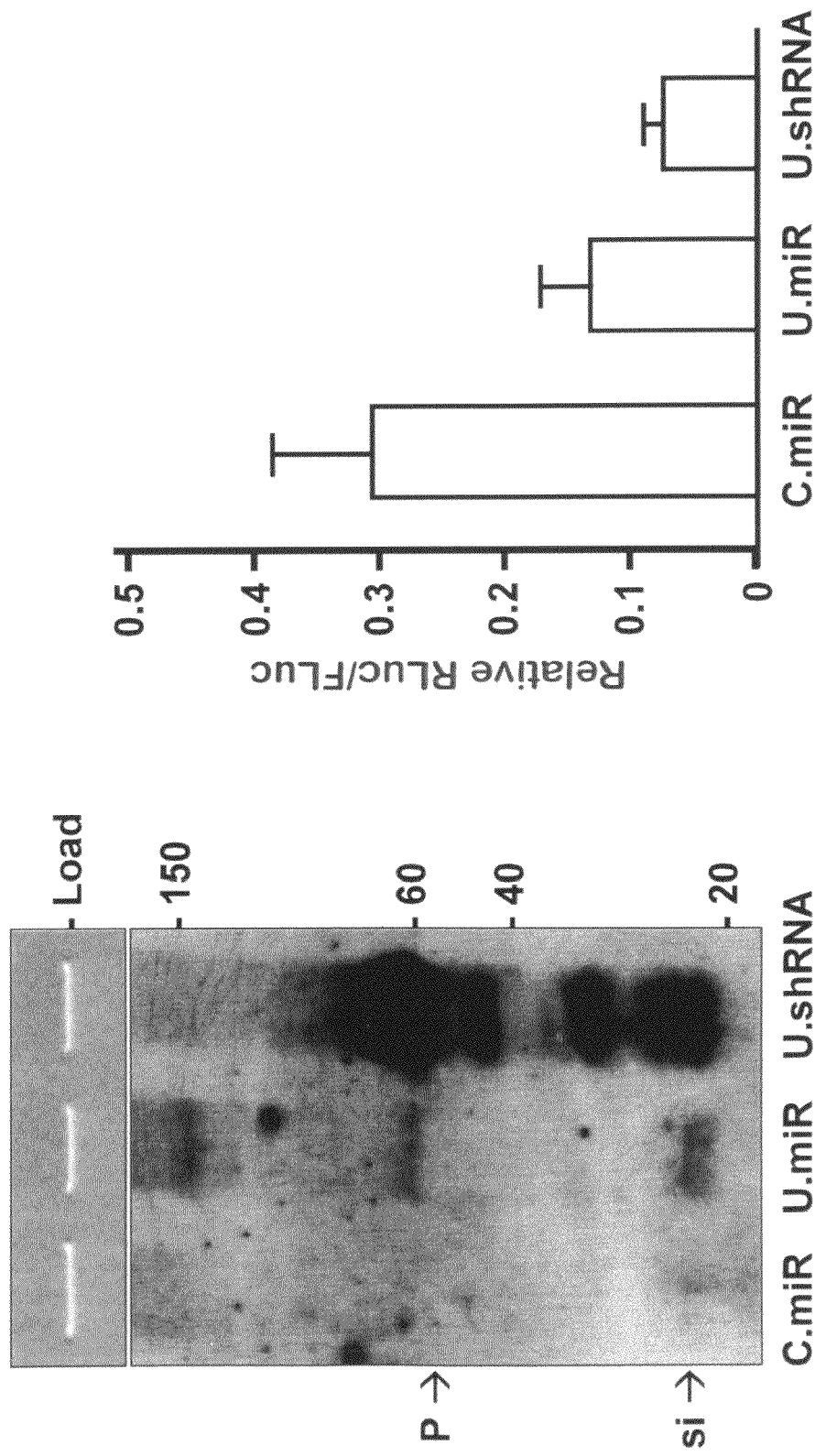

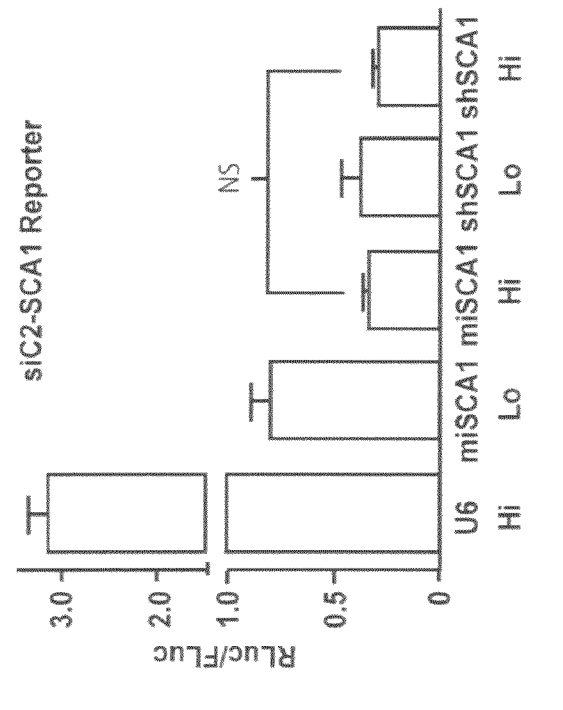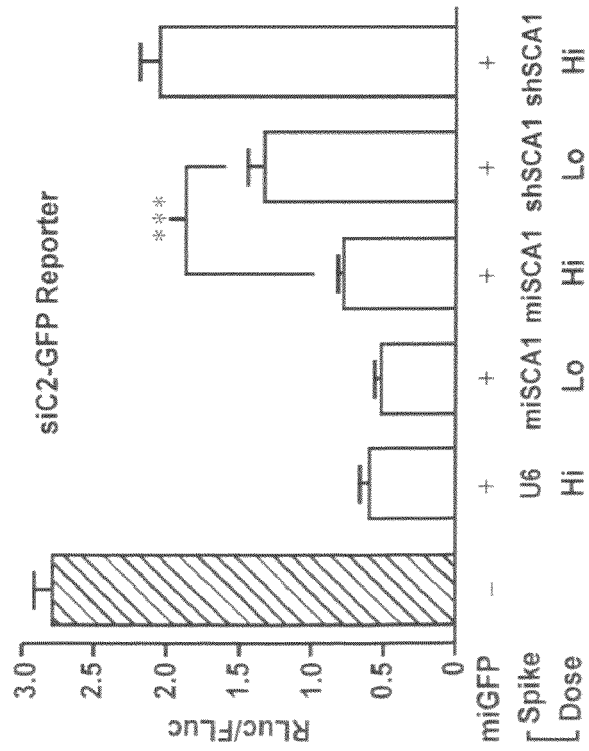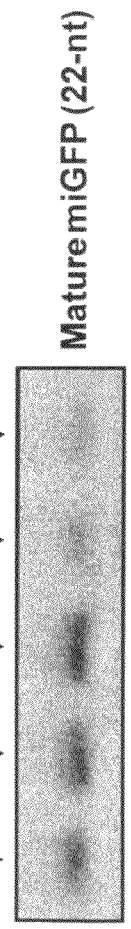

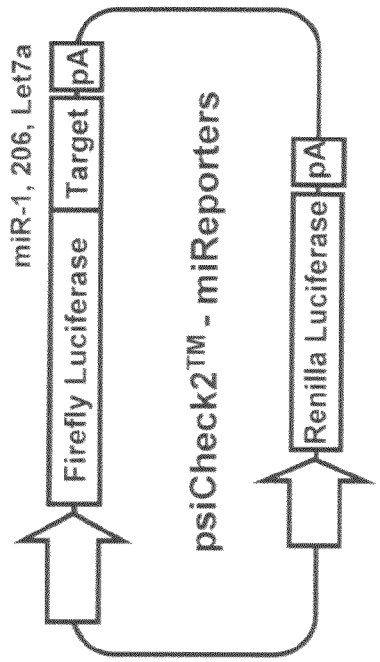
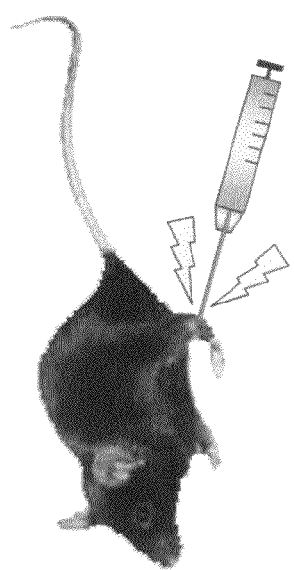
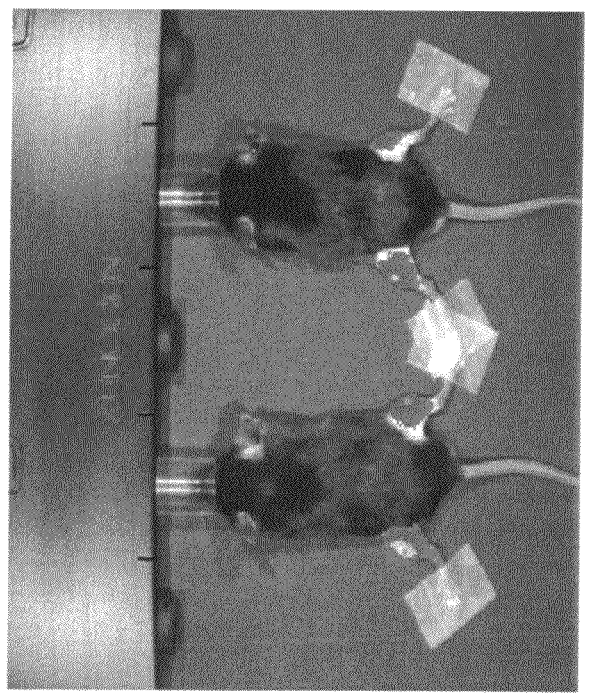
Fig. 11

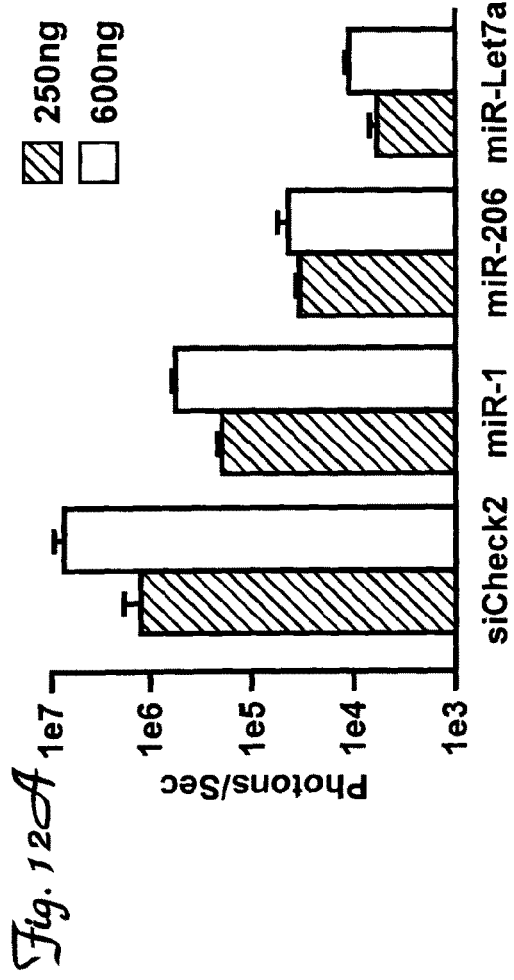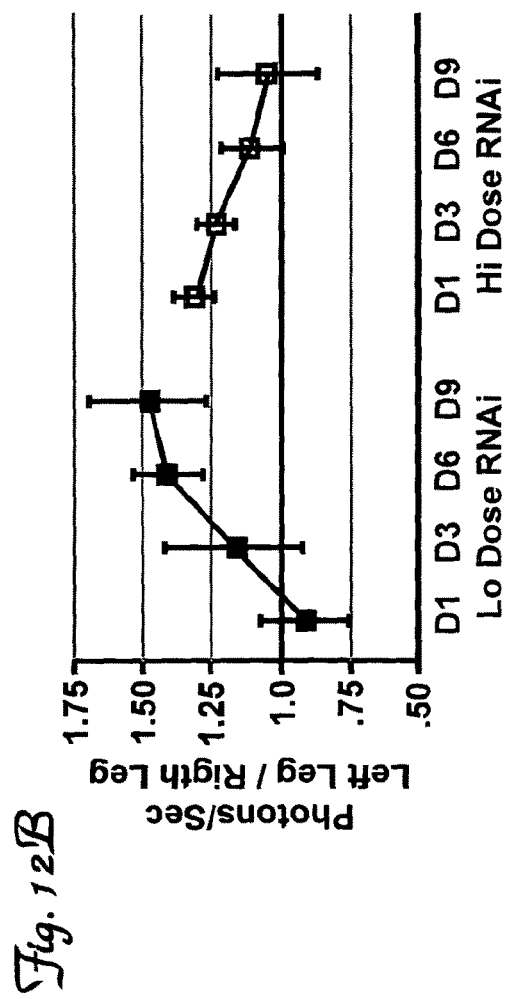
Fig. 12A
Fig. 12B mU6 Promotor

```
                    +1
...CCCTTGGAGAAAAGCCTTGTTTG          SEQ ID NO:7
``` miRNA Flanking Sequences

Variant 1
```
U6+1          CMV+1           XhoI          SpeI
...GCGTTTAGTGAACCGTTCAGATGGTACCGTTTAAAA-CTCGAG-miRNA-ACTAGT-TCTAGAGGCGGCCGCCACAGCGGGGAGATCCAGACA...
SEQ ID NO:8                                                                    SEQ ID NO:223
```

Variant 2
```
U6+1          CMV+1           XhoI          SpeI/XbaI
...GCGTTTAGTGAACCGTCAGATGGTACCGTTTAAAA-CTCGAG-miRNA-CTAGA-GCGGCCGCCACAGCGGGGAGATCCAGACATGATGA...
SEQ ID NO:9                                                                    SEQ ID NO:224
```

Variant 3
```
U6+1          CMV+1           XhoI          SpeI/XbaI
...GCGTTTAGTGAACCGTCAGATGGTACCGTTTAAAA-CTCGAG-miRNA-ACTAGA-ACATAATCAGCCATACCACATTTGTAGAGGTTTTA...
SEQ ID NO:10                                                                   SEQ ID NO:225
```

Basic miRNA Structure

```
              ↓
         A  N   GUAAAG
5'...XhoI-UG GCG NNNNNNNNNNNNNNCU   C
3'....SpeI-U CGC NNNNNNNNNNNNNNGG   C
         C  N   GUAGACA
             ↑
```
SEQ ID NO:11 miHD (2.1)

```
         A  A   GUGAAG
5'...XhoI-UG GCG AAAGAACUUUCAGCUACCAAGCU   C       SEQ ID NO:12
3'....SpeI-U CGU UUUCUUGAAAGUCGAUGGUUUGG   C
         C  C   GUAGACA
```

Oligo 1: aaaactcgagtgagcgaaaagaacttttcagctaccaagctgtgaagccacagatggg   SEQ ID NO:13

Oligo 2: aaaaactagtcaggcagaaaagaacttttcagctaccaaccatctgtggctttacag    SEQ ID NO:14 shHD (2.1)

```
            GAA
5'    AAGAAGAACUUUCAGCUACC   G   SEQ ID NO:15
3'    UUCUUUCUUGAAAGUCGAUGG   C
            GUU
```

Oligo: 5' ctcgagaaaaagaaaagaacttttcagctaccaagcttcggtagctgaaagtttcttttaaacaacggctttttctccagg 3'
SEQ ID NO:16 miHD (2.1b)

```
       A   C                                 GUAAAG
5'...XhoI-UG GCG AGAAAGAACUUUCAGCUACCGCU          C    SEQ ID NO:17
3'....SpeI-U CGU UCUUUCUUGAAAGUCGAUGGUG           C
       C   U                                 GUAGACA
```

Oligo 1: aaaactcgagtgagcgagaaagaacttcagctaccgctgtaaagccacagatggg  SEQ ID NO:18

Oligo 2: aaaaactagtaggcaaagaaacttcagctaccaccccatctgtggcttttacag  SEQ ID NO:19 shHD (2.1b)

```
       5' GAAAGAACUUUCAGCUACCGCU      C  SEQ ID NO:20
       3' UUCUUUCUUGAAAGUCGAUGGUG     C
                                 GUAGACA
```

Oligo: 5' ttttagatctaaaaaagaaacttcagctaccaccccatctgtggctttacagcggtagctgaaagttctttcaaacaaggcttt
tctccaaggg 3'  SEQ ID NO:21 miSCA1

```
       A   C                                 GUAAAG
5'...XhoI-UG GCG AGCCCAGGUCAGCGUUGAAGUCU          C    SEQ ID NO:22
3'....SpeI-U CGC UCGGGUCCAGUCGCAACUUCAGG          C
       C   U                                 GUAGACA
```

Oligo 1: aaaactcgagtgagcgagcccaggtcagcgttgaagtctgtaaagccacagatggg  SEQ ID NO:23

Oligo 2: aaaaactagtaggcgaagccaggtcagcgttgaagtcccatctgtggcttttacag  SEQ ID NO:24

*Fig. 16-2A*

Fig. 16-2B shSCA1

```
            GUAAAG
5' GCCCAGGUCAGCGUUGAAGUCU       C    SEQ ID NO:25
3' UUCGGGUCCAGUCGCAACUUCAGG     C
            GUAGACA
```

Oligo: tttagatctaaaaagcccaggtcagcgttgaagtctgaagtcccatctgtgctttacagacttcaacgctgacct
gggcaaacaaggcttttctccaaggg SEQ ID NO:26 mi1913

```
         A   C
5'...XhoI-UG GCG AGCCCAGGUCAGCGUUGAAGUCU    C    SEQ ID NO:27
3'...SpeI-U  CGC UCGGGUCCAGUCGCAACUUCAGG    C
         C   U
                                            GUAGACA
```

Oligo 1: aaaactcgagtgagcgcagcccaggtcagcgttgaagtctgtgaagtctgtaaagccacagatggg SEQ ID NO:28

Oligo 2: aaaaactagtaggcgaagcccaggtcagcgttgaagt SEQ ID NO:29 sh1913

```
            GUAAAG
5' GCCCAGGUCAGCGUUGAAGUCU       C    SEQ ID NO:30
3' UUCGGGUCCAGUCGCAACUUCAGG     C
            GUAGACA
```

Oligo: 5' ttttagatctaaaaagcccaggtcagcgttgaagtcccatctgtggctttacagacttcaacgctgacctgggcaaacaaggcttt
tctccaaggg 3' SEQ ID NO:31

Fig. 16-3A miGFP

```
5'...XhoI-UG GCG AGCACAAGCUGGAGUACAAUUCU      C
                A  C                          GUAAAG
3'....SpeI-U CGC UCGUGUUCGACCUCAUGUUGAGG      C
                C  U                          GUAGACA
```
SEQ ID NO:32

Oligo 1: aaaactcgagtgacgcagcacaagctggagtacaattctgtaaagccacagatggg SEQ ID NO:33
Oligo 2: aaaaactagtaggcaagcacaagctggagtacaactcccatctgtggctttacag SEQ ID NO:34 shGFP

```
5' GCACAAGCUGGAGUACAAUUCU      C
        A  C                   GUAAAG
3' UUCGUGUUCGACCUCAUGUUGAGG    C
        C  U                   GUAGACA
```
SEQ ID NO:35

Oligo: 5' ttttagatctaaaaaagcacaagctggagtacactcccatctgtggcttttacagaattgtactccagcttgtgcaaacaaggcttt
tctccaaggg 3' SEQ ID NO:36 mi1913-miR30 Variant

```
5'...XhoI-UA AUUGCUCUUGA---c----AGUG GCG AGCACAAGCUGGAGUACAAUUCU      C
                U                  A  C                               GUAAAG
3'....SpeI-U-UAACGAGGAUU        UCAU CGC UCGUGUUCGACCUCAUGUUGAGG      C
                UUCAU              C  U                               GUAGACA
                C-G
                G-C
                G-C
                G-C
                G-C
                G-C
               A   G
               A   A
                C C
                UUUC
```
SEQ ID NO:37

Oligo 1: aaaactcgagtatattgtcttgacagtgagcgcagccagtcagcgttgaagtctgtaaagccacagatggg SEQ ID NO:38

Oligo 2: aaaaactagtaattgctcctaaagtagccccttgaagtccgggcagtagcgaagccagtcagcgttgaagtccatctgtggctttacag SEQ ID NO:39 siCheck2™ RNAi Luciferase Reporter Oligos

Renilla forward: aagcccgacgtcgtccag SEQ ID NO:40

RNAi target reverse primers below.

SCA1-Sense (intended): ttttctcgagcaaaacttcaacgctgacctgggcgcgatcgcctagaattactgctcg SEQ ID NO:41

SCA1-AS (unintended): ttttctcgagccagtcagcgttgaagttttctgcgatcgcctagaattactgctcg SEQ ID NO:42

HD2.1-Sense (intended): ttttctcgagtctcttgtagctgaagttcttctcttttgcgatcgcctagaattactgctcg SEQ ID NO:43

HD2.1-AS (unintended): ttttctcgagaagaaaagaactttcagctaccaagaagcgatcgcctagaattactgctcg SEQ ID NO:44

HD-Sense (intended): ttttctcgagacacaatgattcacacgtcttgcatcgcctagaattactgctcg SEQ ID NO:45

HD-AS (unintended): ttttctcgagaccgtgtgaatcattgtttctgcgatcgcctagaattactgctcg SEQ ID NO:46 siCheck2™ RNAi Luciferase Reporter Oligos Cont'd

GFP-Sense (intended): ttttctcgagggcacaagctggtagttgtactccagcttgtgccccgatcgcctagaattactgctcg SEQ ID NO:47

GFP-AS (unintended): ttttctcgagggtagttgtactccagcttgtgccctactgcaactactgccgatcgcctagaattactgctcg SEQ ID NO:48

Fig. 16-3B

Fig. 16-4A miHD2.4

```
                A   C   GUAAAG
5'...XhoI-UG GCG GACCGUGUGAAUCAUUGUUUACU        C
3'....SpeI-U CGC CUGGCACUUAGUAACAGAUGG          C
                C   A                    GUAGACA
```
SEQ ID NO:49 miHD2.4.2

```
                A   C   GUAAAG
5'...XhoI-UG GCG ACCGUGUGAAUCAUUGUCUAACU        C
3'....SpeI-U CGC UGGCACUUAGUAACAGAUUGG          C
                C   A                    GUAGACA
```
SEQ ID NO:50 miHD8.2

```
                A   C   GUAAAG
5'...XhoI-UG GCG AGCAGCUUGUCCAGGUUUAUGCU        C
3'....SpeI-U CGC UCGUCGAACAGGUCCAAAUAUGG        C
                C   A                    GUAGACA
```
SEQ ID NO:51 miHD8.2.2

```
                A   C   GUAAAG
5'...XhoI-UG GCG AGAGCAGCUUGUCCAGGUUUACU        C
3'....SpeI-U CGC UCUCGUCGAACAGGUCCAAAUGG        C
                C   A                    GUAGACA
```
SEQ ID NO:52 miHD8.2.3

```
              A     A                      GUAAAG
5'...XhoI-UG GCG AGAGCAGCUUGUCCAGGUUUACU         C
3'....SpeI-U CGC UCUCGUCGAACAGGUCCAAAUGG         C
              C     C                      GUAGACA
                                                    SEQ ID NO:53
``` miSCA1-2225

```
              A     C                      GUAAAG
5'...XhoI-UG GCG GGGGAACUGAAGUUCCAGAACU          C
3'....SpeI-U CGC CCGCUUGACUUCAAGGUCUUGG          C
              C     A                      GUAGACA
                                                    SEQ ID NO:54
``` miSCA1-1399

```
              A     C                      GUAAAG
5'...XhoI-UG GCG CGGCCAGCAGCAAGCAAUCAUCC         C
3'....SpeI-U CGC GCCGGUCGUCGUUCGUUAGUGGG         C
              C     A                      GUAGACA
                                                    SEQ ID NO:55
``` shHD2.1 mRNA target site:

5' AAG AAA GAA CTT TCA GCT ACC 3'     SEQ ID NO:56

*Fig. 16-4B*

2.1 hairpin

Sense strand     HindIII loop     Antisense Strand
5' AAG AAA GAA CTT TCA GCT ACC (GAAGCTTG) GGT AGC TGA AAG TTC TTT CTT 3'     SEQ ID NO:57

Sense strand     HindIII loop     Antisense Strand
5' G AAG AAA GAA CTT TCA GCT ACC (GAAGCTTG) GGT AGC TGA AAG TCC TTT CTT 3'     SEQ ID NO:58

Sense strand     microRNA loop     Antisense Strand
5' AAG AAA GAA CTT TCA GCT ACC (CTTCCTGTCA) GGT AGC TGA AAG TTC TTT CTT 3'     SEQ ID NO:59

Sense strand     microRNA loop     Antisense Strand
5' G AAG AAA GAA CTT TCA GCT ACC (CTTCCTGTCA) GGT AGC TGA AAG TTC TTT CTT 3'     SEQ ID NO:60

Sense strand     microRNA loop     Antisense Strand
5' AAG AAA GAA CTT TCA GCT ATT A (CTTCCTGTCA) T GGT AGC TGA AAG TTC TTT CTT 3'     SEQ ID NO:61

Sense strand     microRNA loop     Antisense Strand
5' G AAG AAA GAA CTT TCA GCT ATT A (CTTCCTGTCA) T GGT AGC TGA AAG TTC TTT CTT 3'     SEQ ID NO:62

Sense strand     Hind III loop     Antisense Strand
5' AAG AAA GAA CTT TCA GCT ATT A (GAAGCTTG) T GGT AGC TGA AAG TTC TTT CTT 3'     SEQ ID NO:63

Sense strand     Hind III loop     Antisense Strand
5' G AAG AAA GAA CTT TCA GCT ATT A (GAAGCTTG) T GGT AGC TGA AAG TTC TTT CTT 3'     SEQ ID NO:64

*Fig. 16-5A* shHD2.4

5' GAC CGT GTG AAT CAT TGT CTA 3'    SEQ ID NO:65 shHD2HD2.4 hairpin

Sense strand                microRNA loop      Antisense Strand
5' GAC CGT GTG AAT CAT TGT CTA (CTTCCTGTCA) TAG ACA ATG ATT CAC ACG GTC 3'    SEQ ID NO:66 shHD8.2 mRNA target site:

5' CAG CTT GTC CAG GTT TAT GAA 3'    SEQ ID NO:67

Sense strand                microRNA loop      Antisense Strand
5' CAG CTT GTC CAG GTT TAT GAA (CTTCCTGTCA) TTC ATA AAC CTG GAC AAG CTG 3'    SEQ ID NO:68 shHD30.1 mRNA Target Site:

5' GGA TAC CTG AAA TCC TGC TTT 3'    SEQ ID NO:69

Sense strand                microRNA loop      Antisense Strand
5' GGA TAC CTG AAA TCC TGC TTT (CTTCCTGTCA) AAA GCA GGA TTT CAG GTA TCC 3'    SEQ ID NO:70

*Fig. 16-5B*

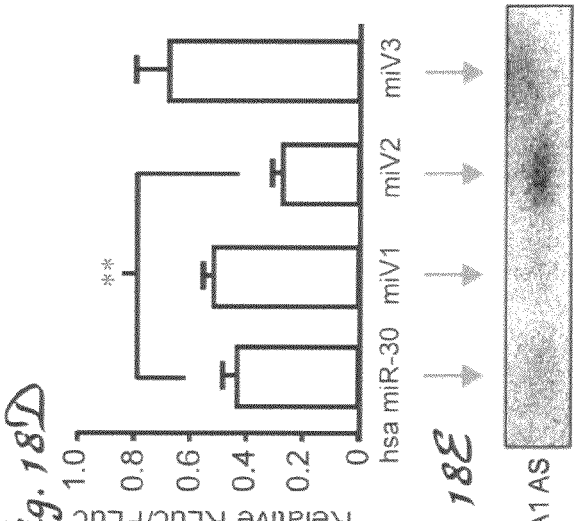

Fig. 19

```
miHD2.4
             A   C                         GUAAAG
5'...XhoI-UG GCG GACCGUGUGAAUCAUUGUUUACU          C    SEQ ID NO:75
3'....SpeI-U CGC CUGGCACACUUAGUAACAGAUGG          C
             C   A                         GUAGACA miHD2.4.2
             A   C                         GUAAAG
5'...XhoI-UG GCG ACCGUGUGAAUCAUUGUCUAACU          C    SEQ ID NO:76
3'....SpeI-U CGC UGGCACACUUAGUAACAGAUUGG          C
             C   A                         GUAGACA miHD8.2
             A   C                         GUAAAG
5'...XhoI-UG GCG AGCAGCUUGUCCAGGUUUAUGCU          C    SEQ ID NO:77
3'....SpeI-U CGC UCGUCGAACAGGUCCAAAUAUGG          C
             C   A                         GUAGACA miHD8.2.2
             A   C                         GUAAAG
5'...XhoI-UG GCG AGAGCAGCUUGUCCAGGUUUACU          C    SEQ ID NO:78
3'....SpeI-U CGC UCUCGUCGAACAGGUCCAAAUGG          C
             C   A                         GUAGACA miHD8.2.3
             A   A                         GUAAAG
5'...XhoI-UG GCG AGAGCAGCUUGUCCAGGUUUACU          C    SEQ ID NO:79
3'....SpeI-U CGC UCUCGUCGAACAGGUCCAAAUGG          C
             C   C                         GUAGACA miSCA1-2225
             A   C                         GUAAAG
5'...XhoI-UG GCG GGCGAACUGAAGUUUCCAGAACU          C    SEQ ID NO:80
3'....SpeI-U CGC CCGCUUGACUUCAAAGGUCUUGG          C
             C   A                         GUAGACA miSCA1-1399
             A   C                         GUAAAG
5'...XhoI-UG GCG CGGCCAGCAGCAAGCAAUCAUCC          C    SEQ ID NO:81
3'....SpeI-U CGC GCCGGUCGUCGUUCGUUAGUGGG          C
             C   A                         GUAGACA
```

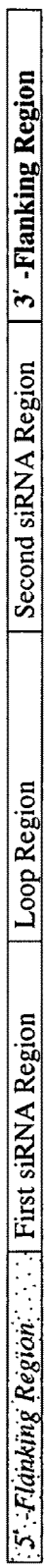
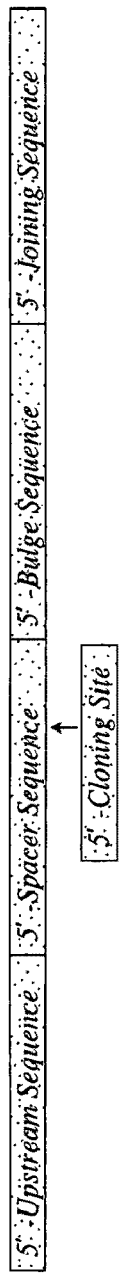
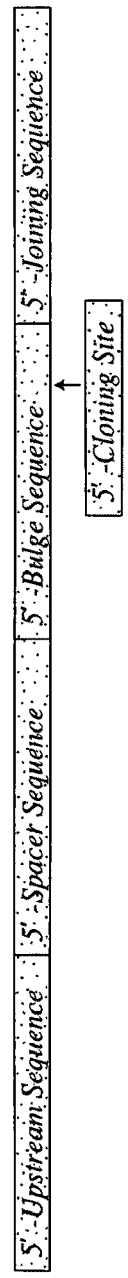
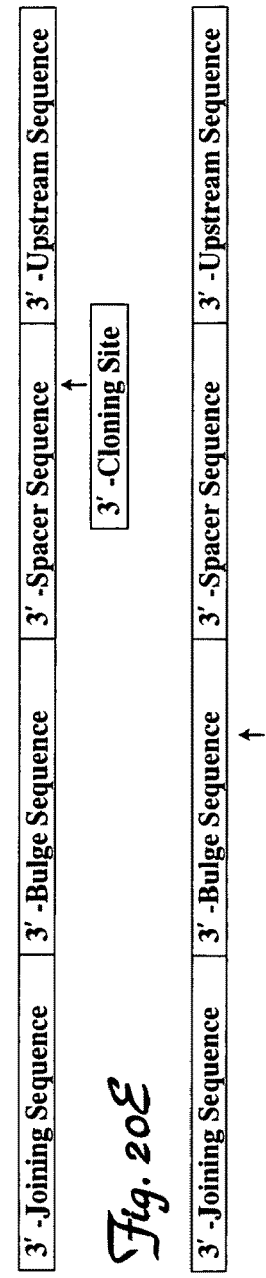

Fig. 20A | 5'-Flanking Region | First siRNA Region | Loop Region | Second siRNA Region | 3'-Flanking Region Fig. 20B | 5'-Upstream Sequence | 5'-Spacer Sequence | 5'-Bulge Sequence | 5'-Joining Sequence
↑ 5'-Cloning Site Fig. 20C | 5'-Upstream Sequence | 5'-Spacer Sequence | 5'-Bulge Sequence | 5'-Joining Sequence
↑ 5'-Cloning Site Fig. 20D | 3'-Joining Sequence | 3'-Bulge Sequence | 3'-Spacer Sequence | 3'-Upstream Sequence
↑ 3'-Cloning Site Fig. 20E | 3'-Joining Sequence | 3'-Bulge Sequence | 3'-Spacer Sequence | 3'-Upstream Sequence
↑ 3'-Cloning Site

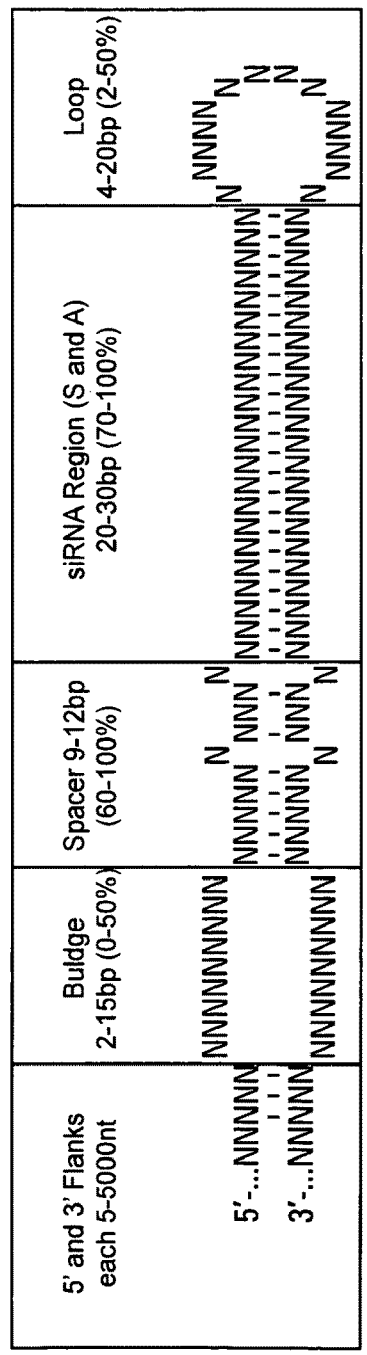

SEQ ID NO:82    SEQ ID NO:83

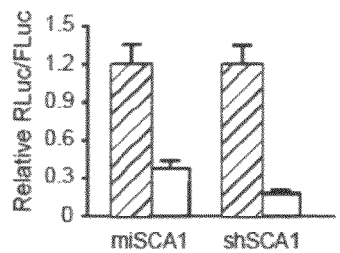
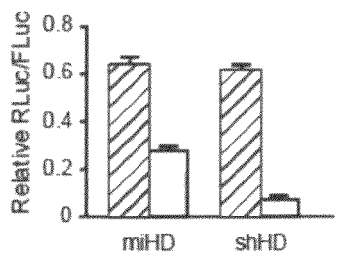
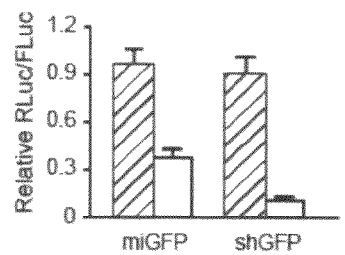
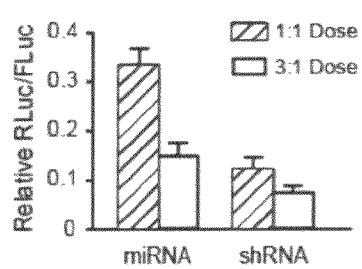
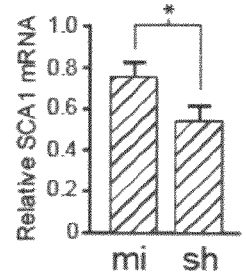
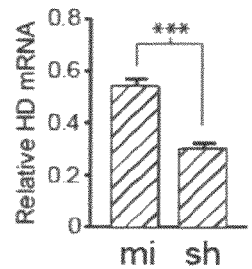
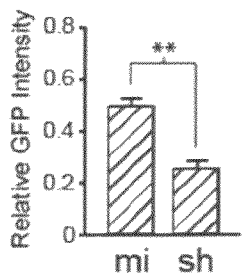
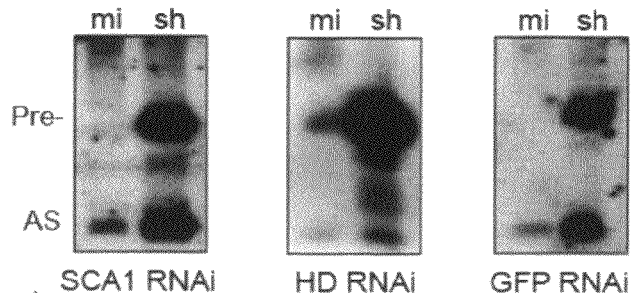

Fig. 27

|  | | | |
|---|---|---|---|
| | Possible shSCA1 AS | 5'-ACUUCAACGCUGACCUGGGCUU-UU... | SEQ ID NO:84 |
| | 3' RACE AS primer | 5'-ACUUCAACGCUGACCU | SEQ ID NO:85 |
| | 3' RACE Seq1 | 5'-ACUUCAACGCUGACCUGGGC | SEQ ID NO:86 |
| | 3' RACE Seq2 | 5'-ACUUCAACGCUGACCUGGGC | SEQ ID NO:87 |
| | 3' RACE Seq3 | 5'-ACUUCAACGCUGACCUGGGC | SEQ ID NO:88 |
| | 3' RACE Seq4 | 5'-ACUUCAACGCUGACCUGGGCU | SEQ ID NO:89 |
| shSCA1 AS | 3' RACE Seq5 | 5'-ACUUCAACGCUGACCUGGGCU | SEQ ID NO:90 |
| | 3' RACE Seq6 | 5'-ACUUCAACGCUGACCUGGGCU | SEQ ID NO:91 |
| | 3' RACE Seq7 | 5'-ACUUCAACGCUGACCUGGGCUU | SEQ ID NO:92 |
| | 3' RACE Seq8 | 5'-ACUUCAACGCUGACCUGGGCUU | SEQ ID NO:93 |
| | 3' RACE Seq9 | 5'-ACUUCAACGCUGACCUGGGCUU | SEQ ID NO:94 |
| | 3' RACE Seq10 | 5'-ACUUCAACGCUGACCUGGGCUU | SEQ ID NO:95 |
| | 3' RACE Seq11 | 5'-ACUUCAACGCUGACCUGGGCUU+u | SEQ ID NO:96 |
| | 3' RACE Seq12 | 5'-ACUUCAACGCUGACCUGGGCUU+u | SEQ ID NO:97 |
| | | | |
| | Possible miSCA1 AS | 5'-ACUUCAACGCUGACCUGGGCUU-UG... | SEQ ID NO:98 |
| | 3' RACE AS primer | 5'-ACUUCAACGCUGACCU | SEQ ID NO:99 |
| | 3' RACE Seq1 | 5'-ACUUCAACGCUGACCUGGGC | SEQ ID NO:100 |
| | 3' RACE Seq2 | 5'-ACUUCAACGCUGACCUGGGC | SEQ ID NO:101 |
| | 3' RACE Seq3 | 5'-ACUUCAACGCUGACCUGGGC | SEQ ID NO:102 |
| | 3' RACE Seq4 | 5'-ACUUCAACGCUGACCUGGGC | SEQ ID NO:103 |
| miSCA1 AS | 3' RACE Seq5 | 5'-ACUUCAACGCUGACCUGGGCU | SEQ ID NO:104 |
| | 3' RACE Seq6 | 5'-ACUUCAACGCUGACCUGGGCU | SEQ ID NO:105 |
| | 3' RACE Seq7 | 5'-ACUUCAACGCUGACCUGGGCUU | SEQ ID NO:106 |
| | 3' RACE Seq8 | 5'-ACUUCAACGCUGACCUGGGCUU | SEQ ID NO:107 |
| | 3' RACE Seq9 | 5'-ACUUCAACGCUGACCUGGGCUU | SEQ ID NO:108 |
| | 3' RACE Seq10 | 5'-ACUUCAACGCUGACCUGGGCUU | SEQ ID NO:109 |
| | 3' RACE Seq11 | 5'-ACUUCAACGCUGACCUGGGCUU | SEQ ID NO:110 |
| | 3' RACE Seq12 | 5'-ACUUCAACGCUGACCUGGGCUU+c | SEQ ID NO:111 |
| | | | |
| | Possible shSCA1 S | 5'-GCCCAGGUCAGCGUUGAAGUC-UG | SEQ ID NO:112 |
| | 3' RACE S primer | 5'-CCAGGUCAGCGUUGA | SEQ ID NO:113 |
| | 3' RACE Seq1 | 5'-GCCCAGGUCAGCGUUGAAGU | SEQ ID NO:114 |
| | 3' RACE Seq2 | 5'-GCCCAGGUCAGCGUUGAAGU | SEQ ID NO:115 |
| | 3' RACE Seq3 | 5'-GCCCAGGUCAGCGUUGAAGUC | SEQ ID NO:116 |
| shSCA1 S | 3' RACE Seq4 | 5'-GCCCAGGUCAGCGUUGAAGUC | SEQ ID NO:117 |
| | 3' RACE Seq5 | 5'-GCCCAGGUCAGCGUUGAAGUC | SEQ ID NO:118 |
| | 3' RACE Seq6 | 5'-GCCCAGGUCAGCGUUGAAGUC | SEQ ID NO:119 |
| | 3' RACE Seq7 | 5'-GCCCAGGUCAGCGUUGAAGUC | SEQ ID NO:120 |
| | 3' RACE Seq8 | 5'-GCCCAGGUCAGCGUUGAAGUC | SEQ ID NO:121 |
| | 3' RACE Seq9 | 5'-GCCCAGGUCAGCGUUGAAGUCU | SEQ ID NO:122 |
| | | | |
| | Possible miSCA1 S | 5'-GCCCAGGUCAGCGUUGAAGUC-UG | SEQ ID NO:123 |
| | 3' RACE S primer | 5'-CCAGGUCAGCGUUGA | SEQ ID NO:124 |
| | 3' RACE Seq1 | 5'-GCCCAGGUCAGCGUUGAAGU | SEQ ID NO:125 |
| | 3' RACE Seq2 | 5'-GCCCAGGUCAGCGUUGAAGU | SEQ ID NO:126 |
| | 3' RACE Seq3 | 5'-GCCCAGGUCAGCGUUGAAGU | SEQ ID NO:127 |
| | 3' RACE Seq4 | 5'-GCCCAGGUCAGCGUUGAAGUC | SEQ ID NO:128 |
| miSCA1 S | 3' RACE Seq5 | 5'-GCCCAGGUCAGCGUUGAAGUC | SEQ ID NO:129 |
| | 3' RACE Seq6 | 5'-GCCCAGGUCAGCGUUGAAGUC | SEQ ID NO:130 |
| | 3' RACE Seq7 | 5'-GCCCAGGUCAGCGUUGAAGUC | SEQ ID NO:131 |
| | 3' RACE Seq8 | 5'-GCCCAGGUCAGCGUUGAAGUC | SEQ ID NO:132 |
| | 3' RACE Seq9 | 5'-GCCCAGGUCAGCGUUGAAGUC | SEQ ID NO:133 |
| | 3' RACE Seq10 | 5'-GCCCAGGUCAGCGUUGAAGUC | SEQ ID NO:134 |
| | 3' RACE Seq11 | 5'-GCCCAGGUCAGCGUUGAAGUCU | SEQ ID NO:135 |

Fig. 28
Step 1: Anneal DNA oligos
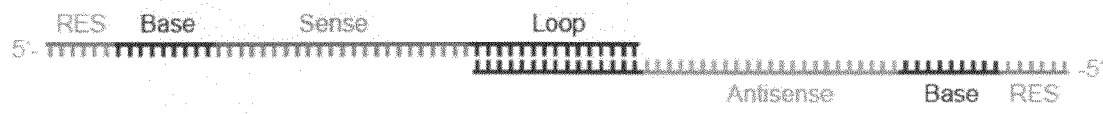
Step 2: Polymerase extension
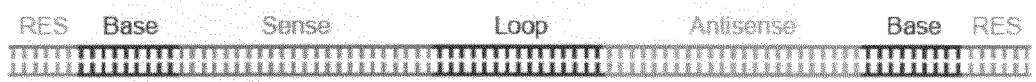
Step 3: Restriction digest & cloning to expression vector
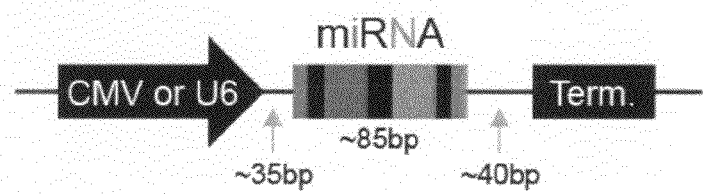
Step 4: Expression of miRNA
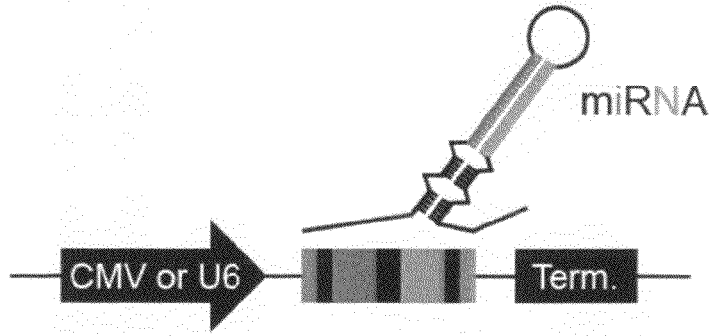

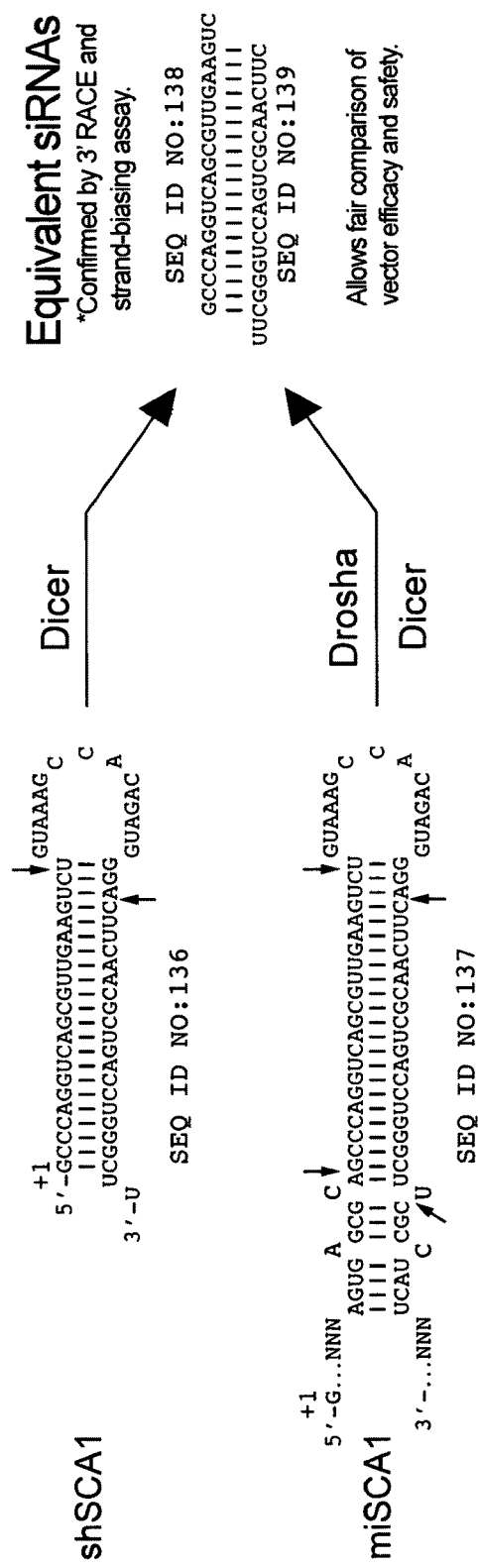

Fig. 34-1 shRNAs targeting human and mouse huntingtin

| shRNA[a] | Sequence | |
|---|---|---|
| sh1.1 | GCGAGUCGGCCCGAGGCCUCCUUCGCUCAGCCGGGCUCCGGA | SEQ ID NO: 140 |
| sh1.4 | AAAAGCUGAUGAAGGCCUUCGUUUUUCGACUACUUCCGGAA | SEQ ID NO: 141 |
| sh1.8 | UGAGGAGCCGCUGCACCGACCUUACUCCUCGGCGACGUGGCU | SEQ ID NO: 142 |
| sh1.9 | GCCGCUGCACCGACCAAAGAAUUCGGCGACGUGGCUGGUUUC | SEQ ID NO: 143 |
| sh1.10 | GCAGCAGCAGCAGCAACAGCCUUCGUCGUCGUCGUCGUUGUC | SEQ ID NO: 144 |
| sh1.11 | AUGGCGACCCUGGAAAAGCUGUUUACCGCUGGGACCUUUUCG | SEQ ID NO: 145 |
| sh1.12 | AAGCUGAUGAAGGCCUUCGAGUUUUCGACUACUUCCGGAAGC | SEQ ID NO: 146 |
| sh1.13 | GCUCAGGUUCUGCUUUUACCUUUCGAGUCCAAGACGAAAAUG | SEQ ID NO: 147 |
| sh2.1[b] | AAGAAAGAACUUUCAGCUACCUUUUCUUUCUUGAAAGUCGAU | SEQ ID NO: 148 |
| sh2.2 | AGAACUUUCAGCUACCAAGAAUUUCUUGAAAGUCGAUGGUUC | SEQ ID NO: 149 |
| sh2.3 | AAGAAAGACCGUGUGAAUCAUUUUUCUUUCUGGCACACUUAG | SEQ ID NO: 150 |
| *sh2.4* | *GACCGUGUGAAUCAUUGUCUAUUCAGGCACACUUAGUAACAG* | *SEQ ID NO: 151* |
| sh2.5 | GUCUGACAAUAUGUGAAAACAUUCAGACUGUUAUACACUUUU | SEQ ID NO: 152 |
| sh2.6 | UGGCACAGUCUGUCAGAAAUUUUACCGUGUCAGACAGUCUUU | SEQ ID NO: 153 |
| sh3.1 | GGGCAUCGCUAUGGAACUGUUUUCCCGUAGCGAUACCUUGAC | SEQ ID NO: 154 |
| sh3.2 | AAUGCCUCAACAAAGUUAUCAUUUUACGGAGUUGUUUCAAUA | SEQ ID NO: 155 |
| sh4.1 | AGCUUUGAUGGAUUCUAAUCUUUUCGAAACUACCUAAGAUUA | SEQ ID NO: 156 |
| *sh8.2* | *CAGCUUGUCCAGGUUUAUGAAUUGUCGAACAGGUCCAAAUAC* | *SEQ ID NO: 157* |

Fig. 34-2

| shRNA[a] | Sequence | |
|---|---|---|
| sh12.1 | CCUGCCAUGGACCUGAAUGAUUUGGACGGUACCUGGACUUAC | SEQ ID NO: 158 |
| sh17.1 | CAUCUUGAACUACAUCGAUCAUUGUAGAACUUGAUGUAGCUA | SEQ ID NO: 159 |
| sh17.2 | AACUACAUCGAUCAUGGAGACUUUGAUGUAGCUAGUACCUC | SEQ ID NO: 160 |
| sh28.1 | CAAACUGCAUGAUGUCCUGAAUUGUUUGACGUACUACAGGAC | SEQ ID NO: 161 |
| *sh30.1* | *GGAUACCUGAAAUCCUGCUUUUUCCUAUGGACUUUAGGACGA* | *SEQ ID NO: 162* |
| sh32.1 | CGUGCAGAUAAGAAUGCUAUUUUGCACGUCUAUUCUUACGAU | SEQ ID NO: 163 |
| sh34.1 | AAGUGGGCCAGUUCAGGGAAUUUUUCACCCGGUCAAGUCCCU | SEQ ID NO: 164 |
| sh34.2 | GUUCAGGGAAUCAGAGGCAAUUUCAAGUCCCUUAGUCUCCGU | SEQ ID NO: 165 |
| sh35.1 | CAUCAUGGCCAGUGGAAGGAAUUGUAGUACCGGUCACCUUCC | SEQ ID NO: 166 |
| sh37.1 | CAGCAGUGCCACAAGGAGAAUUUGUCGUCACGGUGUUCCUCU | SEQ ID NO: 167 |
| sh38.1 | UGAAGCCCUUGGAGUGUUAAAUUACUUCGGGAACCUCACAAU | SEQ ID NO: 168 |
| sh38.2 | AGCCCUUGGAGUGUUAAAUACUUUCGGGAACCUCACAAUUUA | SEQ ID NO: 169 |
| sh40.1 | CUGGAAUGUUCCGGAGAAUCAUUGACCUUACAAGGCCUCUUA | SEQ ID NO: 170 |
| sh42.1 | UUCUCUUCUGUGAUUAUGUCUUUAAGAGAAGACACUAAUACA | SEQ ID NO: 171 |
| sh58.1 | GACGAGGAAGAGGAGGAGGCCUUCUGCUCCUUCUCCUCCUCC | SEQ ID NO: 172 |
| sh58.2 | AAGAGGAGGAGGCCGACGCCCUUUUCUCCUCCUCCGGCUGCG | SEQ ID NO: 173 |
| sh63.1 | GUCCACCCCUCCAUCAUUUAUUCAGGUGGGGGAGGUAGUAA | SEQ ID NO: 174 |

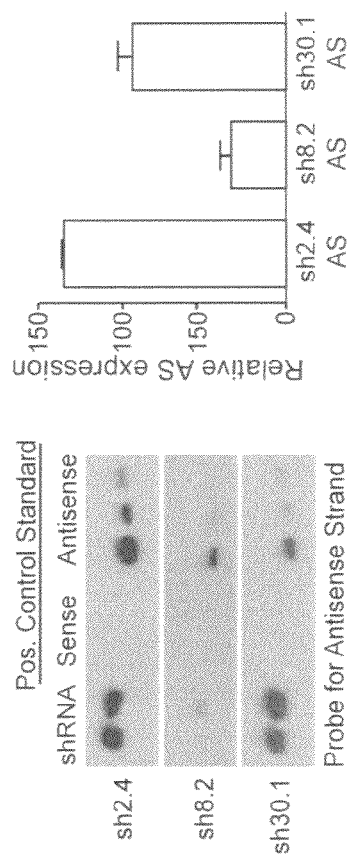
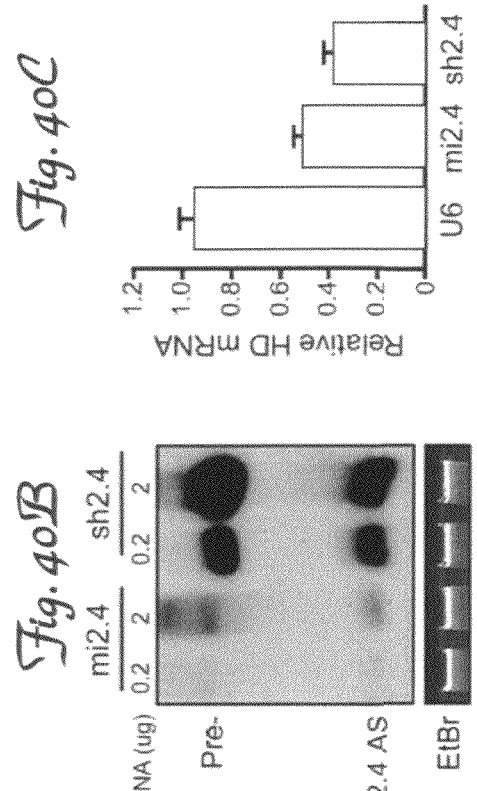
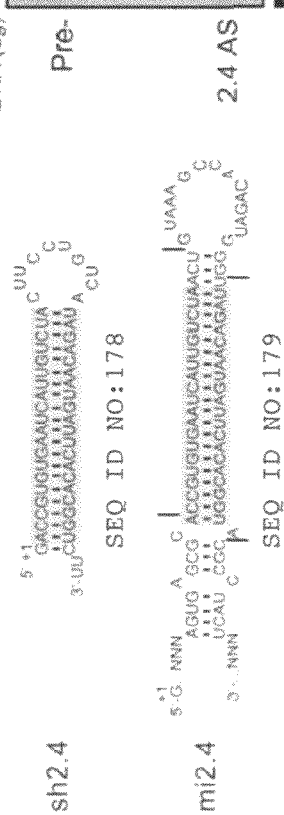

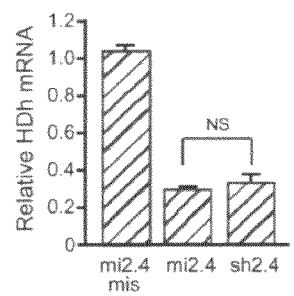
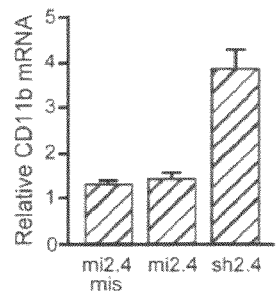
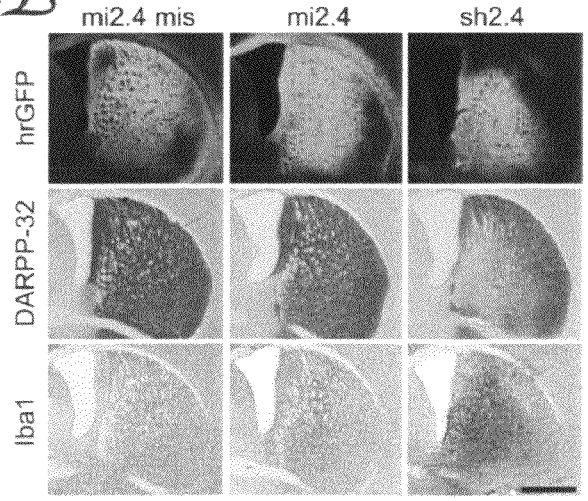

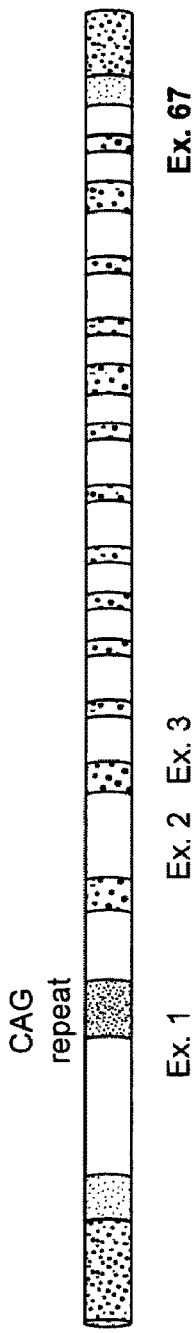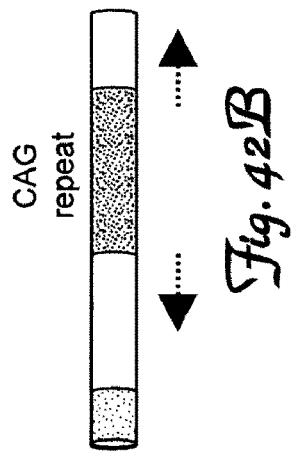
Fig. 42A
Fig. 42B

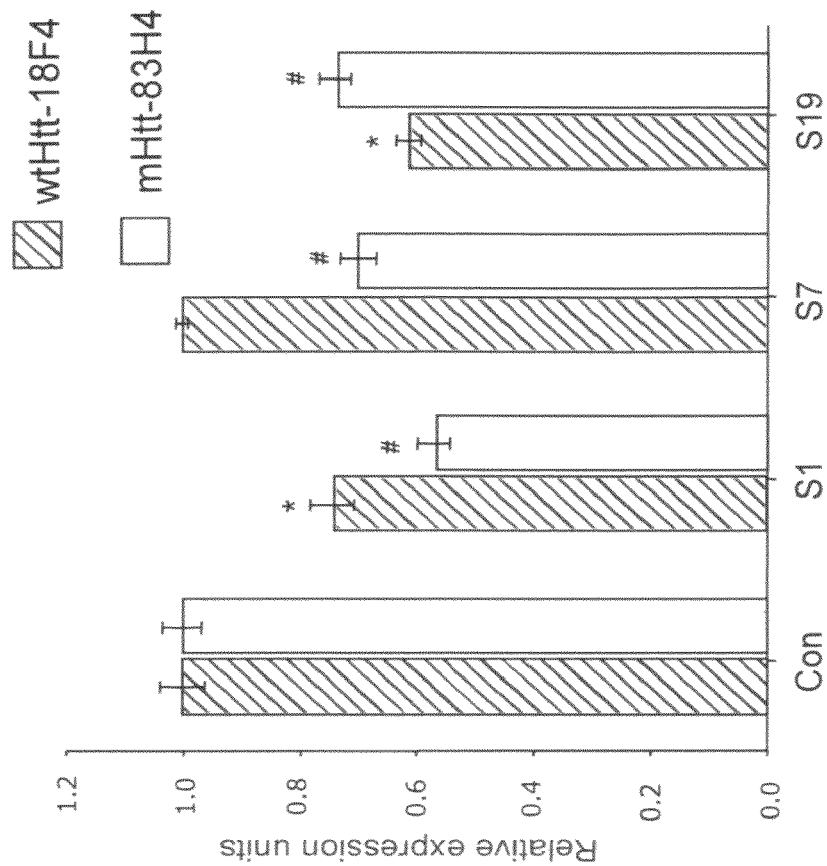
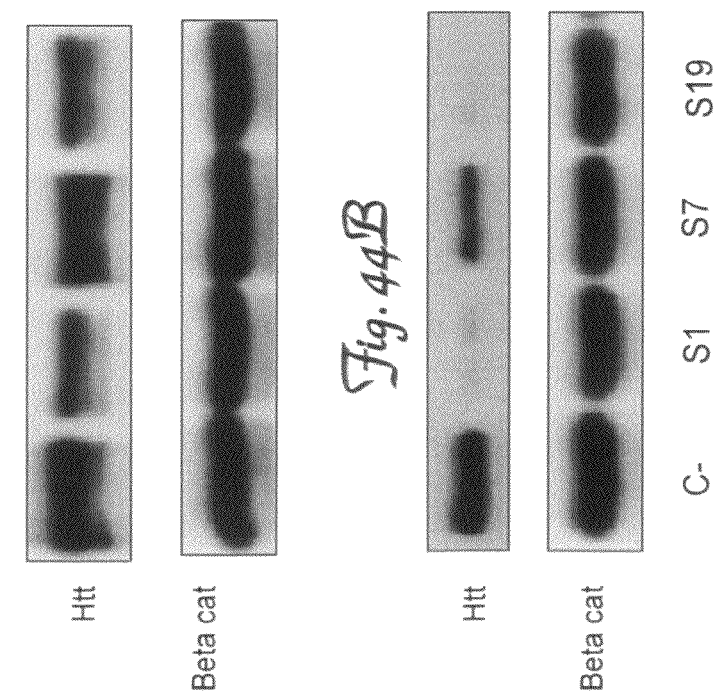
Fig. 44A
Fig. 44B
Fig. 44C

SEQUENCE LISTING

<160> NUMBER OF SEQ ID NOS: 225

<210> SEQ ID NO 1
<211> LENGTH: 79
<212> TYPE: RNA
<213> ORGANISM: Homo sapiens

<400> SEQUENCE: 1

```
gugagcgacu guaaacaucc gucacuggaa gcugugaagc cacagauggg cuuucagucg    60
gauguuugca gcugccuac                                                 79

<210> SEQ ID NO 2
<211> LENGTH: 77
<212> TYPE: RNA
<213> ORGANISM: Homo sapiens

<400> SEQUENCE: 2
gugagcgagg acacaaggcu gagcagcagc ugugaagcca cagaugggcu gcugcucagc    60
cuugugaccc ugccuac                                                   77

<210> SEQ ID NO 3
<211> LENGTH: 51
<212> TYPE: RNA
<213> ORGANISM: Homo sapiens

<400> SEQUENCE: 3
ggacacaagg cugagcagca gaucgaucug cugcucagcc uugugaccuu u              51

<210> SEQ ID NO 4
<211> LENGTH: 77
<212> TYPE: RNA
<213> ORGANISM: Homo sapiens

<400> SEQUENCE: 4
gugagcgcag aauguccuac cuucucuauc uguaaagcca cagauggggu agagaaggua    60
ggacauucuu ugccuac                                                   77

<210> SEQ ID NO 5
<211> LENGTH: 77
<212> TYPE: RNA
<213> ORGANISM: Homo sapiens

<400> SEQUENCE: 5
gugagcgaaa agaacuuuca gcuaccaagc ugugaagcca cagauggguu ugguagcuga    60
aaguucuuuc ugccuac                                                   77

<210> SEQ ID NO 6
<211> LENGTH: 111
<212> TYPE: RNA
<213> ORGANISM: Homo sapiens
<220> FEATURE:
<221> NAME/KEY: modified_base
<222> LOCATION: (1)..(16)
<223> OTHER INFORMATION: a, c, g, t, unknown or other
<220> FEATURE:
<221> NAME/KEY: modified_base
<222> LOCATION: (94)..(111)
<223> OTHER INFORMATION: a, c, g, t, unknown or other

<400> SEQUENCE: 6
nnnnnnnnnn nnnnnguga gcgaggacac aaggcugagc agcagcugug aagccacaga    60
ugggcugcug cucagccuug ugcccugcc uacnnnnnnn nnnnnnnnnn n             111

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
```

```
cccttggaga aaagccttgt ttg                                            23

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcgtttagtg aaccgtcaga tggtaccgtt taaactcgag                          40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcgtttagtg aaccgtcaga tggtaccgtt taaactcgag                          40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcgtttagtg aaccgtcaga tggtaccgtt taaactcgag                          40

<210> SEQ ID NO 11
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(28)
<223> OTHER INFORMATION: a, c, g, t, unknown or other
<220> FEATURE:
<221> NAME/KEY: modified_base
<222> LOCATION: (48)..(69)
<223> OTHER INFORMATION: a, c, g, t, unknown or other

<400> SEQUENCE: 11
ugagcgnnnn nnnnnnnnnn nnnnnnncu guaaagccac agaugggnnn nnnnnnnnnn     60
nnnnnnnnnc gccu                                                      74

<210> SEQ ID NO 12
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ugagcgaaaa gaacuuucag cuaccaagcu gugaagccac agaugggutu gguagcugaa    60
aguucuuucu gccu                                                      74
```

-continued

<210> SEQ ID NO 13
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaaactcgag tgagcgaaaa gaactttcag ctaccaagct gtgaagccac agatggg       57

<210> SEQ ID NO 14
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaaaactagt aggcagaaag aactttcagc taccaaaccc atctgtggct ttacag        56

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagaaagaac uuucagcuac cgaagcuugg guagcugaaa guucuuucuu               50

<210> SEQ ID NO 16
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctcgagaaaa aaaagaaaga actttcagct acccaagctt cggtagctga aagttctttc    60
ttaaacaacg ctttttctcc agg                                            83

<210> SEQ ID NO 17
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ugagcgcaga aagaacuuuc agcuaccgcu guaaagccac agaugggugg uagcugaaag    60
uucuuucuuu gccu                                                      74

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
aaaactcgag tgagcgcaga aagaactttc agctaccgct gtaaagccac agatggg      57
```

<210> SEQ ID NO 19
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
aaaaactagt aggcaaagaa agaactttca gctaccaccc atctgtggct ttacag        56
```

<210> SEQ ID NO 20
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
gaaagaacuu ucagcuaccg cuguaaagcc acagaugggu gguagcugaa aguucuuucu    60
u                                                                    61
```

<210> SEQ ID NO 21
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
ttttagatct aaaaaagaaa gaactttcag ctaccaccca tctgtggctt tacagcggta    60
gctgaaagtt ctttcaaaca aggcttttct ccaaggg                             97
```

<210> SEQ ID NO 22
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
ugagcgcagc ccaggucagc guugaagucu guaaagccac agaugggacu ucaacgcuga    60
ccugggcuuc gccu                                                      74
```

<210> SEQ ID NO 23
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
aaaactcgag tgagcgcagc ccaggtcagc gttgaagtct gtaaagccac agatggg       57
```

<210> SEQ ID NO 24
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
aaaaactagt aggcgaagcc caggtcagcg ttgaagtccc atctgtggct ttacag      56

<210> SEQ ID NO 25
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcccagguca gcguugaagu cguaaagcc acagauggga cuucaacgcu gaccugggcu   60
u                                                                  61

<210> SEQ ID NO 26
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttttagatct aaaaaagccc aggtcagcgt tgaagtccca tctgtggctt tacagacttc   60
aacgctgacc tgggcaaaca aggcttttct ccaaggg                            97

<210> SEQ ID NO 27
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ugagcgcagc ccaggucagc guugaagucu guaaagccac agauggacu ucaacgcuga   60 ccugggcuuc gccu                                                     74

<210> SEQ ID NO 28
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaaactcgag tgagcgcagc ccaggtcagc gttgaagtct gtaaagccac agatggg      57

<210> SEQ ID NO 29
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaaaactagt aggcgaagcc caggtcagcg ttgaagtccc atctgtggct ttacag       56

<210> SEQ ID NO 30
<211> LENGTH: 61

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gcccagguca gcguugaagu cguaaagcc acagauggga cuucaacgcu gaccugggcu      60
u                                                                     61

<210> SEQ ID NO 31
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttttagatct aaaaaagccc aggtcagcgt tgaagtccca tctgtggctt tacagacttc      60
aacgctgacc tgggcaaaca aggctttttct ccaaggg                              97

<210> SEQ ID NO 32
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ugagcgcagc acaagcugga guacaauucu guaaagccac agauggagu uguacuccag      60 cuugugcuuc gccu                                                       74

<210> SEQ ID NO 33
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aaaactcgag tgagcgcagc acaagctgga gtacaattct gtaaagccac agatggg        57

<210> SEQ ID NO 34
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aaaaactagt aggcaaagca caagctggag tacaactccc atctgtggct ttacag         56

<210> SEQ ID NO 35
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcacaagcug gaguacaauu cuguaaagcc acagauggga guuguacucc agcuugugcu     60
```

-continued u                                                              61

<210> SEQ ID NO 36
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttttagatct aaaaaagcac aagctggagt acaactccca tctgtggctt tacagaattg     60
tactccagct tgtgcaaaca aggcttttct ccaaggg                              97

<210> SEQ ID NO 37
<211> LENGTH: 130
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
uauauugcuc uugacaguga gcgcagcaca agcuggagua caauucugua aagccacaga     60
ugggaguugu acuccagcuu gugcuucgcc uacugccccg gacuucaagg ggcuacuuuu    120
aggagcaauu                                                           130

<210> SEQ ID NO 38
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aaaactcgag tatattgctc ttgacagtga gcgcagccag gtcagcgttg aagtctgtaa     60
agccacagat ggg                                                        73

<210> SEQ ID NO 39
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aaaaactagt aattgctcct aaagtagccc cttgaagtcc ggggcagtag gcgaagccca     60
ggtcagcgtt gaagtcccat ctgtggcttt acag                                 94

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aagcccgacg tcgtccag                                                   18

<210> SEQ ID NO 41

```
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttttctcgag caaaacttca acgctgacct gggcgcgatc gcctagaatt actgctcg        58

<210> SEQ ID NO 42
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ttttctcgag cccaggtcag cgttgaagtt ttctgcgatc gcctagaatt actgctcg        58

<210> SEQ ID NO 43
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ttttctcgag tcttggtagc tgaaagttct ttctttgcga tcgcctagaa ttactgctcg      60

<210> SEQ ID NO 44
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ttttctcgag aagaaagaac tttcagctac caagaagcga tcgcctagaa ttactgctcg      60

<210> SEQ ID NO 45
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttttctcgag acacaatgat tcacacggtc ttgcgatcgc ctagaattac tgctcg          56

<210> SEQ ID NO 46
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttttctcgag accgtgtgaa tcattgtttc tgcgatcgcc tagaattact gctcg            55

<210> SEQ ID NO 47
<211> LENGTH: 58
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 47
ttttctcgag gtagttgtac tccagcttgt gcccgcgatc gcctagaatt actgctcg      58

<210> SEQ ID NO 48
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttttctcgag ggcacaagct ggagtacaac tactgcgatc gcctagaatt actgctcg      58

<210> SEQ ID NO 49
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ugagcgcgac cgugugaauc auuguuuacu guaaagccac agauggguag acaaugauuc    60
acacggucac gccu                                                     74

<210> SEQ ID NO 50
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ugagcgcacc gugugaauca uugucuaacu guaaagccac agauggguua dacaaugauu    60
cacacgguac gccu                                                     74

<210> SEQ ID NO 51
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ugagcgcagc agcuugucca gguuuaugcu guaaagccac agauggguau aaaccuggac    60
aagcugcuac gccu                                                     74

<210> SEQ ID NO 52
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ugagcgcaga gcagcuuguc cagguuuacu guaaagccac agaugggugg accggacaa    60
```

-continued

```
gcugcucuac gccu                                                           74

<210> SEQ ID NO 53
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ugagcgaaga gcagcuuguc cagguuuacu guaaagccac agaugggaua accuggacaa         60
gcugcucucc gccu                                                           74

<210> SEQ ID NO 54
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ugagcgcggc gaacugaagu uuccagaacu guaaagccac agaugggguc uggaaacuuc         60
aguucgccac gccu                                                           74

<210> SEQ ID NO 55
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ugagcgccgg ccagcagcaa gcaaucaucc guaaagccac agauggggug auugcuugcu         60
gcuggccgac gccu                                                           74

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aagaaagaac tttcagctac c                                                   21

<210> SEQ ID NO 57
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aagaaagaac tttcagctac cgaagcttgg gtagctgaaa gttctttctt                    50

<210> SEQ ID NO 58
<211> LENGTH: 51
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 58
gaagaaagaa ctttcagcta ccgaagcttg ggtagctgaa agttctttct t         51

<210> SEQ ID NO 59
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aagaaagaac tttcagctac ccttcctgtc aggtagctga aagttctttc tt        52

<210> SEQ ID NO 60
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gaagaaagaa ctttcagcta cccttcctgt caggtagctg aaagttcttt ctt       53

<210> SEQ ID NO 61
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aagaaagaac tttcagctat tacttcctgt catggtagct gaaagttctt tctt      54

<210> SEQ ID NO 62
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gaagaaagaa ctttcagcta ttacttcctg tcatggtagc tgaaagttct ttctt     55

<210> SEQ ID NO 63
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aagaaagaac tttcagctat tagaagcttg tggtagctga agttctttc tt         52

<210> SEQ ID NO 64
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 64
gaagaaagaa ctttcagcta ttagaagctt gtggtagctg aaagttcttt ctt            53

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gaccgtgtga atcattgtct a                                               21

<210> SEQ ID NO 66
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gaccgtgtga atcattgtct acttcctgtc atagacaatg attcacacgg tc             52

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cagcttgtcc aggtttatga a                                               21

<210> SEQ ID NO 68
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cagcttgtcc aggtttatga acttcctgtc attcataaac ctggacaagc tg             52

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ggatacctga aatcctgctt t                                               21

<210> SEQ ID NO 70
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
```

```
ggatacctga atcctgctt tcttcctgtc aaaagcagga tttcaggtat cc        52
```

<210> SEQ ID NO 71
<211> LENGTH: 150
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (47)..(68)
<223> OTHER INFORMATION: a, c, g, t, unknown or other
<220> FEATURE:
<221> NAME/KEY: modified_base
<222> LOCATION: (88)..(109)
<223> OTHER INFORMATION: a, c, g, t, unknown or other

<400> SEQUENCE: 71

```
gcguuuagug aaccgucaga ugguaccguu uaaacucgag ugagcgnnnn nnnnnnnnnn    60
nnnnnnnncu guaaagccac agaugggnnn nnnnnnnnnn nnnnnnnnnc gccuacuaga   120
gcggccgcca gggagaucca gacaugauaa                                   150
```

<210> SEQ ID NO 72
<211> LENGTH: 158
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (47)..(68)
<223> OTHER INFORMATION: a, c, g, t, unknown or other
<220> FEATURE:
<221> NAME/KEY: modified_base
<222> LOCATION: (88)..(109)
<223> OTHER INFORMATION: a, c, g, t, unknown or other

<400> SEQUENCE: 72

```
gcguuuagug aaccgucaga ugguaccguu uaaacucgag ugagcgnnnn nnnnnnnnnn    60
nnnnnnnncu guaaagccac agaugggnnn nnnnnnnnnn nnnnnnnnnc gccuacuaga   120
gcggccgcca gggagaucca gacaugauaa gauacauu                          158
```

<210> SEQ ID NO 73
<211> LENGTH: 50
<212> TYPE: DNA
<213> ORGANISM: Homo sapiens
<220> FEATURE:
<221> NAME/KEY: modified_base
<222> LOCATION: (1)..(21)
<223> OTHER INFORMATION: a, c, g, t, unknown or other
<220> FEATURE:
<221> NAME/KEY: modified_base
<222> LOCATION: (30)..(50)
<223> OTHER INFORMATION: a, c, g, t, unknown or other

<400> SEQUENCE: 73

```
nnnnnnnnnn nnnnnnnnnn ngaagcaagn nnnnnnnnnn nnnnnnnnnn              50
```

<210> SEQ ID NO 74
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (9)..(30)
<223> OTHER INFORMATION: a, c, g, u, unknown or other
<220> FEATURE:
<221> NAME/KEY: modified_base
<222> LOCATION: (51)..(72)
<223> OTHER INFORMATION: a, c, g, u, unknown or other

<400> SEQUENCE: 74
agugaccgnn nnnnnnnnnn nnnnnnnnnn cuguaaagcc acagauggggg nnnnnnnnnn   60 nnnnnnnnnn nncgccuacu                                                80

<210> SEQ ID NO 75
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ugagcgcgac cgugugaauc auuguuuacu guaaagccac agaugggguag acaaugauuc   60 acacggucac gccu                                                      74

<210> SEQ ID NO 76
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ugagcgcacc gugugaauca uugucuaacu guaaagccac agaugggguua gacaaugauu   60 cacacgguac gccu                                                      74

<210> SEQ ID NO 77
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
ugagcgcagc agcuugucca gguuuaugcu guaaagccac agaugggguau aaaccuggac   60 aagcugcuac gccu                                                      74

<210> SEQ ID NO 78
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ugagcgcaga gcagcuuguc cagguuuacu guaaagccac agaugggguaa accuggacaa   60 gcugcucuac gccu                                                      74

<210> SEQ ID NO 79
<211> LENGTH: 74
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 79
ugagcgaaga gcagcuuguc cagguuuacu guaaagccac agauggguaa accuggacaa    60
gcugcucucc gccu    74

<210> SEQ ID NO 80
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ugagcgcggc gaacugaagu uccagaacu guaaagccac agaugggguuc uggaaacuuc    60 aguucgccac gccu    74

<210> SEQ ID NO 81
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ugagcgccgg ccagcagcaa gcaaucaucc guaaagccac agauggggug auugcuugcu    60
gcuggccgac gccu    74

<210> SEQ ID NO 82
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(5)
<223> OTHER INFORMATION: a, c, g, t, unknown or other
<220> FEATURE:
<221> NAME/KEY: modified_base
<222> LOCATION: (14)..(35)
<223> OTHER INFORMATION: a, c, g, t, unknown or other
<220> FEATURE:
<221> NAME/KEY: modified_base
<222> LOCATION: (56)..(74)
<223> OTHER INFORMATION: a, c, g, t, unknown or other
<220> FEATURE:
<221> NAME/KEY: modified_base
<222> LOCATION: (86)..(89)
<223> OTHER INFORMATION: a, c, g, t, unknown or other

<400> SEQUENCE: 82
gnnnnaguga gcgnngnnnn nnnnnnnnnn nnnnncugua aagccacaga ugggggnnnn    60
nnnnnnnnnn nnnncuucgc cuacunnnn    89

<210> SEQ ID NO 83
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(20)

```
<223> OTHER INFORMATION: a, c, g, t, unknown or other
<220> FEATURE:
<221> NAME/KEY: modified_base
<222> LOCATION: (41)..(59)
<223> OTHER INFORMATION: a, c, g, t, unknown or other

<400> SEQUENCE: 83
gnnnnnnnnn nnnnnnnnnn cuguaaagcc acagaugggg nnnnnnnnnn nnnnnnnnnc      60
uu                                                                    62

<210> SEQ ID NO 84
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
acuucaacgc ugaccugggc uuuu                                            24

<210> SEQ ID NO 85
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
acuucaacgc ugaccu                                                     16

<210> SEQ ID NO 86
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
acuucaacgc ugaccugggc                                                 20

<210> SEQ ID NO 87
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
acuucaacgc ugaccugggc                                                 20

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
acuucaacgc ugaccugggc                                                 20

<210> SEQ ID NO 89
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
acuucaacgc ugaccugggc u                                              21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
acuucaacgc ugaccugggc u                                              21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
acuucaacgc ugaccugggc u                                              21

<210> SEQ ID NO 92
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
acuucaacgc ugaccugggcuu                                              22

<210> SEQ ID NO 93
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
acuucaacgc ugaccugggc uu                                             22

<210> SEQ ID NO 94
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
acuucaacgc ugaccugggc uu                                             22

<210> SEQ ID NO 95
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 95
acuucaacgc ugaccugggc uu                                            22

<210> SEQ ID NO 96
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
acuucaacgc ugaccugggc uuu                                           23

<210> SEQ ID NO 97
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
acuucaacgc ugaccugggc uuu                                           23

<210> SEQ ID NO 98
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
acuucaacgc ugaccugggc uucg                                          24

<210> SEQ ID NO 99
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
acuucaacgc ugaccu                                                   16

<210> SEQ ID NO 100
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
acuucaacgc ugaccugggc                                               20

<210> SEQ ID NO 101
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 101
acuucaacgc ugaccugggc                                                    20

<210> SEQ ID NO 102
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
acuucaacgc ugaccugggc                                                    20

<210> SEQ ID NO 103
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
acuucaacgc ugaccugggc                                                    20

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
acuucaacgc ugaccugggc u                                                  21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
acuucaacgc ugaccugggc u                                                  21

<210> SEQ ID NO 106
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
acuucaacgc ugaccugggc uu                                                 22

<210> SEQ ID NO 107
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 107
acuucaacgc ugaccugggc uu                                          22

<210> SEQ ID NO 108
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
acuucaacgc ugaccugggc uu                                          22

<210> SEQ ID NO 109
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
acuucaacgc ugaccugggc uu                                          22

<210> SEQ ID NO 110
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
acuucaacgc ugaccugggc uu                                          22

<210> SEQ ID NO 111
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
acuucaacgc ugaccugggc uuc                                         23

<210> SEQ ID NO 112
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
gcccagguca gcguugaagu cug                                         23

<210> SEQ ID NO 113
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
```

-continued ccaggucagc guuga                                                15

<210> SEQ ID NO 114
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gcccagguca gcguugaagu                                           20

<210> SEQ ID NO 115
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
gcccagguca gcguugaagu                                           20

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gcccagguca gcguugaagu c                                         21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
gcccagguca gcguugaagu c                                         21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
gcccagguca gcguugaagu c                                         21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
gcccagguca gcguugaagu c                                         21

```
<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gcccagguca gcguugaagu c                                                   21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gcccagguca gcguugaagu c                                                   21

<210> SEQ ID NO 122
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gcccagguca gcguugaagu cu                                                  22

<210> SEQ ID NO 123
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
gcccagguca gcguugaagu cug                                                 23

<210> SEQ ID NO 124
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ccaggucagc guuga                                                          15

<210> SEQ ID NO 125
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gcccagguca gcguugaagu                                                     20

<210> SEQ ID NO 126
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gcccagguca gcguugaagu                                                     20

<210> SEQ ID NO 127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gcccagguca gcguugaagu                                                     20

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
gcccagguca gcguugaagu c                                                   21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gcccagguca gcguugaagu c                                                   21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
gcccagguca gcguugaagu c                                                   21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gcccagguca gcguugaagu c                                                   21

<210> SEQ ID NO 132
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 132
gcccagguca gcguugaagu c                                              21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
gcccagguca gcguugaagu c                                              21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
gcccagguca gcguugaagu c                                              21

<210> SEQ ID NO 135
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gcccagguca gcguugaagu cu                                             22

<210> SEQ ID NO 136
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
gcccagguca gcguugaagu cuguaaagcc acagauggga cuucaacgcu gaccugggcu    60
u                                                                    61

<210> SEQ ID NO 137
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(5)
<223> OTHER INFORMATION: a, c, g, t, unknown or other
<220> FEATURE:
<221> NAME/KEY: modified_base
<222> LOCATION: (84)..(86)
<223> OTHER INFORMATION: a, c, g, t, unknown or other
```

-continued

```
<400> SEQUENCE: 137
gnnnagugag cgcagcccag gucagcguug aagucuguaa agccacagau gggacuucaa      60
cgcugaccug ggcuucgccu acunnn                                          86

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
gcccagguca gcguugaagu c                                               21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uucgggucca gucgcaacuu c                                               21

<210> SEQ ID NO 140
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gcgagucggc ccgaggccuc cuucgcucag ccgggcuccg ga                        42

<210> SEQ ID NO 141
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
aaaagcugau gaaggccuuc guuuuuucga cuacuuccgg aa                        42

<210> SEQ ID NO 142
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ugaggagccg cugcaccgac cuuacuccuc ggcgacgugg cu                        42

<210> SEQ ID NO 143
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 143
gccgcugcac cgaccaaaga auucggcgac guggcugguu uc                              42

<210> SEQ ID NO 144
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
gcagcagcag cagcaacagc cuucgucguc gucgucguug uc                              42

<210> SEQ ID NO 145
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
auggcgaccc uggaaaagcu guuuaccgcu gggaccuuuu cg                              42

<210> SEQ ID NO 146
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
aagcugauga aggccuucga guuucgacu acuuccggaa gc                               42

<210> SEQ ID NO 147
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gcucagguuc ugcuuuuacc uuucgagucc aagacgaaaa ug                              42

<210> SEQ ID NO 148
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
aagaaagaac uuucagcuac cuuuucuuuc uugaaagucg au                              42

<210> SEQ ID NO 149
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
```
agaacuuuca gcuaccaaga auuucuugaa agucgauggu uc                      42

<210> SEQ ID NO 150
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
aagaaagacc gugugaauca uuuuucuuuc uggcacacuu ag                      42

<210> SEQ ID NO 151
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gaccguguga aucauugucu auucaggcac acuuaguaac ag                      42

<210> SEQ ID NO 152
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gucugacaau augugaaaac auucagacug uuauacacuu uu                      42

<210> SEQ ID NO 153
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
uggcacaguc ugucagaaau uuuaccgugu cagacagucu uu                      42

<210> SEQ ID NO 154
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gggcaucgcu auggaacugu uucccguag cgauaccuug ac                       42

<210> SEQ ID NO 155
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
aaugccucaa caaaguuauc auuuuacgga guuguuucaa ua                      42

<210> SEQ ID NO 156
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
agcuuugaug gauucuaauc uuuucgaaac uaccuaagau ua                42

<210> SEQ ID NO 157
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
cagcuugucc agguuuauga auugucgaac agguccaaau ac                42

<210> SEQ ID NO 158
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
ccugccaugg accugaauga uuuggacggu accuggacuu ac                42

<210> SEQ ID NO 159
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
caucuugaac uacaucgauc auuguagaac uugauguagc ua                42

<210> SEQ ID NO 160
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
aacuacaucg aucauggaga cuuuugaugu agcuaguacc uc                42

<210> SEQ ID NO 161
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
caaacugcau gauguccuga auuguuugac guacuacagg ac                42

<210> SEQ ID NO 162

```
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ggauaccuga aauccugcuu uuuccuaugg acuuuaggac ga                              42

<210> SEQ ID NO 163
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
cgugcagaua agaaugcuau uuugcacguc uauucuuacg au                              42

<210> SEQ ID NO 164
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
aagugggcca guucagggaa uuuuucaccc ggucaagucc cu                              42

<210> SEQ ID NO 165
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
guucagggaa ucagaggcaa uuucaagucc cuuagucucc gu                              42

<210> SEQ ID NO 166
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
caucauggcc aguggaagga auuguaguac cggucaccuu cc                              42

<210> SEQ ID NO 167
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
cagcagugcc acaaggagaa uuugucguca cgguguuccu cu                              42

<210> SEQ ID NO 168
<211> LENGTH: 42
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 168
ugaagcccuu ggaguguuaa auuacuucgg gaaccucaca au                              42

<210> SEQ ID NO 169
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
agcccuugga guguuaaaua cuuucgggaa ccucacaauu ua                              42

<210> SEQ ID NO 170
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
cuggaauguu ccggagaauc auugaccuua caaggccucu ua                              42

<210> SEQ ID NO 171
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
uucucuucug ugauuauguc uuuaagagaa gacacuaaua ca                              42

<210> SEQ ID NO 172
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gacgaggaag aggaggaggc cuucugcucc uucuccuccu cc                              42

<210> SEQ ID NO 173
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
aagaggagga ggccgacgcc cuuucucccu ccuccggcug cg                              42

<210> SEQ ID NO 174
<211> LENGTH: 42
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 174
guccaccccc uccaucauuu auucaggugg gggagguagu aa                     42

<210> SEQ ID NO 175
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
gaccguguga aucauugucu acuuccuguc auagacaaug auucacacgg ucuu        54

<210> SEQ ID NO 176
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
cagcuugucc agguuuauga acuuccuguc auucauaaac cuggacaagc uguu        54

<210> SEQ ID NO 177
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
ggauaccuga aauccugcuu ucuuccuguc aaaagcagga uuucagguau ccuu        54

<210> SEQ ID NO 178
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
gaccguguga aucauugucu acuuccuguc auagacaaug auucacacgg ucuu        54

<210> SEQ ID NO 179
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(4)
<223> OTHER INFORMATION: a, c, g, t, unknown or other
<220> FEATURE:
<221> NAME/KEY: modified_base
<222> LOCATION: (84)..(86)
<223> OTHER INFORMATION: a, c, g, t, unknown or other

<400> SEQUENCE: 179
gnnnagugag cgcaccgugu gaaucauugu cuaacuguaa agccacagau ggguuagaca  60
```

```
augauucaca cgguacgccu acunnn                                           86
```

<210> SEQ ID NO 180
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180

```
ugguaccguu                                                             10
```

<210> SEQ ID NO 181
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181

```
agcggccgcc a                                                           11
```

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(17)
<223> OTHER INFORMATION: a, c, g t, unknown or other

<400> SEQUENCE: 182

```
cunnnnnnnn nnnnnnngg                                                   19
```

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(17)
<223> OTHER INFORMATION: a, c, g, t, unknown or other

<400> SEQUENCE: 183

```
ccnnnnnnnn nnnnnnngg                                                   19
```

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184

```
cugugaagcc acagauggg                                                   19
```

<210> SEQ ID NO 185
<211> LENGTH: 19
<212> TYPE: RNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 185
ccgugaagcc acagaugggg                                                   19

<210> SEQ ID NO 186
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
aaaagaacuu ucagcuacca ag                                                22

<210> SEQ ID NO 187
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
uuugguagcu gaaaguucuu uc                                                22

<210> SEQ ID NO 188
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
cagaaagaac uuucagcuac cg                                                22

<210> SEQ ID NO 189
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
ugguagcuga aaguucuuuc uu                                                22

<210> SEQ ID NO 190
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
cagcccaggu cagcguugaa gu                                                22

<210> SEQ ID NO 191
<211> LENGTH: 22
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 191
acuucaacgc ugaccugggc uu                                              22

<210> SEQ ID NO 192
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
cagcacaagc uggaguacaa uu                                              22

<210> SEQ ID NO 193
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
aguuguacuc cagcuugugc uu                                              22

<210> SEQ ID NO 194
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
cagcacaagc uggaguacaa uu                                              22

<210> SEQ ID NO 195
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
aguuguacuc cagcuugugc uu                                              22

<210> SEQ ID NO 196
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
cgaccgugug aaucauuguu ua                                              22

<210> SEQ ID NO 197
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 197
uagacaauga uucacacggu ca                                              22

<210> SEQ ID NO 198
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
caccguguga aucauugucu aa                                              22

<210> SEQ ID NO 199
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
cauuagacaa ugauucacac ggua                                            24

<210> SEQ ID NO 200
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
cagcagcuug uccagguuua ug                                              22

<210> SEQ ID NO 201
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uauaaaccug gacaagcugc ua                                              22

<210> SEQ ID NO 202
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
cagagcagcu uguccagguu ua                                              22

<210> SEQ ID NO 203
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
```

```
uaaaccugga caagcugcuc ua                                              22

<210> SEQ ID NO 204
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
aagagcagcu uguccagguu ua                                              22

<210> SEQ ID NO 205
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uaaaccugga caagcugcuc uc                                              22

<210> SEQ ID NO 206
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
cggcgaacug aaguuccag aa                                               22

<210> SEQ ID NO 207
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
uucuggaaac uucaguucgc ca                                              22

<210> SEQ ID NO 208
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
cgaccgugug aaucauuguu uaccggccag cagcaagcaa ucau                      44

<210> SEQ ID NO 209
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
gugauugcuu gcugcuggcc ga                                              22
```

```
<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
ttaatacgac tcactatagg t                                          21

<210> SEQ ID NO 211
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
acttcaacgc tgacct                                                16

<210> SEQ ID NO 212
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
ccaggtcagc gttga                                                 15

<210> SEQ ID NO 213
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
aaatctagat acatacttct ttacattcca ccgcttcgag cagacatg             48

<210> SEQ ID NO 214
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
aaaaggatcc tcgagcgatt ttaccacatt tgtagagg                        38

<210> SEQ ID NO 215
<211> LENGTH: 21
<212> TYPE: RNA
<213> ORGANISM: Homo sapiens

<400> SEQUENCE: 215
augaaggccu ucgagucccu c                                          21

<210> SEQ ID NO 216
<211> LENGTH: 21
<212> TYPE: RNA
<213> ORGANISM: Homo sapiens
```

```
<400> SEQUENCE: 216
ggcgaccctg gaaaagcuga u                                               21

<210> SEQ ID NO 217
<211> LENGTH: 21
<212> TYPE: RNA
<213> ORGANISM: Homo sapiens

<400> SEQUENCE: 217
uggcgacccu ggaaaagcug a                                               21

<210> SEQ ID NO 218
<211> LENGTH: 21
<212> TYPE: RNA
<213> ORGANISM: Homo sapiens

<400> SEQUENCE: 218
auggcgaccc uggaaaagcu g                                               21

<210> SEQ ID NO 219
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
aaaacucgag ugagcgcuga aggccuucga gucccucacc guaaagccac agauggguga     60
gggacucgaa ggccuucauc gccuacuagu aaaa                                 94

<210> SEQ ID NO 220
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
aaaacucgag ugagcgcuga aggccuucga gucuuuuacc guaaagccac agauggguga     60
gggacucgaa ggccuucauc gccuacuagu aaaa                                 94

<210> SEQ ID NO 221
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
aaaacucgag ugagcgcaug aaggccuucg aguccucccc guaaagccac agauggggag     60
ggacucgaag gccuucaucc gccuacuagu aaaa                                 94

<210> SEQ ID NO 222
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
```

```
aaaacucgag ugagcgcaug aaggccuucg agucuuuucc guaaagccac agauggggag    60
ggacucgaag gccuucaucc gccuacuagu aaaa                               94

<210> SEQ ID NO 223
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
actagttcta gagcggccgc cacagcgggg agatccagac a                       41

<210> SEQ ID NO 224
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
actagagcgg ccgccacagc ggggagatcc agacatgatg a                       41

<210> SEQ ID NO 225
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
actagaacat aatcagccat accacatttg tagaggtttt a                       41
```

REDUCTION OF OFF-TARGET RNA INTERFERENCE TOXICITY

PRIORITY OF INVENTION

The present patent application is a continuation-in-part application of U.S. application Ser. No. 12/111,025 filed on Apr. 28, 2008, which claims priority under 35 U.S.C. §119(e) to U.S. Provisional Application No. 60/914,309 filed on Apr. 26, 2007. The present patent application also claims priority under 35 U.S.C. §119(e) to U.S. Provisional Application No. 60/932,468 filed on May 31, 2007, to U.S. Provisional Application No. 61/038,685 filed on Mar. 21, 2008, and to U.S. Provisional Application No. 61/070,622 filed on Mar. 25, 2008.

The present application claims the benefit of all of the above-listed applications, which are hereby incorporated by reference herein in their entireties, including the drawings.

GOVERNMENT SUPPORT

This invention was made with government support under NS-50210, HD044093, DK-54759 and NS-592372 awarded by the National Institutes of Health. The government has certain rights in the invention.

BACKGROUND OF THE INVENTION

Double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shutdown of protein synthesis. Interference of gene expression by RNAi molecules is now recognized as a naturally occurring strategy for silencing genes in the cells of many organisms.

Cells can contain various small dsRNAs (~21-25 bp). Two types of small RNA molecules have a post-transcriptional effect: (1) siRNA molecules that induce mRNA degradation, and (2) miRNAs, also called microRNAs, that induce translational inhibition. Other small RNAs work at the transcriptional level by affecting DNA and histone methylation. RNAi molecules can be generated exogenously (e.g., siRNA molecules), and induce transient gene silencing. Alternatively, RNAi molecules can be introduced via a vector that expresses short-hairpin RNAs (shRNA) in order to exhibit persistent gene silencing.

SUMMARY OF THE INVENTION

The present invention provides an isolated miRNA shuttle vector that expresses a therapeutic siRNA with limited off target toxicity. In certain embodiments, embedding an siRNA that exhibits off target toxicity in the context of an shRNA shuttle vector within the miRNA shuttle vectors of the present invention limits the off target toxicity of the siRNA. In certain embodiments, the miRNA shuttle vector expresses a therapeutic siRNA in the brain with limited off target toxicity. In certain embodiments, the miRNA shuttle vector expresses a therapeutic siRNA in the striatum with limited off target toxicity. In certain embodiments, the miRNA shuttle vector expresses a therapeutic siRNA in the cerebrum with limited off target toxicity.

The present invention provides an isolated nucleic acid encoding a primary transcript (pri-miRNA) including, in order of position, a 5'-flanking region, a first siRNA region, a loop region, a second siRNA region, and a 3'-flanking region (FIG. 20A-20F). In certain embodiments, the 5'-flanking region is contiguously linked to the first siRNA region, the loop region is positioned between the first siRNA region and the second siRNA region, and the second siRNA region is contiguously linked to the 3'-flanking region. In certain embodiments, the first siRNA region is a non-guide region and the second siRNA region is a guide region, and in other embodiments the first siRNA region is a guide region and the second siRNA region is a non-guide region. As used herein, the term "siRNA guide region" is a single-stranded sequence of RNA that is complementary to a target sequence. As used herein, the term "siRNA non-guide region" is a single-stranded sequence of RNA that is complementary to the "siRNA guide region." Thus, under the proper conditions, the siRNA guide region and the siRNA non-guide region associate to form an RNA duplex. As used herein, all nucleic acid sequences are listed, as is customary, in a 5' to 3' direction.

In certain embodiments, the first siRNA region is about 20-30 nucleotides in length, and is about 70-100% complementary to the second siRNA region, which is also about 20-30 nucleotides in length.

In certain embodiments, the 5'-flanking region contains a 5'-joining sequence contiguously linked to the first siRNA region (FIGS. 20B and 20C). As used herein, the term "joining site" or a "joining sequence" is a short nucleic acid sequence of less than 60 nucleotides that connects two other nucleic acid sequences. In certain embodiments, the joining site is of a length of any integer between 4 and 50, inclusive. In certain embodiments, the 5'-joining sequence consists of 5-7 nucleotides (e.g., consists of 6 nucleotides). In certain embodiments, the 5'-joining sequence encodes GUGASSS, wherein S is either a G or C nucleotide (i.e., the 5'-joining sequence encodes UGACCC, UGACCG, UGACGC, UGAGCC, UGACGG, UGAGGC, UGAGCG, or UGAGGG). In certain embodiments, the 5'-joining sequence encodes GUGAGCG.

In certain embodiments, the 5'-flanking region further comprises a 5'-bulge sequence positioned upstream from the 5'-joining sequence. As used herein, the term "bulge sequence" is a region of nucleic acid that is non-complementary to the nucleic acid opposite it in a duplex. For example, a duplex will contain a region of complementary nucleic acids, then a region of non-complementary nucleic acids, followed by a second region of complementary nucleic acids. The regions of complementary nucleic acids will bind to each other, whereas the central non-complementary region will not bind, thereby forming a "bulge." In certain embodiments the two strands of nucleic acid positioned between the two complementary regions will be of different lengths, thereby forming a "bulge." In certain embodiments, the 5'-bulge sequence will contain from 2 to 15 nucleotides. In certain embodiments, the 5'-bulge sequence consists of about 1-10 nucleotides. In certain embodiments, the 5'-bulge sequence encodes UAAACUCGA. In certain embodiments, the 5'-bulge sequence has from 0-50% complementarity to the 3'-bulge sequence. The XhoI restriction site is CTCGAG (with "T" being "U" in RNA form in this and all other sequences listed herein).

In certain embodiments, the 5'-flanking region further contains a 5'-spacer sequence positioned upstream from the 5'-bulge sequence. In certain embodiments, the 5'-spacer sequence consists of 9-12 nucleotides, such as 10-12 nucleotides. In certain embodiments, the 5'-spacer sequence has from 60-100% complementarity to a 3'-spacer sequence. In certain embodiments, the 5'-bulge sequence comprises a cloning site, such as an XhoI site. In certain embodiments, the 5'-spacer sequence is UGGUACCGUU (SEQ ID NO:180).

In certain embodiments, the 5'-flanking region further contains a 5'-upstream sequence positioned upstream from the 5'-spacer sequence. In certain embodiments, the 5'-upstream sequence is about 5-5000 nucleotides in length, such as 30-2000 nucleotides in length.

In certain embodiments, the 3'-flanking region contains a 3'-joining sequence contiguously linked to the second siRNA region (FIGS. 20D and 20E). In certain embodiments, the joining site is of a length of any integer between 4 and 50, inclusive. In certain embodiments, the 3'-joining sequence consists of 5-7 nucleotides, (e.g., consists of 6 nucleotides). In certain embodiments, the 3'-joining sequence is at least about 85% complementary to a 5'-joining sequence. In certain embodiments, the 3'-joining sequence encodes CGCYUAC, wherein Y is C or U. In certain embodiments, the 3'-joining sequence encodes CGCCUAC.

In certain embodiments, the 3'-flanking region further comprises a 3'-bulge sequence positioned downstream from the 3'-joining sequence. In certain embodiments, the 3'-bulge sequence comprises a cloning site, such as a SpeI/XbaI site or a SpeI site. The SpeI/XbaI site is encoded by CTCAGA, and the SpeI site is encoded by CTCAGT. In certain embodiments, the 3'-bulge sequence consists of about 1-15 nucleotides (such as 2-15 nucleotides or 1-10 nucleotides). In certain embodiments, the 3'-bulge sequence encodes UAG. In certain embodiments, the 5'-bulge sequence is complementary to the 3'-bulge sequence at only one nucleotide at each end of the sequence.

In certain embodiments, the 3'-flanking region further contains a 3'-spacer sequence positioned downstream from the 3'-bulge sequence. In certain embodiments, the 3'-spacer sequence consists of 9-12 nucleotides, such as 10-12 nucleotides. In certain embodiments, the 3'-spacer sequence is AGCGGCCGCCA (SEQ ID NO:181). In certain embodiments, the 3'-spacer sequence is at least about 70% complementary to a 5'-spacer sequence.

In certain embodiments, the 3'-flanking region further contains a 3'-downstream sequence positioned downstream from the 3'-spacer sequence. In certain embodiments, a 5'-upstream sequence does not significantly pair with the 3'-downstream sequence. As used herein, the term "does not significantly pair with" means that the two strands are less than 20% homologous. In certain embodiments, the 3'-downstream sequence is about 5-5000 nucleotides in length, such as 30-2000 nucleotides in length.

In certain embodiments, the loop region is from 4-20 nucleotides in length, such as 15-19 nucleotides in length. From 0-50% of the loop region can be complementary to another portion of the loop region. As used herein, the term "loop region" is a sequence that joins two complementary strands of nucleic acid. In certain embodiments, 1-3 nucleotides of the loop region are immediately contiguous to the complementary strands of nucleic acid may be complementary to the last 1-3 nucleotides of the loop region. For example, the first two nucleic acids in the loop region may be complementary to the last two nucleotides of the loop region. In certain embodiments, the loop region is 17 nucleotides in length. In certain embodiments, the loop region encodes CUNNNNNNNNNNNNNNNGG (SEQ ID NO:182) or CCNNNNNNNNNNNNNNNGG (SEQ ID NO: 183). In certain embodiments, the loop region encodes CUGUGAAGC-CACAGAUGGG (SEQ ID NO: 184) or CCGUGAAGCCA-CAGAUGGG (SEQ ID NO: 185).

The present invention further provides an RNA encoded by nucleic acid described herein.

The present invention further provides an expression cassette containing a promoter contiguously linked to the nucleic acid described herein. In certain embodiments, the promoter is a polII or a polIII promoter, such as a U6 promoter (e.g., a mouse U6 promoter). In certain embodiments, the expression cassette further contains a marker gene. In certain embodiments, the promoter is a polII promoter. In certain embodiments, the promoter is a tissue-specific promoter. In certain embodiments, the promoter is an inducible promoter. In certain embodiments, the promoter is a polIII promoter.

The present invention provides a vector containing an expression cassette described herein. In certain embodiments, the vector is an adeno-associated virus (AAV) vector.

The present invention provides a non-human animal comprising the nucleic acid, the expression cassette, or the vector described herein.

The present invention provides a composition that comprises shHD(2.1), shHD(2.1b), sh1913, shGFP, miSCA1, shSCA1, miJNK, miHTT, miHD2.4, miHD2.4.2, miHD8.2, miHD8.2.2, miHD8.2.3, miSCA1-2225 or miSCA1-1399.

The present invention provides an expression cassette encoding shHD(2.1), shHD(2.1b), sh1913, shGFP, miSCA1, shSCA1, miJNK, miHTT, miHD2.4, miHD2.4.2, miHD8.2, miHD8.2.2, miHD8.2.3, miSCA1-2225 or miSCA1-1399. In certain embodiments, the expression cassette further contains a marker gene.

The present invention provides a vector comprising an expression cassette encoding shHD(2.1), shHD(2.1b), sh1913, shGFP, miSCA1, shSCA1, miJNK, miHTT, miHD2.4, miHD2.4.2, miHD8.2, miHD8.2.2, miHD8.2.3, miSCA1-2225 or miSCA1-1399.

The present invention provides a non-human animal comprising shHD(2.1), shHD(2.1b), sh1913, shGFP, miSCA1, shSCA1, miJNK, miHTT, miHD2.4, miHD2.4.2, miHD8.2, miHD8.2.2, miHD8.2.3, miSCA1-2225 or miSCA1-1399, or an expression cassette or vector encoding these shRNAs or miRNAs.

The present invention provides method of inducing RNA interference by administering to a subject a nucleic acid, an expression cassette, a vector, or a composition described herein.

The present invention provides a vector containing a U6 promoter operably linked to a nucleic acid encoding an miRNA. The predicted transcription start sites of constructs of the present invention are different from those used by researchers in the past. In certain embodiments of the present invention, the U6miRNA has an extended 5' end. If the 5' end is truncated to resemble the previous CMV-based strategy, silencing efficacy is severely reduced. The present invention also provides improved flanking sequences that show improved efficacy over natural miR-30 flanking sequences. The use of the present miRNA strategy appears to alleviate toxicity associated with traditional shRNA approaches. The miRNA strategy does not generally generate excessive amounts of RNAi as do U6shRNA approaches.

As used herein the term "stem sequence" is a sequence that is complementary to another sequence in the same molecule, where the two complementary strands anneal to form a duplex (e.g., the first and second siRNA regions). The duplex that is formed maybe fully complementary, or may be less than fully complementary, such as 99%, 98%, 97%, 96%, 95,%, 94%, 93%, 92%, 91%, 90%, 89%, 88%, 87%, 86%, 85%, 84%, 83%, 82%, 81%, 80%, 75%, or 70% complementary to each other. Further, in certain embodiments, one strand may contain more nucleotides than the other strand, allowing the formation of a side loop.

In certain embodiments, a first siRNA region consists of 5'-AAAAGAACUUUCAGCUACCAAG-3' (SEQ ID NO:

186) and the second siRNA region consists of 5'-UUUG-GUAGCUGAAAGUUCUUUC-3' (SEQ ID NO:187) (see FIG. 16, miHD(2.1)).

In certain embodiments, a first siRNA region consists of 5'-CAGAAAGAACUUUCAGCUACCG-3' (SEQ ID NO: 188) and a second siRNA region consists of 5'-UG-GUAGCUGAAAGUUCUUUCUU-3' (SEQ ID NO: 189) (see FIG. 16, miHD(2.1b)).

In certain embodiments, a first siRNA region consists of 5'-CAGCCCAGGUCAGCGUUGAAGU-3' (SEQ ID NO:190) and a second siRNA region consists of 5'-ACU-UCAACGCUGACCUGGGCUU-3' (SEQ ID NO:191) (see FIG. 16, mi1913).

In certain embodiments, a first siRNA region consists of 5'-CAGCACAAGCUGGAGUACAAUU-3' (SEQ ID NO: 192) and a second siRNA region consists of 5'-AGUU-GUACUCCAGCUUGUGCUU-3' (SEQ ID NO:193) (see FIG. 16, miGFP).

In certain embodiments, a first siRNA region consists of 5'-CAGCACAAGCUGGAGUACAAUU-3' (SEQ ID NO:194) and a second siRNA region consists of 5'-AGUU-GUACUCCAGCUUGUGCUU-3' (SEQ ID NO:195) (see FIG. 16, mi1913-miR30 variant).

In certain embodiments, a first siRNA region consists of 5'-CGACCGUGUGAAUCAUUGUUUA-3' (SEQ ID NO:196) and a second siRNA region consists of 5'-UAGA-CAAUGAUUCACACGGUCA-3' (SEQ ID NO: 197) (see FIG. 19, miHD2.4).

In certain embodiments, a first siRNA region consists of 5'-CACCGUGUGAAUCAUUGUCUAA-3' (SEQ ID NO:198) and a second siRNA region consists of 5'-CAUUA-GACAAUGAUUCACACGGUA-3' (SEQ ID NO: 199) (see FIG. 19, miHD2.4.2).

In certain embodiments, a first siRNA region consists of 5'-CAGCAGCUUGUCCAGGUUUAUG-3' (SEQ ID NO:200) and a second siRNA region consists of 5'-UAUAAACCUGGACAAGCUGCUA-3' (SEQ ID NO:201) (see FIG. 19, miHD8.2).

In certain embodiments, a first siRNA region consists of 5'-CAGAGCAGCUUGUCCAGGUUUA-3' (SEQ ID NO:202) and a second siRNA region consists s of 5'-UAAACCUGGACAAGCUGCUCUA-3' (SEQ ID NO:203) (see FIG. 19, miHD8.2.2).

In certain embodiments, a first siRNA region consists of 5'-AAGAGCAGCUUGUCCAGGUUUA-3' (SEQ ID NO:204) and a second siRNA region consists of 5'-UAAAC-CUGGACAAGCUGCUCUC-3' (SEQ ID NO:205) (see FIG. 19, miHD8.2.3).

In certain embodiments, a first siRNA region consists of 5'-CGGCGAACUGAAGUUUCCAGAA-3' (SEQ ID NO:206) and a second siRNA region consists of 5'-UUCUG-GAAACUUCAGUUCGCCA-3' (SEQ ID NO:207) (see FIG. 19, miSCA1-2225).

In certain embodiments, a first siRNA region consists of 5'-CGACCGUGUGAAUCAUUGUUUACCGGC-CAGCAGCAAGCAAUCAU-3' (SEQ ID NO:208) and a second siRNA region consists of 5'-GUGAUUGCU-UGCUGCUGGCCGA-3' (SEQ ID NO:209) (see FIG. 19, miSCA1-1399).

In certain embodiments, the nucleic acid of the invention does not encode a sequence consisting of SEQ ID NO:219, SEQ ID NO:220, SEQ ID NO:221 or SEQ ID NO:222.

The present invention also provides vectors containing the expression cassettes described herein. Examples of appropriate vectors include adenoviral, lentiviral, adeno-associated viral (AAV), poliovirus, herpes simplex virus (HSV), or murine Maloney-based viral vectors. In one embodiment, the vector is an adeno-associated virus vector. These cassettes and vectors may be contained in a cell, such as a mammalian cell. A non-human mammal may contain the cassette or vector.

The present invention provides cells (such as a mammalian cell) containing the nucleic acid molecules, expression cassettes or vectors described herein. The present invention also provides a non-human mammal containing the nucleic acid molecules, expression cassettes or vectors described herein.

The present invention provides a nucleic acid, an expression cassette, a vector, or a composition as described herein for use in therapy, such as for treating a neurodegenerative disease.

The present invention provides an isolated RNAi molecule having a microRNA having an overhang at the 3' end. In certain embodiments, the overhang is a 2 to 5-nucleotide repeat. In certain embodiments, the overhang is a UU, UUU, UUUU CUU, CUUU or CUUUU sequence. In certain embodiments, the microRNA is a naturally-occurring microRNA. In certain embodiments, microRNA is an artificial microRNA. In certain embodiments, the RNAi molecule produces a decreased level of off-target toxicity.

The present invention provides a method of inducing low-toxicity RNA interference by administering to a subject a nucleic acid, an expression cassette, a vector, or a composition as described herein. In certain embodiments, the expression cassette contains a polII promoter.

The present invention provides a method of inducing low-toxicity RNA interference by administering to a subject an expression cassette encoding a polII promoter operably linked to a nucleic acid encoding a miRNA. In certain embodiments, the miRNA comprises a 2- or 3-nucleotide 5' or 3'-overhang. In certain embodiments, the miRNA comprises a 2-nucleotide 3'-overhang. In certain embodiments, the miRNA is an artificial miRNA.

The present invention provides a method of treating a subject with a neurodegenerative disease by administering to the subject a nucleic acid, an expression cassette, a vector, or a composition as described herein so as to treat the neurodegenerative disease. In certain embodiments, the neurodegenerative disease is a trinucleotide repeat disease. In certain embodiments, the neurodegenerative disease Huntington's Disease or spinocerebellar ataxia.

The present invention provides a method of suppressing the accumulation of a polyglutamine gene-encoded protein (such as huntingtin or ataxin-1) in a cell by introducing a nucleic acid molecules (e.g., a ribonucleic acid (RNA)) described herein into the cell in an amount sufficient to suppress accumulation of huntingtin or ataxin-1 in the cell. In certain embodiments, the accumulation of huntingtin or ataxin-1 is suppressed by at least 10%. In certain embodiments, the accumulation of huntingtin or ataxin-1 is suppressed by at least 10%, 20%, 30%, 40%, 50%, 60%, 70%, 80%, 90% 95%, or 99%. In certain embodiments, the suppression of the accumulation of the protein is in an amount sufficient to cause a therapeutic effect, e.g., to reduce the formation of tangles.

The present invention provides a method of preventing cytotoxic effects of mutant huntingtin or ataxin-1 in a cell by introducing a nucleic acid molecules (e.g., a ribonucleic acid (RNA)) described herein into the cell in an amount sufficient to suppress accumulation of huntingtin or ataxin-1. In certain embodiments, the nucleic acid molecules prevents cytotoxic effects of huntingtin or ataxin-1, e.g., in a neuronal cell.

The present invention provides a method to inhibit expression of a huntingtin or ataxin-1 gene in a cell by introducing a nucleic acid molecule (e.g., a ribonucleic acid (RNA))

described herein into the cell in an amount sufficient to inhibit expression of the huntingtin or ataxin-1, and wherein the RNA inhibits expression of the huntingtin or ataxin-1 gene. In certain embodiments, the huntingtin or ataxin-1 is inhibited by at least 10%, 20%, 30%, 40%, 50%, 60%, 70%, 80%, 90% 95%, or 99%.

The present invention provides a method to inhibit expression of a huntingtin or ataxin-1 gene in a mammal (e.g., a human or a non-human mammal) by (a) providing a mammal containing a neuronal cell, wherein the neuronal cell contains the huntingtin or ataxin-1 gene and the neuronal cell is susceptible to RNA interference, and the huntingtin or ataxin-1 gene is expressed in the neuronal cell; and (b) contacting the mammal with a ribonucleic acid (RNA) or a vector described herein, thereby inhibiting expression of the huntingtin or ataxin-1 gene. In certain embodiments, the accumulation of huntingtin or ataxin-1 is suppressed by at least 10%. In certain embodiments, the huntingtin or ataxin-1 is inhibited by at least 10%, 20%, 30%, 40%, 50%, 60%, 70%, 80%, 90% 95%, or 99%. In certain embodiments, the cell is located in vivo in a mammal.

The present invention provides a viral vector comprising a promoter and a micro RNA (miRNA) shuttle containing an embedded siRNA specific for a target sequence. In certain embodiments, the promoter is an inducible promoter. In certain embodiments, the vector is an adenoviral, lentiviral, adeno-associated viral (AAV), poliovirus, HSV, or murine Maloney-based viral vector. In certain embodiments, the targeted sequence is a sequence associated with a condition amenable to siRNA therapy, such as a neurodegenerative disease. An example of neurodegenerative diseases is a trinucleotide-repeat disease, such as a disease associated with polyglutamine repeats. These diseases include Huntington's disease and the spinocerebellar ataxias (SCA). Examples of SCA diseases are SCA1, SCA2, SCA3, SCA6, SCA7, or SCA17. The target sequence, in certain embodiments, is a sequence encoding ataxin-1 or huntingtin.

The present invention provides a method of preventing cytotoxic effects of neurodegenerative disease in a mammal in need thereof, by introducing the vector encoding a miRNA described herein into a cell in an amount sufficient to suppress accumulation of a protein associated with the neurodegenerative disease, and wherein the RNA prevents cytotoxic effects of neurodegenerative disease.

The present invention also provides a method to inhibit expression of a protein associated with a neurodegenerative disease in a mammal in need thereof, by introducing the vector encoding a miRNA described herein into a cell in an amount sufficient to inhibit expression of the protein associated with the neurodegenerative disease, wherein the RNA inhibits expression of the protein associated with the neurodegenerative disease. The protein associated with the neurodegenerative disease is inhibited by at least 10%, 20%, 30%, 40%, 50%, 60%, 70%, 80%, 90% 95%, or 99%.

This invention relates to compounds, compositions, and methods useful for modulating Huntington's Disease (also referred to as huntingtin, htt, or HD) gene expression using short interfering nucleic acid (siRNA) molecules. This invention also relates to compounds, compositions, and methods useful for modulating the expression and activity of other genes involved in pathways of HD gene expression and/or activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression HD genes. A siRNA molecule of the instant invention can be, e.g., chemically synthesized, expressed from a vector or enzymatically synthesized.

As used herein when a claim indicates an RNA "corresponding to" it is meant the RNA that has the same sequence as the DNA, except that uracil is substituted for thymine.

In certain embodiments of the present invention, the alleles of the targeted gene may differ by seven or fewer nucleotides (e.g., 7, 6, 5, 4, 3, 2 or 1 nucleotides). For example the alleles may differ by only one nucleotide. Examples of targeted gene transcripts include transcripts encoding a beta-glucuronidase, TorsinA, Ataxin-3, Tau, or huntingtin. The targeted genes and gene products (i.e., a transcript or protein) may be from different species of organisms, such as a mouse allele or a human allele of a target gene.

In one embodiment, the present invention further provides a method of performing gene silencing in a mammal or mammalian cell by administering to the mammal an isolated miRNA or shRNA molecule, wherein the miRNA or shRNA silences only one, or both, alleles of the targeted gene (for example the wild type and mutant alleles of HD gene) in the mammal or mammalian cell. In one example, the gene is a beta-glucuronidase gene. The alleles may be murine-specific and human-specific alleles of beta-glucuronidase. Examples of gene transcripts include an RNA transcript complementary to TorsinA, Ataxin-3, huntingtin or Tau. The targeted gene may be a gene associated with a condition amenable to siRNA therapy. For example, the condition amenable to siRNA therapy could be a disabling neurological disorder.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCA7, and SCA17), spinal and bulbar muscular atrophy (SBMA), dentatorubropallidoluysian atrophy (DRPLA). An example of a disabling neurological disorder that does not appear to result in atrophy is DYT1 dystonia. The gene of interest may encode a ligand for a chemokine involved in the migration of a cancer cell, or a chemokine receptor.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effects can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the present invention further provides a method of substantially silencing both alleles (e.g., both mutant and wild type alleles) of a target gene. In certain embodiments, the targeting of both alleles of a gene target of interest can confer a therapeutic effect by allowing a certain level of continued expression of the wild-type allele while at the same time inhibiting expression of the mutant (e.g., disease associated) allele at a level that provides a therapeutic effect. For example, a therapeutic effect can be achieved by conferring on the cell the ability to express siRNA as an expression cassette, wherein the expression cassette contains a nucleic acid encoding a small interfering RNA molecule (siRNA) targeted against both alleles, and wherein the expression of the targeted alleles are silenced at a level that inhibits, reduces, or prevents the deleterious gain of function conferred by the mutant allele, but that still allows for adequate expression of the wild type allele at a level that maintains the function of the wild type allele. Examples of such wild type and mutant alleles include without limitation those associated with polyglutamine diseases such as Huntington's Disease.

In one embodiment, the present invention further provides a method of substantially silencing a target allele while allowing expression of a wild-type allele by conferring on the cell the ability to express siRNA as an expression cassette, wherein the expression cassette contains a nucleic acid encoding a small interfering RNA molecule (siRNA) targeted against a target allele, wherein expression from the targeted allele is substantially silenced but wherein expression of the wild-type allele is not substantially silenced.

In one embodiment, the present invention provides a method of treating a dominantly inherited disease in an allele-specific manner by administering to a patient in need thereof an expression cassette, wherein the expression cassette contains a nucleic acid encoding a small interfering RNA molecule (siRNA) targeted against a target allele, wherein expression from the target allele is substantially silenced but wherein expression of the wild-type allele is not substantially silenced.

In one embodiment, the present invention provides a method of treating a dominantly inherited disease by administering to a patient in need thereof an expression cassette, wherein the expression cassette contains a nucleic acid encoding a small interfering RNA molecule (siRNA) targeted against both the mutant allele and the wild type allele of the target gene, wherein expression from the mutant allele is substantially silenced at a level that still allows for expression from the wild type allele to maintain its function in the patient.

In one embodiment, the present invention provides a method of performing gene silencing in a mammal by administering to the mammal a vector containing an expression cassette, wherein the expression cassette contains a nucleic acid encoding at least one strand of a small interfering RNA molecule (siRNA) targeted against a gene of interest, wherein the siRNA silences one or both alleles of the gene.

In one embodiment, the present invention provides a method of screening of allele-specific siRNA duplexes, involving contacting a cell containing a predetermined mutant allele with an siRNA with a known sequence, contacting a cell containing a wild-type allele with an siRNA with a known sequence, and determining if the mutant allele is substantially silenced while the wild-type allele retains substantially normal activity.

In one embodiment, the present invention provides a method of screening of specific siRNA duplexes, involving contacting a cell containing both a predetermined mutant allele and a predetermined wild-type allele with an siRNA with a known sequence, and determining if the mutant allele is substantially silenced at a level that allows the wild-type allele to retain substantially normal activity.

In one embodiment, the present invention also provides a method of screening of allele-specific siRNA duplexes involving contacting a cell containing a predetermined mutant allele and a wild-type allele with an siRNA with a known sequence, and determining if the mutant allele is substantially silenced while the wild-type allele retains substantially normal activity.

In one embodiment, the present invention also provides a method for determining the function of an allele by contacting a cell containing a predetermined allele with an siRNA with a known sequence, and determining if the function of the allele is substantially modified.

In one embodiment, the present invention further provides a method for determining the function of an allele by contacting a cell containing a predetermined mutant allele and a wild-type allele with an siRNA with a known sequence, and determining if the function of the allele is substantially modified while the wild-type allele retains substantially normal function.

In one embodiment, the invention features a method for treating or preventing Huntington's Disease in a subject or organism comprising contacting the subject or organism with a siRNA of the invention under conditions suitable to modulate the expression of the HD gene in the subject or organism whereby the treatment or prevention of Huntington's Disease can be achieved. In one embodiment, the HD gene target comprises a mutant HD allele (e.g., an allele comprising a trinucleotide (CAG) repeat expansion). In one embodiment, the HD gene target comprises both HD allele (e.g., an allele comprising a trinucleotide (CAG) repeat expansion and a wild type allele). The siRNA molecule of the invention can be expressed from vectors as described herein or otherwise known in the art to target appropriate tissues or cells in the subject or organism.

In one embodiment, the invention features a method for treating or preventing Huntington's Disease in a subject or organism comprising, contacting the subject or organism with a siRNA molecule of the invention via local administration to relevant tissues or cells, such as brain cells and tissues (e.g., basal ganglia, striatum, or cortex), for example, by administration of vectors or expression cassettes of the invention that provide siRNA molecules of the invention to relevant cells (e.g., basal ganglia, striatum, or cortex). In one embodiment, the siRNA, vector, or expression cassette is administered to the subject or organism by stereotactic or convection enhanced delivery to the brain. For example, U.S. Pat. No. 5,720,720 provides methods and devices useful for stereotactic and convection enhanced delivery of reagents to the brain. Such methods and devices can be readily used for the delivery of siRNAs, vectors, or expression cassettes of the invention to a subject or organism, and is U.S. Pat. No. 5,720,720 is incorporated by reference herein in its entirety. US Patent Application Nos. 2002/0141980; 2002/0114780; and 2002/0187127 all provide methods and devices useful for stereotactic and convection enhanced delivery of reagents that can be readily adapted for delivery of siRNAs, vectors, or expression cassettes of the invention to a subject or organism, and are incorporated by reference herein in their entirety. Particular devices that may be useful in delivering siRNAs, vectors, or expression cassettes of the invention to a subject or organism are for example described in US Patent Application No. 2004/0162255, which is incorporated by reference herein in its entirety. The siRNA molecule of the invention can be expressed from vectors as described herein or otherwise known in the art to target appropriate tissues or cells in the subject or organism.

Methods of delivery of viral vectors include, but are not limited to, intra-arterial, intra-muscular, intravenous, intranasal and oral routes. Generally, AAV virions may be introduced into cells of the CNS using either in vivo or in vitro transduction techniques. If transduced in vitro, the desired recipient cell will be removed from the subject, transduced with AAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, for in vivo delivery, AAV virions are formulated into pharmaceutical compositions and will generally be administered parenterally, e.g., by intramuscular injection directly into skeletal or cardiac muscle or by injection into the CNS.

In one embodiment, viral vectors of the invention are delivered to the CNS via convection-enhanced delivery (CED) systems that can efficiently deliver viral vectors, e.g., AAV, over large regions of a subject's brain (e.g., striatum and/or cortex). As described in detail and exemplified below, these methods are suitable for a variety of viral vectors, for instance AAV vectors carrying therapeutic genes (e.g., siRNAs).

Any convection-enhanced delivery device may be appropriate for delivery of viral vectors. In one embodiment, the device is an osmotic pump or an infusion pump. Both osmotic and infusion pumps are commercially available from a variety of suppliers, for example Alzet Corporation, Hamilton Corporation, Aiza, Inc., Palo Alto, Calif.). Typically, a viral vector is delivered via CED devices as follows. A catheter, cannula or other injection device is inserted into CNS tissue in the chosen subject. In view of the teachings herein, one of skill in the art could readily determine which general area of the CNS is an appropriate target. For example, when delivering AAV vector encoding a therapeutic gene to treat HD, the striatum is a suitable area of the brain to target. Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target. Moreover, because the methods described herein can be practiced such that relatively large areas of the brain take up the viral vectors, fewer infusion cannula are needed. Since surgical complications are related to the number of penetrations, the methods described herein also serve to reduce the side effects seen with conventional delivery techniques.

In one embodiment, pharmaceutical compositions will comprise sufficient genetic material to produce a therapeutically effective amount of the siRNA of interest, i.e., an amount sufficient to reduce or ameliorate symptoms of the disease state in question or an amount sufficient to confer the desired benefit. The pharmaceutical compositions may also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the CNS as described herein. Furthermore, it is also intended that the viral vectors delivered by the methods of the present invention be combined with other suitable compositions and therapies.

The present invention further provides an miRNA or shRNA, an expression cassette and/or a vector as described herein for use in medical treatment or diagnosis.

The present invention provides the use of an miRNA or shRNA, an expression cassette and/or a vector as described herein to prepare a medicament useful for treating a condition amenable to RNAi in an animal, e.g., useful for treating Huntington's Disease.

The present invention also provides a nucleic acid, expression cassette, vector, or composition of the invention for use in therapy.

The present invention also provides a nucleic acid, expression cassette, vector, or composition of the invention for treating, e.g., for use in the prophylactic or therapeutic treatment of, a neurodegenerative disease.

BRIEF DESCRIPTION OF THE FIGURES

FIG. 1 depicts modified human mir-30 containing sequences specific for several genes of interest. Mir-30 (SEQ ID NO:1), miSCA1 (SEQ ID NO:2), shSCA1 (SEQ ID NO:3), miJNK (SEQ ID NO:4), and miHTT (SEQ ID NO:5).

FIGS. 4A-4C. Disparate strand-biasing confounds shRNA and artificial miRNA comparisons. (FIG. 4A) Small transcript northern blot performed at 48 h post-transfection of HD2.1 RNAi expression plasmids in HEK293 cells shows improved yield of processed antisense RNA (AS) from CMV-driven artificial miRNA variants 1 and 2 (miV1, miV2) relative to the U6-driven first-generation shHD2.1. Pre-designates the precursor stem-loop. (FIG. 4B) Q-PCR analysis for endogenous HD mRNA levels performed 48 h after transfection of HD2.1 RNAi expression plasmids into HEK293 cells. Results were normalized to GAPDH mRNA levels and are shown as mean±S.E.M relative to mock-treated samples (n=3, *=P<0.05). (FIG. 4C) Strand-biasing of U6-driven HD2.1 RNAi vectors. Strand-biasing was assessed by measuring luciferase activity from reporters containing either sense (intended; binds RNAi antisense) or antisense (unintended; binds RNAi sense) target sequences in the 3'UTR (FIG. 18C). RNAi reporter and RNAi expression plasmids were co-transfected into HEK293 cells, and Dual-Glo® Luciferase assays were performed at 24 h. Results are shown as mean±S.E.M (n=4) relative to mock-treated controls and demonstrate that shHD2.1 preferentially loads the unintended siRNA strand while miHD2.1 more often loads the intended strand.

FIGS. 6A-6C. A. shRNA variants were generated to assess the effects of 5' or 3' modifications. B. Processing was observed by small transcript northern blot 48 h post-transfection of shRNA-expression plasmids. C. Silencing of co-transfected artificial luciferase target 24 h following transfection.

FIGS. 7A-7B. A. Small transcript northern performed 48 h post-transfection of eGFP RNAi in 293 cells. Probe: eGFP sense oligonucleotide. B. eGFP RNAi vs. siChk2-eGFP Target(6:1). Dual-Glo® luciferase assay was performed 24 h post-transfection of RNAi:Target plasmids in 293 cells. Shown relative to mock RNAi.

FIGS. 9A and 9B. Results of studies on the safety of RNAi vectors. FIG. 9A shows a Spike Safety Study, and FIG. 9B shows a gene silencing study.

FIG. 11. In vivo safety of RNAi vectors in muscle. miReporter and GFP:U6.RNAi (shRNA:Left or miRNA:Right) plasmids were co-electroporated into the tibialis anterior of the animals. IVIS Imaging for Firefly or Renilla Luciferase and GFP was examined.

FIGS. 12A-12B. A. siCheck2 miReporters (containing a perfect miRNA target site located in the 3'UTR of Firefly Luciferase) were electroporated into the tibialis anterior muscle. IVIS imaging was performed 48 later to measure the amount of Firefly luciferase activity. Results confirm the use of miReporters in vivo. miR-1 siCheck2 reporter was used in subsequent experiments. B. pGFP:U6.RNAi and siCheck2 miR-1 reporter expression plasmids were co-electroporated at varying doses (Lo=1 μg RNAi: 1 μg miReporter and Hi=10 μg RNAi: 1 μg miReporter) into the tibialis anterior muscle. shRNAs were delivered to the left leg and miRNAs to the right leg. IVIS imaging was performed at various time-points to measure Firefly luciferase activity.

FIG. 16. Vector sequences are depicted in this Figure. Transcription start sites are bold and underlined. Restriction enzymes used in the cloning process are indicated. The underlined sequences within "Oligos" represent the annealing portion. Predicted miRNA and shRNA structures are based on mFOLD analysis. Arrows indicate the major Drosha (left) and Dicer (right) cleavage sites.

FIGS. 18A-18E. Optimization of the human miR-30 shuttle. (FIG. 18A) General structures of shRNAs and artificial miRNAs (Ns correspond to the siRNA-duplex region with sense and antisense being 5' and 3' respectively). Here, the antisense sequences are designed to target SCA1, HD or GFP transcripts. Hash marks indicate the known major Drosha and Dicer cleavage sites of human miR-30. Processing sites of many shRNAs are unknown and vary based on the presence of short flanking sequences. *, boxed sequence is for orientation purposes in the panel. (FIG. 18B) Artificial miRNA variants were generated by altering the nearby flanking sequences, and portions of the predicted mFOLD structures within the stem-base are shown. Instability (i.e. single-stranded nature) within the grey-shaded region promotes Drosha binding and cleavage. These variants contain identical RNAi sequences and structures in regions above the grey-shaded box. (FIG. 18C) Cartoon depicting RNAi reporters, generated by inserting target sequences into the 3'UTR of Renilla luciferase. Reporter plasmids also contain a Firefly luciferase expression cassette for normalization. (FIG. 18D) Silencing activity of miR-30 variants. Artificial miSCA1 variants and RNAi reporter expression plasmids were co-transfected into HEK293 cells, and Dual-Glo® Luciferase assays were performed after 24 h. Results of two independent experiments (each n=3) are shown relative to mock-treated (i.e., promoter only) controls and demonstrate that variant 2 (miV2) is the most effective artificial miRNA (even more effective than human miR-30, **=P<0.01). (FIG. 18E) Small transcript northern blot was performed at 48 h post-transfection of miRNA variant expression plasmids into HEK293 cells. Results show that miV2 yields more mature antisense RNA (SCA1 AS) compared to the other artificial miRNA variants including the natural miR-30 shuttle.

FIG. 19 provides additional miRNA sequences that were used to target either HD or SCA1. These are the predicted RNA stem loop structures that contain the active RNAi sequences. The active antisense strand of the embedded siRNA sequence is underlined.

FIGS. 20A-20F provide an illustration of miRNA shuttles of the present invention. FIG. 20A depicts a primary miRNA transcript (pri-miRNA) with the segments shown in 5' to 3' configuration. FIGS. 20B and 20C depict in further detail of alternative 5'-Flanking Regions with the segments shown in 5' to 3' configuration (light grey region with italics text shown in FIG. 20A is expanded in FIGS. 20B and 20C). FIGS. 20D and 20E depict in further detail alternative 3'-Flanking Regions with the segments shown in 5' to 3' configuration (dark grey region with bold text shown in FIG. 20A is expanded in FIGS. 20D and 20E). FIG. 20F provides an exemplary artificial miRNA molecule.

(FIG. 21A) Diagrams depicting the various 5' and 3' overhangs tested on identical shRNA stem-loops. (FIG. 21B) Plasmids expressing the shRNA variants were transfected into HEK293 cells, and small transcript northern blot [probing for antisense (AS) or sense (S) sequences] with densitometry analysis (values below blots) was performed 48 h later to assess shRNA processing efficiency (n=3). Results show that 5' overhang variants yield less precursor (Pre-) and antisense (AS) RNAs compared to the optimized shRNAs with $U_{2-4}$ 3' overhangs derived from Pol-III transcription termination. Appropriate strand-loading was observed for each shRNA variant (i.e., AS:Pre->S:Pre-). (FIG. 21C and FIG. 21D) Silencing of intended (left bar graph, FIG. 21C) or unintended (right bar graph, FIG. 21D) target strands was assessed by co-transfection of shRNA-variant and RNAi luciferase reporter expression plasmids into HEK293 cells, and Dual Glo® Luciferase assays were performed at 24 h. Results are shown as mean±S.D. (n=3) relative to mock-treated controls and confirm that sub-optimal overhangs decrease silencing efficiency. Notably, each shRNA preferentially silenced the intended target (transfected at 1:20 RNAi:Target) relative to the unintended target (transfected at 3:1 RNAi:Target).

FIGS. 23A-23C. Comparable shRNA- and miRNA-based vectors exhibit appropriate strand-biasing. (FIGS. 23A-C) Strand-biasing of SCA1, GFP, and HD RNAi vectors respectively. Strand-biasing was assessed using luciferase reporters containing either sense (intended) or antisense (unintended) target sequences. RNAi luciferase reporter and RNAi expression plasmids were co-transfected into HEK293 cells, and Dual-Glo® Luciferase assays were performed at 24 h. Results of duplicate experiments (each n=3) are shown as mean±S.E.M relative to mock-treated controls and demonstrate that the artificial miRNA and shRNA vectors exhibit appropriate strand-biasing.

FIGS. 24A-24E. shRNAs are more potent than artificial miRNAs in vitro. (FIG. 24A) RNAi and RNAi luciferase reporter plasmids were co-transfected into HEK293 cells to assess gene silencing. Dual Glo® Luciferase assays were performed at 24 h and results, shown as mean±S.E.M relative to mock-treated controls, were compiled from several experiments (4 GFP, 4 SCA1 and 2 HD; each n=3). Dose is indicated as RNAi:Target. P<0.001 and P<0.05 for 1:1 and 3:1 doses respectively. (FIGS. 24B, 24C) Plasmids expressing RNAi targeting endogenous SCA1 or HD were transfected into HEK293 cells, and Q-PCR analysis was performed at 48 h to measure reduction of endogenous transcripts. SCA1 and HD mRNA levels were normalized to GAPDH or 18S rRNA and are shown as mean±S.E.M (n≧3, *=P<0.05, *=P<0.001) relative to mock-treated controls. (FIG. 24D) GFP RNAi and eGFP expression plasmids were co-transfected into HEK293 cells, and fluorescence levels were evaluated 48 h later. Results are shown as mean±S.E.M (n=4, =P<0.01) relative to SCA1 RNAi-treated controls. (FIG. 24E) shRNA and artificial miRNA expression plasmids were transfected into HEK293 cells, and small transcript northern blot was performed at 48 h to assess RNAi expression and processing (Pre-=precursor, AS=antisense RNA). Results show that shRNAs yield more than 4-fold mature antisense RNA, relative to artificial miRNAs, independent of RNAi target sequence. These results were consistent among triplicate blots for each RNAi vector-pair.

(FIG. 26A) CMV- or U6-driven artificial miRNA vectors targeting SCA1 were transfected into HEK293 cells, and small transcript northern blot was performed at 48 h to assess RNAi expression and processing (AS=antisense siRNA). (FIG. 26B) RNAi and RNAi luciferase reporter plasmids were co-transfected into HEK293 cells to assess gene silencing. Dual Glo® Luciferase assays were performed at 24 h and results, shown as mean±S.E.M relative to mock-treated controls, were compiled from several experiments (3 SCA1, 3 GFP; each n=3). Dose is indicated as RNAi:Target and P<0.01 within each dose.

FIG. 27. Mapping cleavage sites for corresponding shRNA and artificial miRNA vectors. HEK293 cells were transfected with shSCA1 or miSCA1 expression plasmids and 3'-RACE was performed on RNA harvested 48 h later to identify the 3' ends of antisense (AS) or sense (S) SCA1 small RNAs derived from these vectors. For each vector, the 10-12 analyzed sequences per strand are shown. Notably, each represented sequence is present in both shSCA1- or miSCA1-treated samples, and the most prevalent species (shaded grey box) was shared. Lowercase nucleotides indicate bases that were ambiguous due to the use of an anchored oligo-dT primer during first-strand cDNA synthesis. FIG. 27 includes SEQ ID NOs:84-135.

FIG. 28. Artificial miRNA cloning strategy. Overlapping DNA oligonucleotides are designed to generate a basic miR-30 stem-loop containing siRNA sense and antisense sequences along with the necessary elements within the stem-base known to direct efficient Drosha cleavage. Oligonucleotides are annealed and extended with DNA polymerase to generate the dsDNA encoding the artificial miRNA flanked by restriction enzyme sites. This cassette is digested and cloned to expression vectors which provide additional flanking sequences that can influence the processing efficiency. "Term." refers to the transcription terminator (e.g., polyA signal or 6T's for CMV and U6 promoters (shown as arrow) respectively).

FIG. 29. Comparison of an exemplary shRNA (SEQ ID NO: 136) and miRNA (SEQ ID NO:137) that produce an equivalent siRNA molecule (SEQ ID NOs:138-139).

FIG. 30A shows that shSCA1 significantly decreased the function of miGFP. FIG. 30B shows that miSCA1 demonstrated similar silencing efficacy as a low dose of shSCA1 when targeting the SCA1 RNAi luciferase report. FIGS. 30C, 30D show reciprocal experiments where the effect of GFP RNAi competitors (shGFP or miGFP) on miSCA1 activity was evaluated in parallel with GFP RNAi efficacy. FIG. 30E shows that miGFP biogenesis was severely disrupted in the presence of shSCA1 expression vectors at low and high doses.

FIGS. 31A, 31B show the measurement of the activity of a luciferase reporter for miR-1 function in undifferentiated and differentiated C2C12 cells. FIG. 31C shows measurements of the elongation of differentiated C2C12 cells following transfection with shRNA or artificial miRNA expression plasmids that co-express CMV-driver hrGFP. FIG. 31D shows the relative lengths of MHC+GFP+ cells. FIG. 31E shows that the elongation process was significantly reduced in C2C12 cells transfected with shSCA1-expressing plasmids, nut not those expressing miSCA1.

FIG. 34. shRNAs targeting sequences across the huntingtin gene. shRNA sequences are named for the targeted exon. For example, sh1.10 targets exon 1, and it was the $10^{th}$ shRNA designed. Intervening numbers (e.g., sh1.5) targeted sequences between 1.4 and 1.8, but were specific to human sequences only. Functionality was determined by QPCR and protein dot blot performed 48 h post-transfection into HEK 293 cells. Three lead sequences (bold italics) were chosen for in vivo analysis in CAG140 knock in mice based on consistent and differential gene silencing in cell culture screens. sh2.1 was identified during a prior screen and shown to be efficacious in a mouse model of HD. It targets only human huntingtin.

(FIG. 35A) Thirty-five shRNAs (bars above cartoon) targeting conserved sequences (FIG. 34) spanning human Huntington's disease (HD) and mouse Huntington's Disease homolog (HDh) mRNAs were generated with consideration for sequences that promote proper loading of the antisense strands into the RISC. Plasmids expressing U6-driven shRNAs were transfected into HEK293 cells and HD gene silencing was evaluated by QPCR and protein dot blot analyses 48 h post-transfection. (FIG. 35B) Three candidate shRNAs targeting sequences in exons 2 (sh2.4, SEQ ID NO:175), 8 (sh8.2, SEQ ID NO:176) and 30 (sh30.1, SEQ ID NO:177) were chosen for further study. (FIG. 35C) shRNA expression plasmids were transfected into mouse C2C12 cells, and endogenous huntingtin protein levels were evaluated by western blot analyses 48 h post-transfection. Mismatch (mis) controls contain 4 base pair changes that render the shRNAs ineffective. Beta-catenin serves as the loading control.

FIG. 36A is a diagram of the recombinant AAV2/1 viral vectors containing shRNA and hrGFP expression cassettes. FIG. 36B shows photomicrographs represent the rostral-to-caudal distribution of hrGFP-positive cells in mouse brain following direct injection of virus into the striatum. Scale bar=500 μm. (36C) QPCR analysis measuring HDh mRNA levels in shRNA-treated mouse striata demonstrates similar silencing efficacies among sh2.4, sh8.2 and sh30.1. Mice were injected into the striatum with AAVsh2.4-GFP, AAVsh8.2-GFP, AAVsh30.1-GFP or AAV-GFP and RNA was harvested 4 months later. Immunohistochemistry revealed that sh2.4 and sh30.1 induce striatal toxicity in mice (FIG. 36D). Mice were injected with the indicated AAVshRNA-GFP or AAV-GFP into the striatum, and histological analyses were performed on brains harvested at 4 months post-treatment. Representative photomicrographs for immunohistochemical staining of DARPP-32-positive neurons (top panel, scale bar=500 um) and IbaI-positive microglia (bottom panel, scale bar=100 um) are shown for each treatment group.

FIGS. 38A-38B. The non-toxic sh8.2 generates lower levels of processed antisense RNA. (FIG. 38A) Small transcript northern blot was performed to assess antisense RNA levels present in mouse striata treated with the indicated AAVshRNA-GFP. Left lanes: 2 separately treated striatal tissue samples. Center and right lanes: positive controls loaded as standards [10-fold dilutions for both sense (center) or antisense (right) strands]. (FIG. 38B) Densitometry analysis was used to quantify the relative levels of HD antisense (AS) RNAs. Signals were quantified using Image J Software and expression is shown as femtomoles/microgram total RNA.

FIGS. 39A-39D. Artificial miRNAs mitigate striatal toxicity in mice. QPCR analyses were performed to measure mouse HDh (FIG. 39A) and CD11b (FIG. 39B) mRNA levels in AAV-RNAi-injected striata harvested 4 months post-treatment (NS=not significant). Results, shown relative to uninjected striata, demonstrate that mi2.4 silences HD transcripts as effectively as sh2.4, but avoids induction of CD11b, a marker for microglial activation. (FIG. 39C) Small transcript northern blot analysis for mature HD2.4 antisense (AS) RNAs present in AAV-RNAi-treated striatal lysates reveals a robust disparity between the levels generated from sh2.4 and mi2.4 vectors. Ethidium bromide (EtBr) staining is shown as the loading control. (FIG. 39D) Histological analyses demonstrate the improved safety profile of mi2.4. Mice were injected with the indicated AAV-RNAi-GFP viruses into the striatum and histological analyses were performed on brains harvested at 4 months post-treatment. Photomicrographs representing hrGFP (top panel) and immunohistochemical staining of DARPP-32-positive neurons (middle panel) and IbaI-positive microglia (bottom panel) are shown for each treatment group. Scale bar=500 μm.

FIGS. 40A-40C. Artificial miRNAs naturally reduce precursor and mature inhibitory RNAs. (40A) Sequences and comparison of sh2.4 and mi2.4 containing the core HD2.4 sequence (shaded boxes). Each transcript starts with the +1-G nucleotide natural to the U6 promoter. The major Drosha and Dicer cleavage sites are shown by hash marks. (40B) HEK 293 cells were transfected with HD2.4 RNAi expression plasmids at the indicated amounts, and small transcript northern blot was performed 48 h later. Results demonstrate that sh2.4 generates abundant levels of unprocessed precursor (Pre-) and processed antisense RNAs (2.4AS), even at a 10-fold lower dose, relative to mi2.4. Ethidium bromide (EtBr) staining is shown as the loading control. (40C) HD 2.4 RNAi expression plasmids were transfected into HEK 293 cells, and QPCR analysis was performed 48 h later to measure endogenous HD mRNA levels. Results demonstrate that mi2.4 silences HD transcripts efficiently, relative to sh2.4, despite being expressed at considerably lower levels.

FIGS. 42A-42B. Targeting mutant huntingtin. FIG. 42A provides a schematic representation of the huntingtin (htt) gene. The intron sequences are the lightest bands, and the exon sequences are the second lightest bands. The expanded CAG sequence (dark band) is localized in the first exon of the Htt gene. FIG. 42B provides siRNA walking 5' and 3'. Sequences of short interfering RNA (siRNA) targeting 5' and 3' of the CAG-repeat region were generated to preferentially target the mutant huntingtin allele.

FIGS. 44A-44C. shows Western blots and Q-PCR results for candidate siRNA sequences. FIG. 44A shows wild type Htt and FIG. 44B shows mutant Htt. As seen in FIG. 44C, siRNA sequence number 7 (S7) reduced mutant htt by 40% and the wild type huntingtin by 6%.

FIG. 46A shows normal Htt, and FIG. 46B shows mutant Htt.

DETAILED DESCRIPTION OF THE INVENTION

Figure 2:
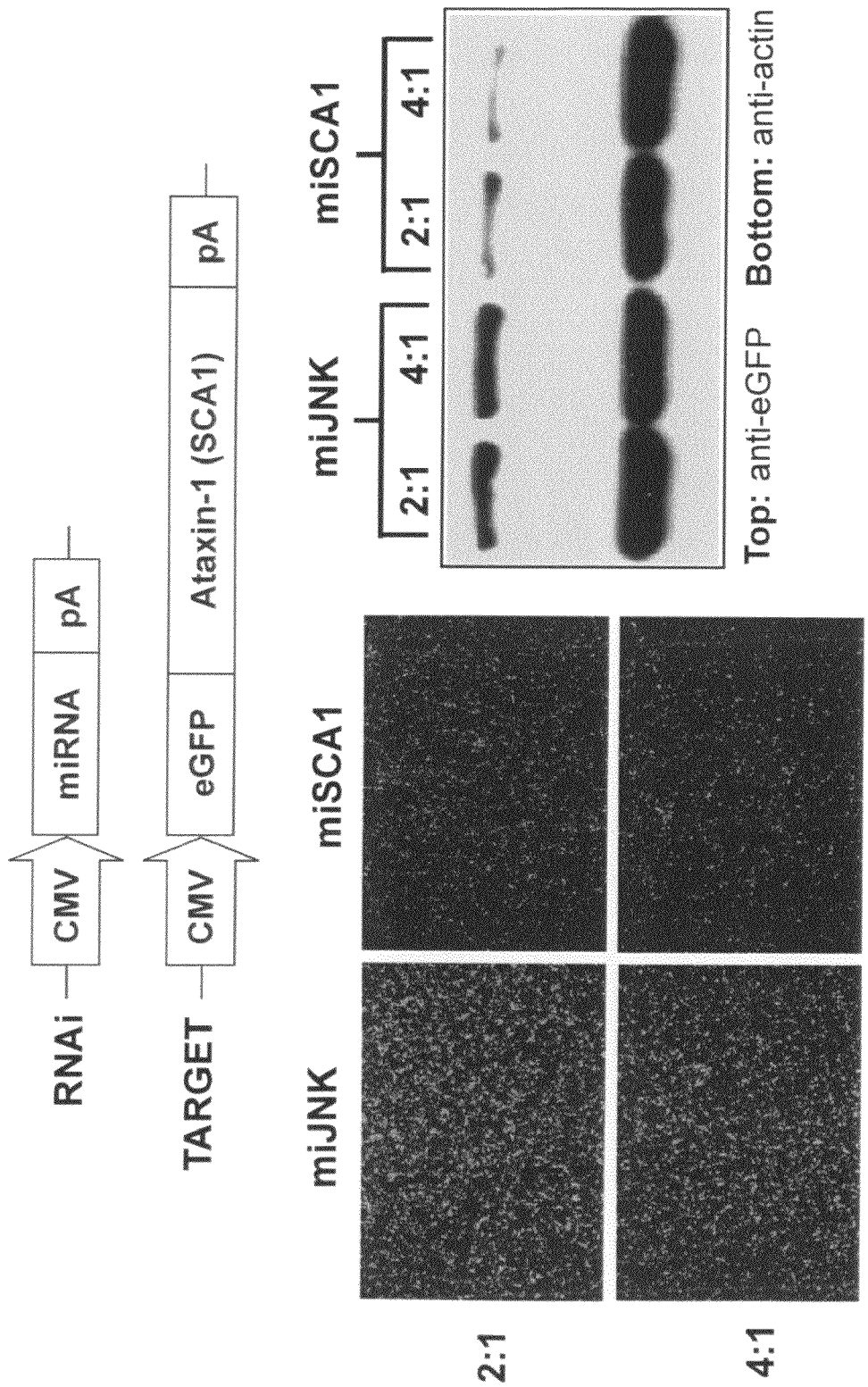
FIG. 2. The target gene (in this case Ataxin-1, also called SCA1) was cloned, and the SCA1 miRNA was also generated.

RNA interference (RNAi) provides a promising approach for the treatment of several human diseases. However, the safety of expressed vector based RNAi-based therapies remains a concern. Safety concerns for vector expressed RNAi therapies arise as a result of off target toxicity.

The use of RNAi as a therapeutic is dependant upon the elucidation of several factors including i) the delivery and persistence of the RNAi construct for effective silencing of the target gene sequence; ii) the design of the siRNA in order to achieve effective knock down or gene suppression of the target sequence, and iii) the optimal siRNA expression system (shRNA or miRNA) for delivery of the therapeutic siRNA. While many studies have evaluated the use of RNAi delivered as chemically synthesized oligonucleotide structures, for many clinical conditions and disease states such as Huntington's Disease, it is believed that to achieve therapeutic benefit there is a need for long term and or persistent high level expression of the therapeutic siRNA as achieved by endogenous production of expressed siRNA. To date, shRNA- and artificial miRNA-based strategies have been compared with conflicting results (Boden et al., 2004, *Nucleic Acids Res* 32: 1154-1158; Silva et al., 2005, *Nat Genet.* 37: 1281-1288; Li et al., 2007, *RNA* 13: 1765-1774). The therapeutic utility of expressed RNAi is unresolved due to safety concerns as a result of off target toxicity arising from cellular responses to dsRNA (IFN-b, PKR, OAS1), saturation of RNAi machinery or silencing of off targets via partial complementarity with unintended mRNAs. Thus, there is an on-going need for optimizing expressed RNAi vectors that are safe and effective.

shRNAs are comprised of stem-loop structures which are designed to contain a 5' flanking region, siRNA region segments, a loop region, a 3' siRNA region and a 3' flanking region. Most RNAi expression strategies have utilized short-hairpin RNAs (shRNAs) driven by strong polIII-based promoters. Many shRNAs have demonstrated effective knock down of the target sequences in vitro as well as in vivo, however, some shRNAs which demonstrated effective knock down of the target gene were also found to have toxicity in vivo. A recently discovered alternative approach is the use of artificial miRNAs (pri-miRNA scaffolds shuttling siRNA sequences) as RNAi vectors. Artificial miRNAs more naturally resemble endogenous RNAi substrates and are more amenable to Pol-II transcription (e.g., allowing tissue-specific expression of RNAi) and polycistronic strategies (e.g., allowing delivery of multiple siRNA sequences). To date the efficacy of miRNA based vector systems compared to shRNA has been confounded by conflicting results. Importantly, the question of off-target toxicity produced by the two systems has not been evaluated.

An important consideration for development of expressed siRNA is the concept of "dosing" the host cell with the expressed siRNA construct. "Dosing" for an expressed siRNA in the context of the present invention refers to and can be dependant on the delivery vehicle (e.g., viral or nonviral), the relative amounts or concentration of the delivery vehicle, and the strength and specificity of the promoter utilized to drive the expression of the siRNA sequence. In the present application the inventors have directly compared the efficacy and off-target toxicity of the expressed RNAi vectors under conditions where the shRNAs and miRNAs were delivered at equivalent dose by an AAV vector.

The inventors have developed artificial miRNA shuttle vectors that incorporate the stem loop sequences contained in shRNAs within modifications of a naturally occurring human microRNA 30 sequence or mi30 sequence that serve to shuttle these small interfering RNA (siRNA) sequences. Unlike previously published reports, these miRNA shuttles were subsequently compared to optimized shRNA constructs. The shRNA constructs were optimized to contain sequences with the weakest base pairing near the 5' end of the antisense or guide when compared to the sense or non-guide strand in order to allow for efficient processing and loading of the antisense into the RNAi-induced silencing complex (RISC). These optimized siRNAs were then compared to the artificial miRNA shuttle vectors containing the identical target sequences. The inventors found that optimized shRNAs, independent of siRNA sequence and target sequence, generate more processed siRNAs and are more efficient at mediating gene silencing. However, northern blot analysis showed an overabundance of unprocessed shRNAs as well as mature antisense RNA molecules, whereas processing of the miRNA shuttles was highly efficient. The inventors hypothesized that the unprocessed shRNAs may arise due to saturation of the RNAi machinery and may result in additional safety concerns due to off-target toxicity. In addition, while certain shRNAs were demonstrated to be potent gene silencers as a result of overabundant or overexpression of shRNAs, they were also overly toxic when delivered in vivo to brains. An approach to reduce toxicity evaluated by the inventors was to lower the dose of the shRNA delivered by lowering the viral titer injected, thereby decreasing the copy number of the siRNA in the transduced cell, resulting in lower expression of the siRNA. However, lowering the dose in terms of viral titer did not reduce off-target toxicity in the brain until the dose was lowered to levels that were not effective in target gene silencing.

The inventors evaluated whether generation of artificial miRNAs would reduce off target toxicity, thereby improving the relative safety of siRNA as a potential therapeutic. The inventors evaluated off target toxicity of shRNA and miRNA vectors on the processing and function of artificial miRNAs designed to mimic endogenous stem loops. Northern blot analysis showed that shRNAs markedly inhibited processing of artificial miRNAs, while miRNA shuttles had relatively no effect even at much higher doses. Similarly, shRNAs at low doses drastically reduced silencing mediated by artificial miRNAs, whereas miRNA shuttles at high doses only caused slight inhibition. Notably, silencing efficacies of miRNA shuttles (high dose) and shRNAs (low dose) were indistinguishable. These results suggest that shRNA-based vectors saturate cellular RNAi machinery substantially more than miRNA shuttles. Surprisingly, sequences that were found to have off-target toxicity in vivo in the context of a shRNA vector, when placed into the artificial miRNA vector of the present invention, demonstrated attenuated off-target toxicity yet retained effective target gene silencing. Hence, the miRNA shuttle vector of the present invention provides a safer approach to deliver therapeutic RNAi in vivo.

MicroRNA Shuttles for RNAi miRNAs are small cellular RNAs (~22 nt) that are processed from precursor stem loop transcripts. Known miRNA stem loops can be modified to contain RNAi sequences specific for genes of interest. miRNA molecules can be preferable over shRNA molecules because miRNAs are endogenously expressed. Therefore, miRNA molecules are unlikely to induce dsRNA-responsive interferon pathways, they are processed more efficiently than shRNAs, and they have been shown to silence 80% more effectively.

Also, the promoter roles are different for miRNA molecules as compared to shRNA molecules. Tissue-specific, inducible expression of shRNAs involves truncation of polII promoters to the transcription start site. In contrast, miRNAs can be expressed from any polII promoter because the transcription start and stop sites can be relatively arbitrary.

Treatment of Diseases

The dominant polyglutamine expansion diseases, which include Spinocerebellar ataxia type 1 (SCA1) and Huntington's disease (HD), are progressive, untreatable neurodegenerative disorders. In inducible mouse models of SCA1 and HD, repression of mutant allele expression improves disease phenotypes. Thus, therapies designed to inhibit disease gene expression would be beneficial. In studies presented herein, the ability of RNA interference (RNAi) to inhibit polyglutamine-induced neurodegeneration caused by mutant ataxin-1 was evaluated in a mouse model of SCA1. Upon intracerebellar injection, recombinant AAV vectors expressing shRNAs profoundly improved motor coordination, restored cerebellar morphology, and resolved characteristic ataxin-1 inclusions in Purkinje cells of SCA1 mice. The present invention thus provides methods of using RNAi in vivo to treat dominant neurodegenerative diseases. "Treating" as used herein refers to ameliorating at least one symptom of, curing and/or preventing the development of a disease or a condition.

In certain embodiment of the invention, siRNAs are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when siRNA initiates the degradation of the mRNA transcribed from a gene of interest in a sequence-specific manner via RNA interference, thereby preventing translation of the gene's product.

The reference to siRNAs herein is meant to include shRNAs and other small RNAs that can or are capable of modulating the expression of a targeted gene, e.g., the HD gene, for example via RNA interference. Such small RNAs include without limitation, shRNAs and microRNAs (miRNAs).

Disclosed herein is a strategy that results in substantial silencing of targeted alleles via siRNA. Use of this strategy results in markedly diminished in vitro and in vivo expression of targeted alleles. This strategy is useful in reducing expression of targeted alleles in order to model biological processes or to provide therapy for human diseases. For example, this strategy can be applied to a major class of neurodegenerative disorders, the polyglutamine diseases, as is demonstrated by the reduction of polyglutamine aggregation in cells following application of the strategy. As used herein the term "substantial silencing" means that the mRNA of the targeted allele is inhibited and/or degraded by the presence of the introduced siRNA, such that expression of the targeted allele is reduced by about 10% to 100% as compared to the level of expression seen when the siRNA is not present. Generally, when an allele is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of an allele when an siRNA has not been introduced to a cell.

Dominantly inherited diseases, including polyQ neurodegenerative disorders, are ideal candidates for siRNA-based therapy. The polyQ neurodegenerative disorders include at least nine inherited disorders caused by CAG repeat expansions that encode polyQ in the disease protein. PolyQ expansion confers a dominant toxic property on the mutant protein that is associated with aberrant accumulation of the disease protein in neurons. PolyQ diseases are progressive, ultimately fatal disorders that typically begin in adulthood. Huntington disease (HD) is the best known polyQ disease, but at least seven hereditary ataxias and one motor neuron disease are also due to CAG repeat/polyQ expansion. Although the clinical features and patterns of neuronal degeneration differ among the diseases, increasing evidence suggests that polyQ diseases share important pathogenic features. In particular, expansion of the CAG repeat/polyQ domain confers upon the encoded protein a dominant toxic property. Thus, as a therapeutic strategy, efforts to lower expression of the mutant gene product prior to cell death could be highly beneficial to patients.

The polyQ neurodegenerative disorders include at least nine diseases caused by CAG repeat expansions that encode polyQ in the disease protein. PolyQ expansion confers a dominant toxic property on the mutant protein that is associated with aberrant accumulation of the disease protein in neurons. In FTDP-17, Tau mutations lead to the formation of neurofibrillary tangles accompanied by neuronal dysfunction and degeneration. The precise mechanisms by which these mutant proteins cause neuronal injury are unknown, but considerable evidence suggests that the abnormal proteins themselves initiate the pathogenic process. Accordingly, eliminating expression of the mutant protein by siRNA or other means slows or prevents disease. However, because many dominant disease genes also encode essential proteins siRNA-mediated approaches were developed that selectively inactivate mutant alleles, while allowing continued expression of the wild type proteins ataxin-3 and huntingtin.

I. RNA Interference (RNAi) Molecules

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest, for example, ataxin-1 or huntingtin (htt). As used herein, the term "siRNA" is a generic term that encompasses the subset of shRNAs and miRNAs. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding ataxin-1 or huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional siRNAs. "Artificial miRNA" or an "artificial miRNA shuttle vector", as used herein interchangably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (~35 nucleotides upstream and ~40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

"Off-target toxicity" refers to deleterious, undesirable, or unintended phenotypic changes of a host cell that expresses or contains an siRNA. Off-target toxicity may result in loss of desirable function, gain of non-desirable function, or even death at the cellular or organismal level. Off-target toxicity may occur immediately upon expression of the siRNA or may occur gradually over time. Off-target toxicity may occur as a direct result of the expression siRNA or may occur as a result of induction of host immune response to the cell expressing the siRNA. Without wishing to be bound by theory, off-target toxicity is postulated to arise from high levels or overabundance of RNAi substrates within the cell. These overabundant or overexpressed RNAi substrates, including without limitation pre- or pri RNAi substrates as well as overabundant mature antisense-RNAs, may compete for endogenous RNAi machinery, thus disrupting natural miRNA biogenesis and function. Off-target toxicity may also arise from an increased likelihood of silencing of unintended mRNAs (i.e., off-target) due to partial complementarity of the sequence. Off target toxicity may also occur from improper strand biasing of a non-guide region such that there is preferential loading of the non-guide region over the targeted or guide region of the RNAi. Off-target toxicity may also arise from stimulation of cellular responses to dsRNAs which include dsRNA (IFN-b, PKR, OAS1). "Decreased off target toxicity" refers to a decrease, reduction, abrogation or attenuation in off target toxicity such that the therapeutic effect is more beneficial to the host than the toxicity is limiting or detrimental as measured by an improved duration or quality of life or an improved sign or symptom of a disease or condition being targeted by the siRNA. "Limited off target toxicity" or "low off target toxicity" is used to refer to an unintended undesirable phenotypic changes to a cell or organism, whether detectable or not, that does not preclude or outweigh or limit the therapeutic benefit to the host treated with the siRNA and may be considered a "side effect" of the therapy. Decreased or limited off target toxicity may be determined or inferred by comparing the in vitro analysis such as Northern blot or QPCR for the levels of siRNA substrates or the in vivo effects comparing an equivalent shRNA vector to the miRNA shuttle vector of the present invention.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where siRNA molecules have not been administered). Knock-down of gene expression can be directed by the use of dsRNAs or siRNAs.

"RNA interference (RNAi)" is the process of sequence-specific, post-transcriptional gene silencing initiated by siRNA. During RNAi, siRNA induces degradation of target mRNA with consequent sequence-specific inhibition of gene expression.

According to a method of the present invention, the expression of huntingtin or atxain-1 can be modified via RNAi. For example, the accumulation of huntingtin or atxain-1 can be suppressed in a cell. The term "suppressing" refers to the diminution, reduction or elimination in the number or amount of transcripts present in a particular cell. For example, the accumulation of mRNA encoding huntingtin or atxain-1 can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

A mutant protein refers to the protein encoded by a gene having a mutation, e.g., a missense or nonsense mutation in one or both alleles of huntingtin or atxain-1. A mutant huntingtin or atxain-1 may be disease-causing, i.e., may lead to a disease associated with the presence of huntingtin or atxain-1 in an animal having either one or two mutant allele(s).

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid nucleic acid molecules and compositions containing those molecules. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

A "foreign" gene refers to a gene not normally found in the host organism that has been introduced by gene transfer.

The terms "protein," "peptide" and "polypeptide" are used interchangeably herein.

"Conservatively modified variations" of a particular nucleic acid sequence refer to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell (2001).

The terms "heterologous gene", "heterologous DNA sequence", "exogenous DNA sequence", "heterologous RNA sequence", "exogenous RNA sequence" or "heterologous nucleic acid" each refer to a sequence that either originates from a source foreign to the particular host cell, or is from the same source but is modified from its original or native form. Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "open reading frame" (ORF) refers to the sequence between translation initiation and termination codons of a coding sequence. The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

"cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted herein, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted herein, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation of Meinkoth and Wahl (1984); Tm 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Very stringent conditions are selected to be equal to the Tm for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

II. Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. The RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a method for preparing substitution variants. This technique is known in the art. Briefly, nucleic acid encoding a siRNA can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding siRNA. The oligonucleotides are readily synthesized using techniques known in the art.

The DNA template can be generated by those vectors that are either derived from bacteriophage M13 vectors (the commercially available M13 mp18 and M13 mp19 vectors are suitable), or those vectors that contain a single-stranded phage origin of replication. Thus, the DNA that is to be mutated may be inserted into one of these vectors to generate single-stranded template. Production of the single-stranded template is described in Chapter 3 of Sambrook and Russell, 2001. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the DNA, and the other strand (the original template) encodes the native, unaltered sequence of the DNA. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described herein. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(*S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(*S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

III. Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed herein, a "transfected", or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

IV. Methods for Introducing the Expression Cassettes of the Invention into Cells The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene, and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

V. Delivery Vehicles for the Expression Cassettes of the Invention

Delivery of compounds into tissues and across the blood-brain barrier can be limited by the size and biochemical properties of the compounds. Currently, efficient delivery of compounds into cells in vivo can be achieved only when the molecules are small (usually less than 600 Daltons). Gene transfer for the correction of inborn errors of metabolism and neurodegenerative diseases of the central nervous system (CNS), and for the treatment of cancer has been accomplished with recombinant adenoviral vectors.

The selection and optimization of a particular expression vector for expressing a specific siRNA in a cell can be accomplished by obtaining the nucleic acid sequence of the siRNA, possibly with one or more appropriate control regions (e.g., promoter, insertion sequence); preparing a vector construct comprising the vector into which is inserted the nucleic acid sequence encoding the siRNA; transfecting or transducing cultured cells in vitro with the vector construct; and determining whether the siRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the siRNA into the host cell genome, thereby permitting the nucleic acid sequence encoding the siRNA to be passed on to the progeny of the cell when it divides. Promoter sequences in the LTR region have can enhance expression of an inserted coding sequence in a variety of cell types. Some disadvantages of using a retrovirus expression vector are (1) insertional mutagenesis, i.e., the insertion of the nucleic acid sequence encoding the siRNA into an undesirable position in the target cell genome which, for example, leads to unregulated cell growth and (2) the need for target cell proliferation in order for the nucleic acid sequence encoding the siRNA carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

In one embodiment of the present invention, one will desire to generate siRNA in a brain cell or brain tissue. A suitable vector for this application is an FIV vector or an AAV vector. For example, one may use AAV5. Also, one may apply poliovirus or HSV vectors.

Application of siRNA is generally accomplished by transfection of synthetic siRNAs, in vitro synthesized RNAs, or plasmids expressing shRNAs or miRNAs. More recently, viruses have been employed for in vitro studies and to generate transgenic mouse knock-downs of targeted genes. Recombinant adenovirus, adeno-associated virus (AAV) and feline immunodeficiency virus (FIV) can be used to deliver genes in vitro and in vivo. Each has its own advantages and disadvantages. Adenoviruses are double stranded DNA viruses with large genomes (36 kb) and have been engineered by my laboratory and others to accommodate expression cassettes in distinct regions.

Adeno-associated viruses have encapsidated genomes, similar to Ad, but are smaller in size and packaging capacity (~30 nm vs. ~100 nm; packaging limit of 4.5 kb). AAV contain single stranded DNA genomes of the + or the – strand. Eight serotypes of AAV (1-8) have been studied extensively, three of which have been evaluated in the brain. An important consideration for the present application is that AAV5 transduces striatal and cortical neurons, and is not associated with any known pathologies.

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

Further provided by this invention are chimeric viruses where AAV can be combined with herpes virus, herpes virus amplicons, baculovirus or other viruses to achieve a desired tropism associated with another virus. For example, the AAV4 ITRs could be inserted in the herpes virus and cells could be infected. Post-infection, the ITRs of AAV4 could be acted on by AAV4 rep provided in the system or in a separate vehicle to rescue AAV4 from the genome. Therefore, the cellular tropism of the herpes simplex virus can be combined with AAV4 rep mediated targeted integration. Other viruses that could be utilized to construct chimeric viruses include lentivirus, retrovirus, pseudotyped retroviral vectors, and adenoviral vectors.

Also provided by this invention are variant AAV vectors. For example, the sequence of a native AAV, such as AAV5, can be modified at individual nucleotides. The present invention includes native and mutant AAV vectors. The present invention further includes all AAV serotypes.

FIV is an enveloped virus with a strong safety profile in humans; individuals bitten or scratched by FIV-infected cats do not seroconvert and have not been reported to show any signs of disease. Like AAV, FIV provides lasting transgene expression in mouse and nonhuman primate neurons, and transduction can be directed to different cell types by pseudotyping, the process of exchanging the virus's native envelope for an envelope from another virus.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (Promega®, Madison, Wis.). However, the efficiency of transfection by these methods is highly dependent on the nature of the target cell and accordingly, the conditions for optimal transfection of nucleic acids into cells using the herein-mentioned procedures must be optimized. Such optimization is within the scope of one of ordinary skill in the art without the need for undue experimentation.

VI. Diseases and Conditions Amendable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to siRNA therapy" embraces conditions such as genetic diseases (i.e., a disease condition that is attributable to one or more gene defects), acquired pathologies (i.e., a pathological condition that is not attributable to an inborn defect), cancers, neurodegenerative diseases, e.g., trinucleotide repeat disorders, and prophylactic processes (i.e., prevention of a disease or of an undesired medical condition). A gene "associated with a condition" is a gene that is either the cause, or is part of the cause, of the condition to be treated. Examples of such genes include genes associated with a neurodegenerative disease (e.g., a trinucleotide-repeat disease such as a disease associated with polyglutamine repeats, Huntington's disease, and several spinocerebellar ataxias), and genes encoding ligands for chemokines involved in the migration of a cancer cells, or chemokine receptor. Also siRNA expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

Differences between alleles that are amenable to targeting by siRNA include disease-causing mutations as well as polymorphisms that are not themselves mutations, but may be linked to a mutation or associated with a predisposition to a disease state. An example of a targetable polymorphism that is not itself a mutation is the polymorphism in exon 58 associated with Huntington's disease.

Single nucleotide polymorphisms comprise most of the genetic diversity between humans. The major risk factor for developing Alzheimer's disease is the presence of a particular polymorphism in the apolipoprotein E gene.

Single nucleotide polymorphisms comprise most of the genetic diversity between humans, and that many disease genes, including the HD gene in Huntington's disease, contain numerous single nucleotide or multiple nucleotide polymorphisms that could be separately targeted in one allele vs. the other. The major risk factor for developing Alzheimer's disease is the presence of a particular polymorphism in the apolipoprotein E gene.

A. Gene Defects

A number of diseases caused by gene defects have been identified. For example, this strategy can be applied to a major class of disabling neurological disorders. For example this strategy can be applied to the polyglutamine diseases, as is demonstrated by the reduction of polyglutamine aggregation in cells following application of the strategy. The neurodegenerative disease may be a trinucleotide-repeat disease, such as a disease associated with polyglutamine repeats, including Huntington's disease, and several spinocerebellar ataxias. Additionally, this strategy can be applied to a non-degenerative neurological disorder, such as DYT1 dystonia.

B. Acquired Pathologies

As used herein, "acquired pathology" refers to a disease or syndrome manifested by an abnormal physiological, biochemical, cellular, structural, or molecular biological state. For example, the disease could be a viral disease, such as hepatitis or AIDS.

C. Cancers

The condition amenable to gene silencing therapy alternatively can be a genetic disorder or an acquired pathology that is manifested by abnormal cell proliferation, e.g., cancer. According to this embodiment, the instant invention is useful for silencing a gene involved in neoplastic activity. The present invention can also be used to inhibit overexpression of one or several genes. The present invention can be used to treat neuroblastoma, medulloblastoma, or glioblastoma.

VII. Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of siRNA may be accomplished through the administration of the nucleic acid molecule encoding the siRNA. Pharmaceutical formulations, dosages and routes of administration for nucleic acids are generally known.

The present invention envisions treating a disease, for example, a neurodegenerative disease, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The invention will now be illustrated by the following non-limiting Examples.

EXAMPLE 1

RNAi Silencing

The present inventors modified human mir-30 to contain sequences specific for genes of interest (FIG. 1). Stem base and loop sequences were conserved.

The inventors were able to silence a target gene with miRNA shuttles. The target gene (in this case Ataxin-1, also called SCA1) was cloned and the SCA1 miRNA was also generated, as indicated in FIG. 2. Fluorescence microscopy and western blot analyses was performed and the results indicated dose-dependent silencing of ataxin-1 48 hours after co-transfection of HEK293 cells with RNAi:Target plasmids.

Figure 3:
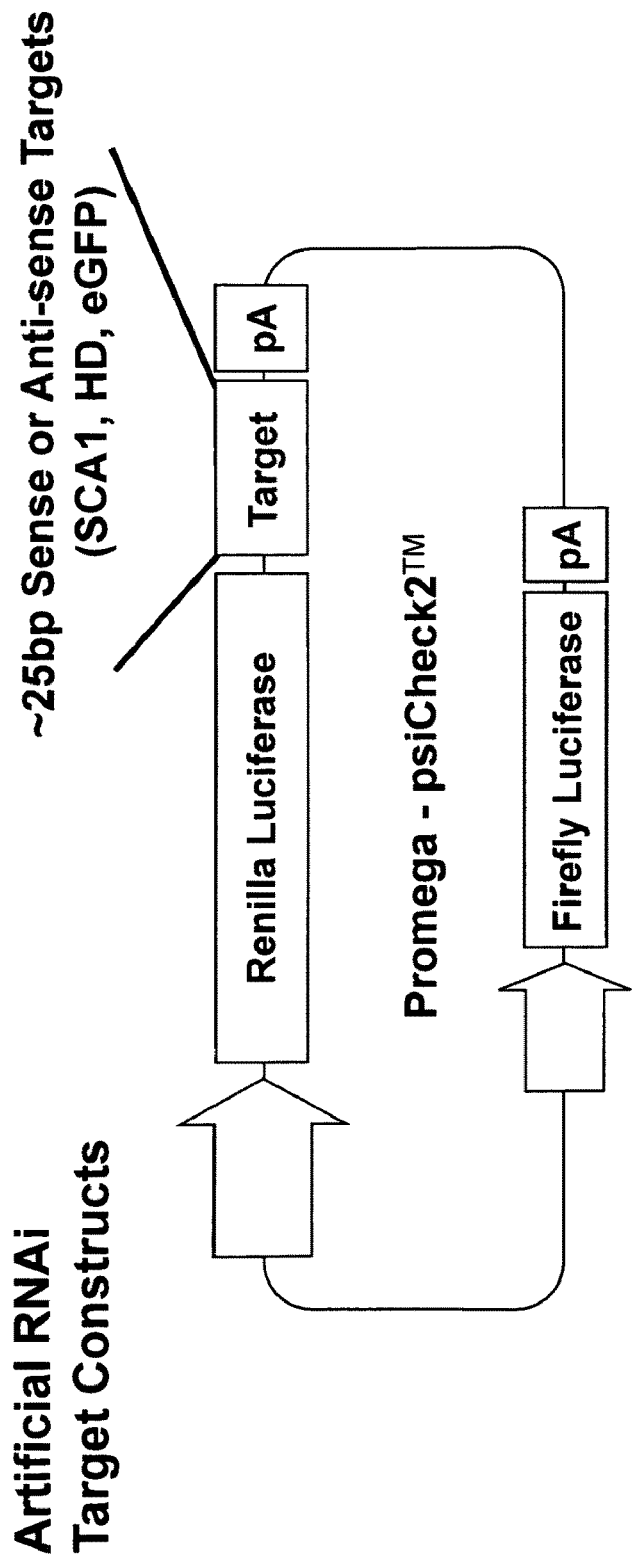
FIG. 3. Artificial RNAi target constructs were generated in both directions.

Next, a comparison study was designed to compare silencing efficiencies of various RNAi vectors and to assess strand incorporation into RISC using a highly sensitive, artificial reporter system. The inventors wanted to learn which vector is most optimal, and if the results would remain consistent independent of target. Since both siRNA strands have the potential to enter the RISC complex, artificial RNAi target constructs were generated in both directions (FIG. 3). Guide antisense-strands target sense targets (e.g., SCA1-Sense), while siRNA sense-strands target anti-sense targets (e.g., SCA1-Antisense).

First, miRNA molecules were compared to "1$^{st}$ generation" shRNA molecules (FIG. 4). 1$^{st}$ generation shRNAs preferentially loaded the unintended strand. Also, these shRNAs lack 2-nt 3' overhangs that are optimal substrates for RNAi pathway machinery.

Figure 5:
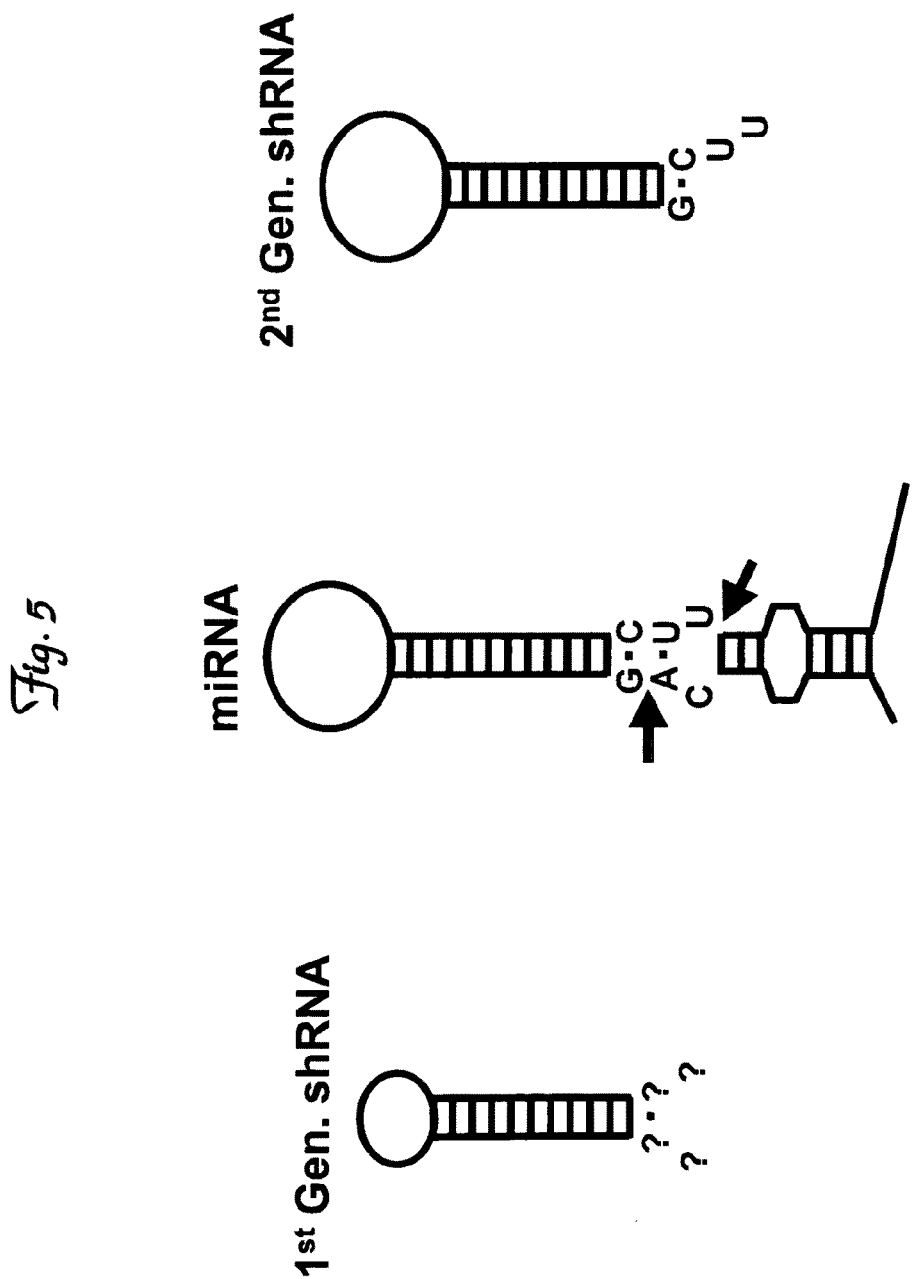
FIG. 5. Design of $2^{nd}$ generation shRNA molecules.
Figure 8:
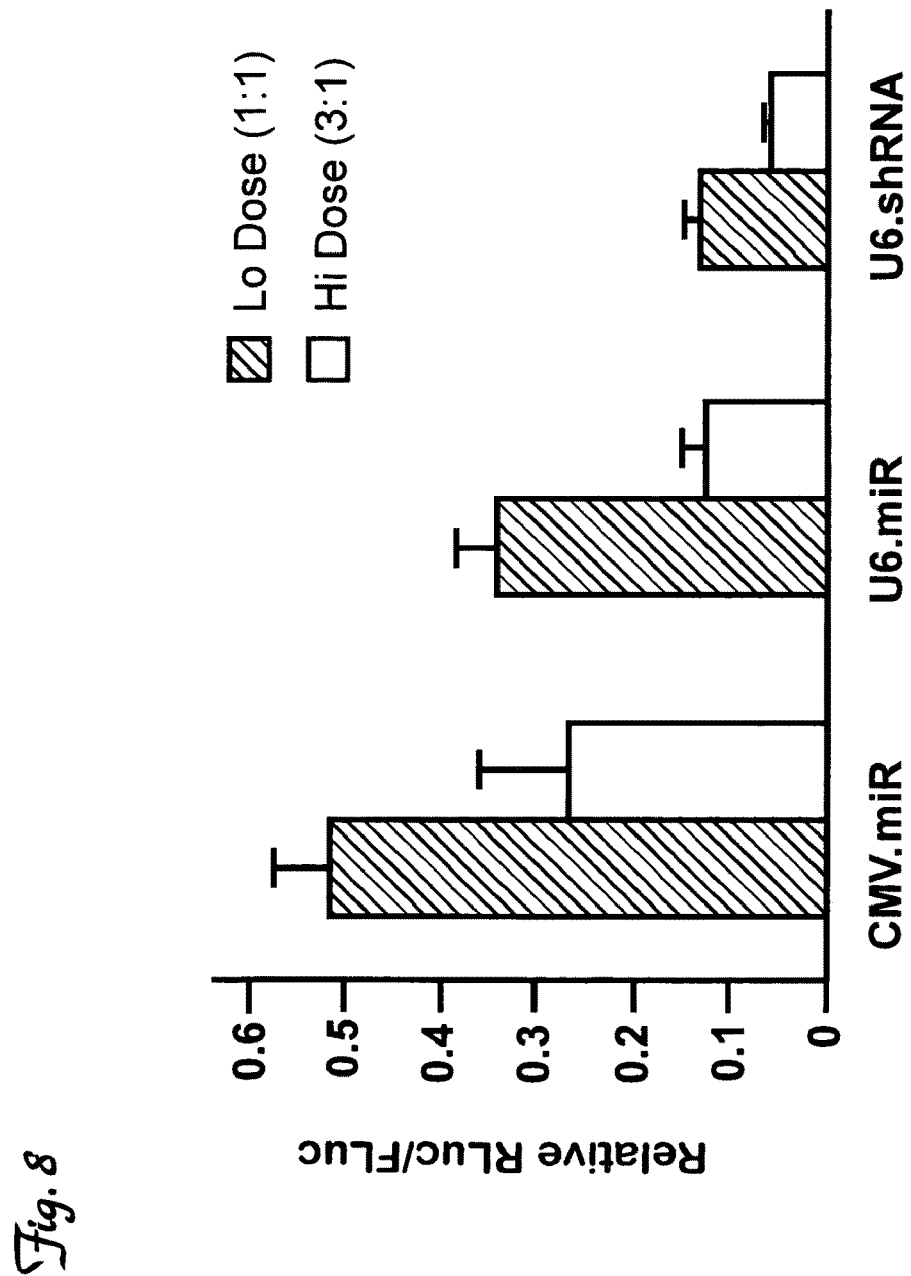
FIG. 8. Comparison of $2^{nd}$ generation shRNA molecules and miRNA molecules.
Figure 10B:
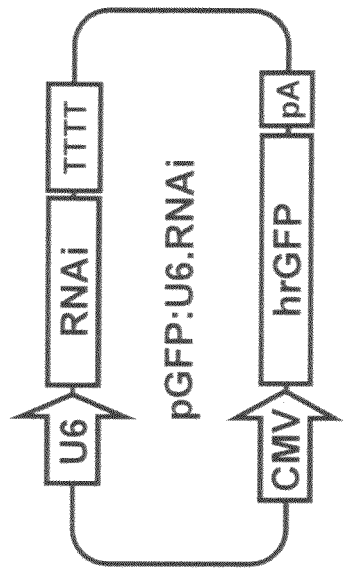
FIGS. 10A-10D. A. Differentiating C2C12 cells induces miR-1 and MHC expression. B. Vector used to compare RNAi strategies. C. RNAi and siCheck2 miR-1 luciferase reporter were co-transfected into C2C12 cells which were then differentiated for 72 hours and dual-luciferase assay was performed. Results are shown relative to siCheck2 alone. D. RNAi plasmids were transfected and cells were differentiated for 72 hours. shRNA-treated cells showed decreased cell viability as observed by fluorescence and quantified by MTS assay.
Figure 10D:
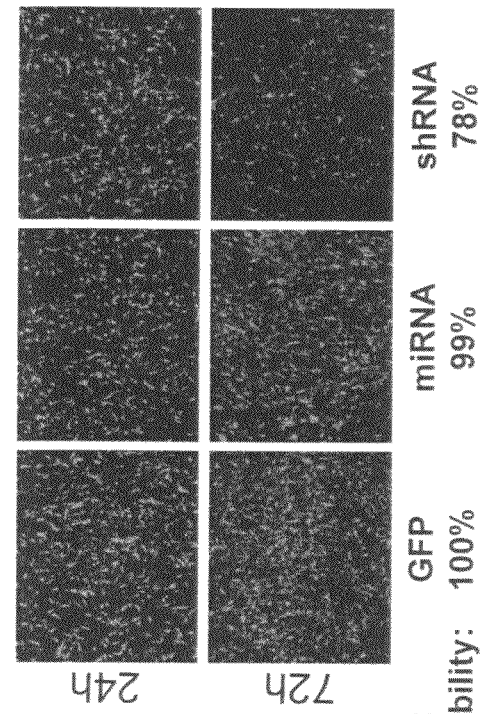
Figure 10A:
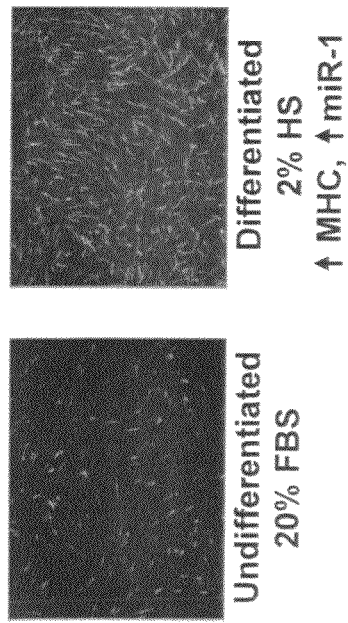
Figure 10C:
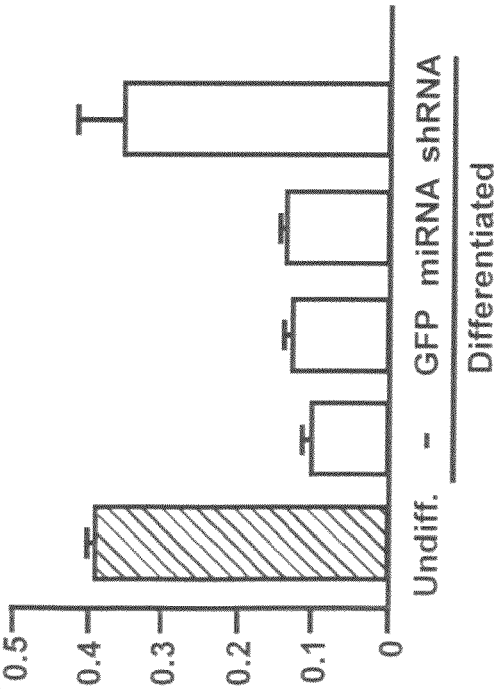

To fairly compare RNAi strategies, optimized shRNAs ("2$^{nd}$ generation" shRNA molecules) were designed to mimic pre-miRNAs (i.e., Drosha-cleaved), which are indicated as arrows in FIG. 5. Corresponding miRNAs were generated to account for the G (U6+1) and UU (polIII terminator) involved in shRNA transcription. Using the 2$^{nd}$ generation shRNA molecules, RNAi against HD and SCA1 showed similar results (northern blot and siChk2 targeting) as the eGFP RNAi constructs (FIGS. 6 and 7). The compilation of Dual-Glo® luciferase assay results from 10 RNAi comparison experiments (4 eGFP, 4 SCA1 and 2 HD) using the artificial siChk2 targets were compared relative to mock RNAi (FIG. 8). This trend in silencing efficacy was also observed when targeting natural eGFP and endogenous SCA1 or HD (data not shown).

Simulated Safety of RNAi Vectors

The inventors also investigated how extensively the RNAi expression approaches disrupt endogenous miRNA processing and function. The inventors designed an in vitro simulated RNAi safety experiment. 293 cells were transfected with U6.miGFP and siChk2-eGFP Target (1:1). Non-specific RNAi "spikes" (U6.shSCA1 or U6.miSCA1) were co-transfected to assess their effect on miGFP-mediated silencing. In this experiment, an increase in light was evidence of toxicity (i.e., RNAi pathway saturation). The results indicated that in safety studies, shRNAs at low doses inhibit the processing of and silencing mediated by artificial miRNAs. The results also indicated that miRNAs at high doses only cause minimal inhibition. It is important to note that the silencing efficacy of shRNA (low dose) and miRNA (high dose) are similar (FIG. 9).

The safety of RNAi in C2C12 cells was also examined (FIG. 10). The shRNA-treated cells showed decreased cell viability as compared to the miRNA-treated cells.

In Vivo Safety of RNAi Vectors in Muscle

The inventors co-electroporated miReporter and GFP: U6.RNAi plasmids into the tibialis anterior (shRNA:Left or miRNA:Right) (FIG. 11). IVIS imaging was used for Firefly or *Renilla* Luciferase and GFP. The inventors wanted to learn if there was disruption of endogenous miRNA function (i.e., more light) between the different vectors. The results show that miRNA vectors were safe in vivo (FIG. 12).

In conclusion, the inventors found that the miRNA approach is more effective than 1$^{st}$ generation shRNA; that Optimized 2$^{nd}$ generation shRNAs silence more effectively than miRNAs; that shRNAs inhibit miRNA-mediated silencing substantially more than the corresponding miRNA-shuttle vectors; and that miRNA-based strategies provide safer therapeutics.

EXAMPLE 2

Silencing of HD in Mouse Striatum

Figure 13B:
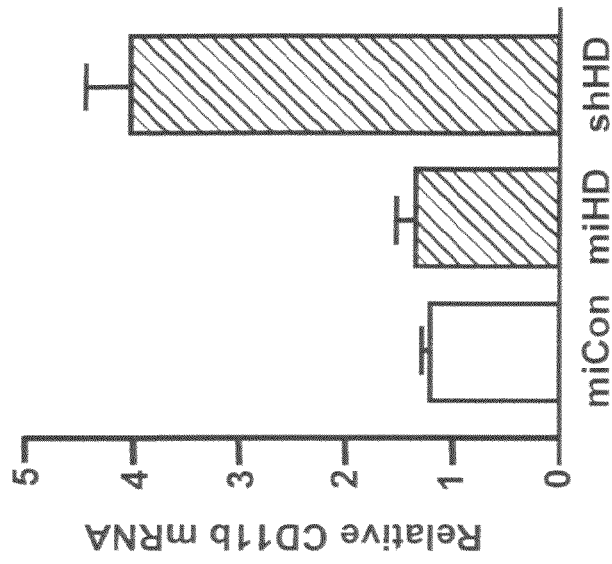
FIGS. 13A-13B. Q-PCR was performed for mouse HD (FIG. 13A) and CD11b (FIG. 13B). Northern blots were also prepared for RNAi. The Q-PCR results were normalized to GAPDH mRNA levels and are shown relative to uninjected striatum. High-level expression from shRNA likely explains the observed toxicity.
Figure 13A:
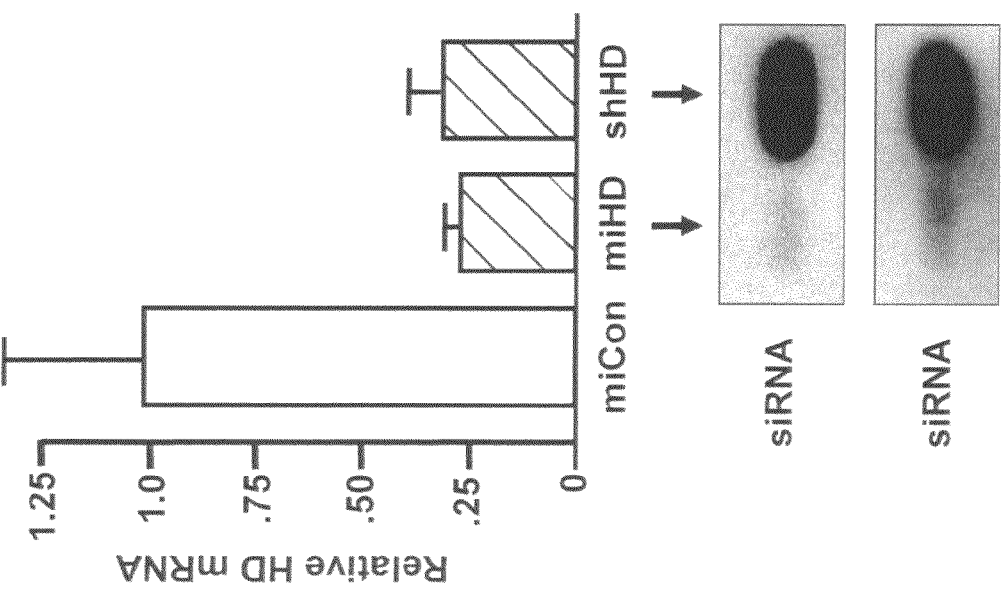
Figure 14:
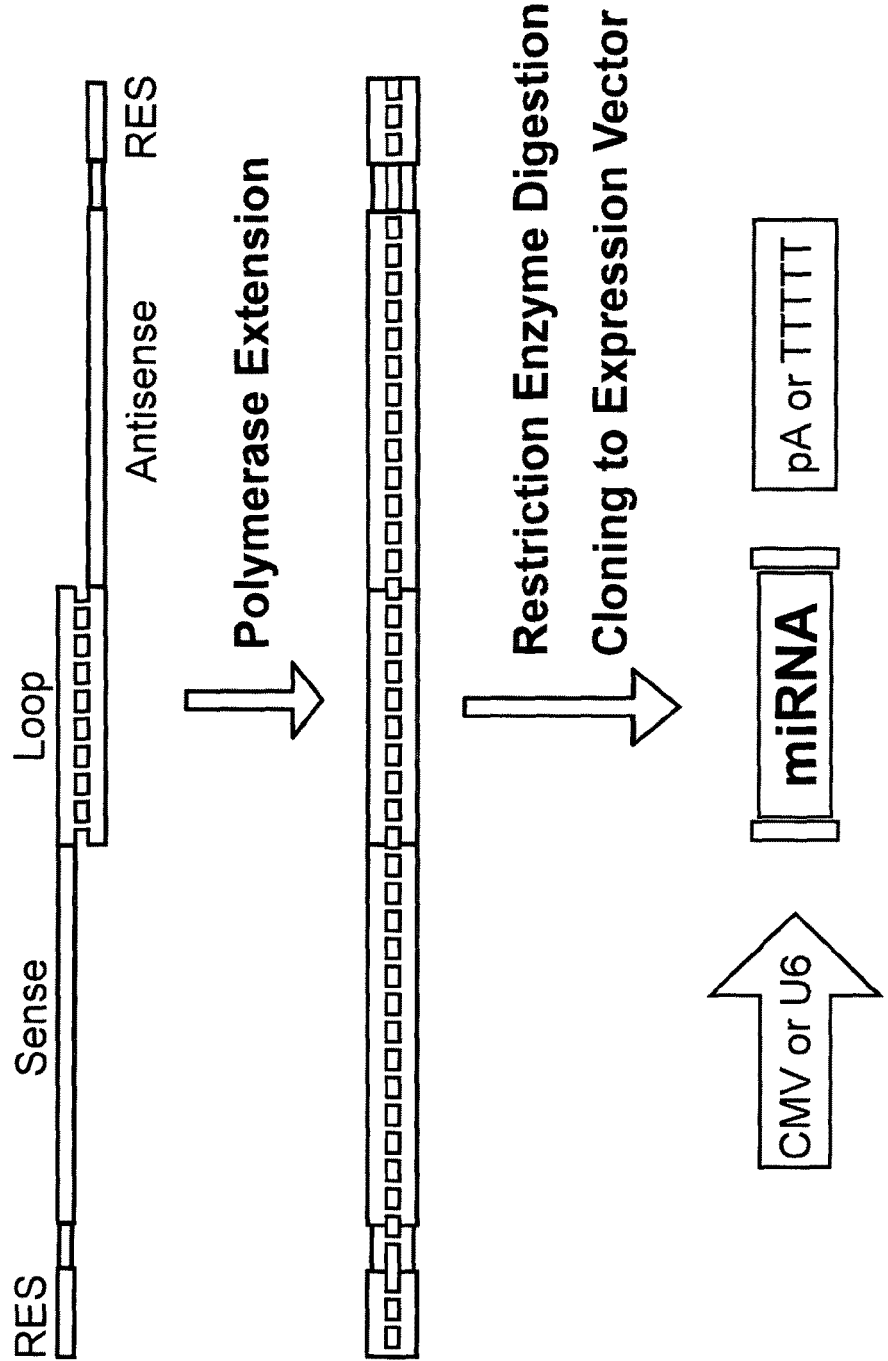
FIG. 14. miRNA shuttle cloning strategy.
Figure 15:
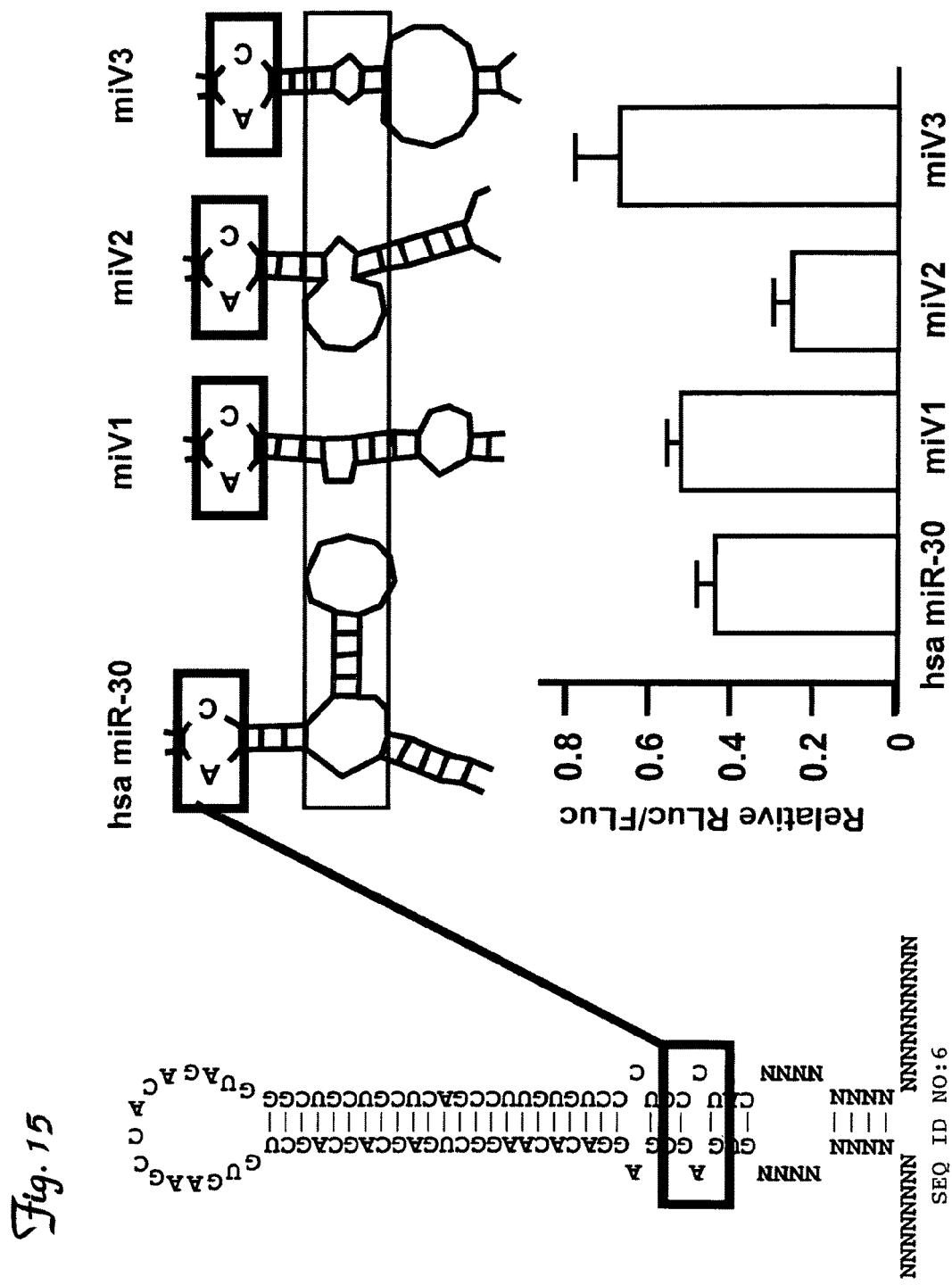
FIG. 15. Generation of miRNA molecules (exemplary miRNA at the left of the figure is SEQ ID NO:6).

AAV vectors for RNAi molecules specific for a target were injected into mouse striatum. Four months later, GFP-positive striata was harvested, and RNA was isolated. Q-PCR was performed for mouse HD and CD11b, as well as Northern blots (FIG. 13). High-level expression from shRNA likely explains the observed toxicity.

miRNA molecules were generated following the strategy set forth in FIGS. 14 and 15.

EXAMPLE 3

An expression cassette (5'NheI-3'BglII) containing the CMV promoter, multiple cloning site (MCS) and SV40 polyadenylation signal was cloned into TOPObluntI (XbaI-BamHI, Invitrogen™) in reverse orientation. A polIII expression cassette containing mouse U6 promoter, MCS and PolIII-terminator (6T's) was cloned into TOPObluntII with the same strategy. miRNA shuttles were generated by polymerase extension of overlapping DNA oligonucleotides (IDT). Polymerase-extended products were digested with XhoI-SpeI and cloned in the MCS of the expression vectors XhoI-SpeI (miV1) or XhoI-XbaI (miV2). shHD2.1 production has been previously described. Other shRNAs were cloned using a tailed-PCT strategy. PCR products containing U2-shRNA-6T's were TOPO cloned into the bluntII vector and positive clones were considered to be in reverse orientation to maintain consistency with the other expression vectors.

RNAi luciferase reporter vectors were constructed using psiCheck2 (Promega®). Tailed-PR was used to amplify a 3' fragment of *Renilla* luciferase containing a single, perfect complementary RNAi Target site (~25 bp: 21 bp target+2 nt 5' and 3') downstream of the stop codon. This PCR product was digested with AatII-XhoI and cloned into the same sites within psiCheck2. The vector sequences are shown in FIG.

16. FIG. 19 shows additional miRNA sequences that were used to target either HD or SCA1. These are the predicted RNA stem loop structures that contain the active RNAi sequences. The active antisense strand of the embedded siRNA sequence is underlined.

Figure 17:
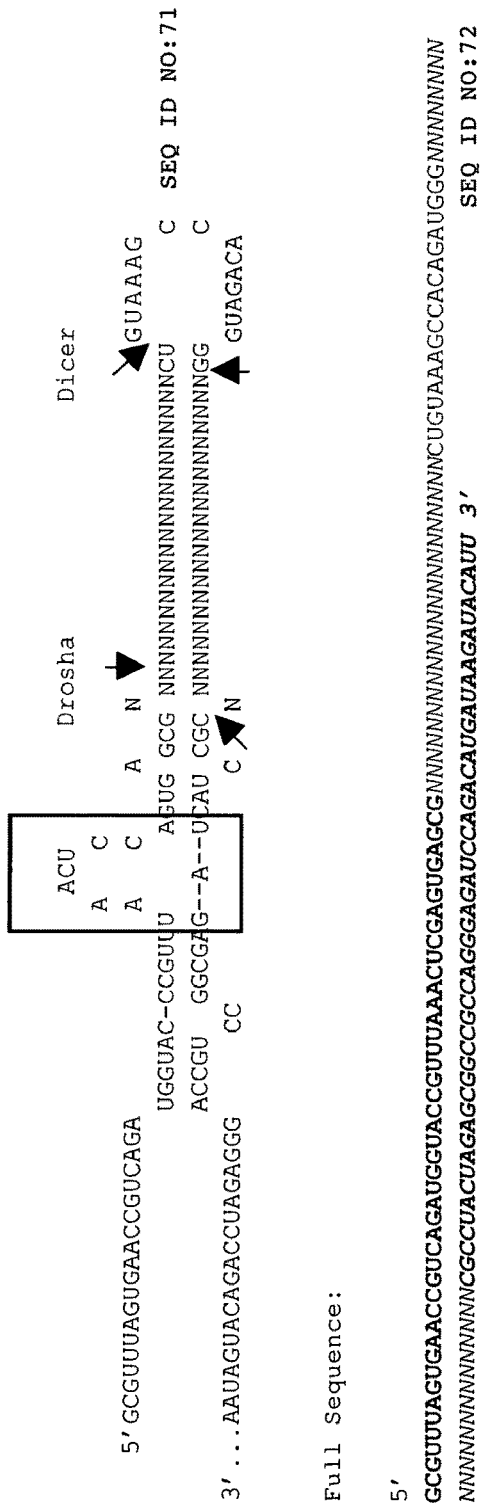
FIG. 17. Basic miRNA Structure of mi-Variant 2. 5' flanking sequence (bold text), siRNA sequence (italics), Loop (normal text), and 3' flanking sequence (bold italics).

FIG. 17 shows the basic miRNA structure of Variant 2. Variant 1 and Variant 3 form unique structures which direct less efficient Drosha processing than Variant 2. It was unexpected that Variant 2 would be much more efficient than Variants 1 and 3, based on the design algorithm.

Variants 1 and 3 may provide alternatives to further de-dose RNAi strategies. If one desired a high degree of knock-down, then one would use Variant 2. If, however, a lesser degree of knock-down was desired, one would use Variant 1 or 3. The boxed region shown in FIG. 17 indicates a region that affects silencing efficiency, presumably by influencing Drosha cleavage efficiency or accuracy. The region is located in the stem-base 10-12 base pairs away from the Drosha cleavage sites. Silencing efficiency was improved when this region was made unstable (i.e., no base pairing or bulged loop). Silencing efficiency is reduced when this region is made more stable (i.e., base pairing, no or small loop). Variants 1 and 3 contain more stable conformations and, hence, are less efficient than Variant 2.

To improve the RNAi strategy, the inventors investigated the use of artificial miRNAs as siRNA shuttles. The inventors modified the human miR-30 primary transcript by replacing the mature miR-30 region (~20-bp duplex which is excised via sequential Drosha and Dicer processing) with desired siRNA sequences (FIG. 18A). The structure of miR-30 has been well-characterized, and the major Drosha and Dicer cleavage sites have been experimentally validated. The inventors generated artificial miRNAs containing the structural elements within the stem-base required for effective Drosha processing but otherwise devoid of natural miR-30 flanking sequences. With this strategy, the flanking sequences (~35-nt upstream and ~40-nt downstream) arise from the vector sequence within the multiple cloning site (MCS). Although the minimal sequence elements necessary for miR-30 processing are known, the effects of flanking sequences, and consequently the transcript structure within the nearby stem-loop base, on processing efficiency has not been evaluated. To test this, the inventors generated miR-30 shuttle variants predicted to form unique RNA structures proximal to the base of an identical miRNA stem-loop (FIGS. 18A,B). Luciferase reporters containing a siRNA target site (~25-bp) within the 3'UTR, herein referred to as RNAi luciferase reporters (FIG. 18C), were developed to assess silencing efficiencies in co-transfection studies. The variant flanking sequences influenced silencing efficacy relative to the same miRNA stem-loop flanked by natural human miR-30 sequences (FIG. 18D). Notably, one miRNA variant (miV2) yielded 20% more gene knockdown than the natural miR-30 structure (P<0.01). This improved silencing was likely the result of improved processing, as miV2 generated the most antisense RNA as determined by small transcript northern blot. Interestingly, miV2 exhibits a region of single-stranded nature (FIG. 18B, shaded region) that may promote binding of the Drosha-DGCR8 complex, as supported by models for pri-miRNA processing.

EXAMPLE 4

Minimizing Variables Among Hairpin-Based RNAi Vectors Reveals the Potency of shRNAs RNA interference (RNAi) is an evolutionarily conserved cellular process regulating gene expression and participating in innate defense against transposable elements and viral invasion. RNAi mediates sequence-specific gene silencing by double-stranded RNAs (dsRNAs) which may be processed by Dicer into functional small RNAs [small interfering RNAs (siRNAs) and microRNAs (miRNAs) among others]. Small RNAs associated with the RNA-induced silencing complex (RISC) or RISC-like complexes mediate post-transcriptional gene silencing by targeting transcripts for degradation or translational repression. Also, small RNAs in RISC-like complexes may direct heterochromatin formation to mediate transcriptional gene silencing.

RNAi has been utilized as a tool to query gene function and is being developed as a modality for disease therapy. Exogenous RNAi has been expressed in cultured cells and organisms as short-hairpin RNAs (shRNAs) or artificial miRNAs (FIG. 18A). The basic transcriptional unit of a shRNA is sense and antisense sequences connected by a loop of unpaired nucleotides. shRNAs are exported from the nucleus by Exportin-5, and once in the cytoplasm, are processed by Dicer to generate functional siRNAs. miRNA stem-loops are typically expressed as part of larger primary transcripts (pri-miRNAs). The Drosha-DGCR8 complex excises the stem-loops generating intermediates known as pre-miRNAs, which are subsequently exported to the cytoplasm and diced into functional small RNAs.

Previous studies from several laboratories, including that of the inventors, demonstrate the utility and efficacy of shRNAs in vitro and in vivo. However, the use of artificial miRNAs (pri-miRNA scaffolds shuttling siRNA sequences) as RNAi vectors has become an attractive alternative. Artificial miRNAs more naturally resemble endogenous RNAi substrates and are more amenable to Pol-II transcription (allowing tissue-specific expression of RNAi) and polycistronic strategies (allowing delivery of multiple siRNA sequences). A persistent question in the field, however, is which RNAi expression system is most optimal for achieving gene silencing in particular applications.

Optimization of RNAi strategies remains important due to the potential side-effects caused by exogenously delivered RNAi. RNAi vectors may compete for endogenous RNAi machinery, stimulate cellular responses to dsRNA, or silence unintended target mRNAs due to partial complementarity. These side effects can produce severe cellular toxicity and even result in organismal death. Improved RNAi-based gene silencing strategies may allow delivery of lower doses, thus reducing the likelihood of RNAi-related side-effects.

To date, shRNA- and artificial miRNA-based strategies have been compared with conflicting results. In certain comparisons, the shRNAs tested had sub-optimal 5' overhangs due to variable arrangements of transcription start and stop sequences, some caused inadvertently by the use of restriction enzyme sites during vector production. This raises concerns since recent reports have demonstrated that 2-nt 3' overhangs, often observed in natural pre-miRNAs, are optimal substrates for Exportin-5 and Dicer. Furthermore, none of the prior hairpin-based comparisons assessed the equivalency of strand-biasing. Strand-biasing refers to which strand of the siRNA duplex enters the RISC and mediates gene silencing. In general, the strand with the weakest base-pairing near the 5' end will be incorporated into the RISC. Hence, shRNA and artificial miRNA comparisons may be confounded if the vectors, following processing, release siRNAs which exhibit differential strand-biasing (i.e., one loading the intended antisense strand and the other loading the unintended sense strand). Indeed, a single base-pair shift during RNAi substrate processing may alter which strand of the resulting siRNA preferentially enters the RISC, thus highlighting the importance of evaluating strand-biasing in RNAi vector comparison studies.

The present inventors have demonstrated how early-generation shRNAs with poor strand-biasing confound the comparison of hairpin-based RNAi approaches. Minimizing the variables for comparison reveals that, for three independent target sequences and in different settings (in vitro and in vivo), shRNAs are more potent than artificial miRNAs.

Results

Development of an Improved miR-30-Based siRNA Shuttle

The inventors have previously demonstrated the therapeutic efficacy of shRNAs in mouse models of neurodegenerative diseases [Spinocerebellar Ataxia Type I (SCA1) and Huntington's disease (HD)] (Xia et al., Nat Med, 10(8), 816-820 (2004); Harper et al., 2005, PNAS, 102: 5820-5825). To improve the RNAi strategy, the inventors investigated the use of artificial miRNAs as siRNA shuttles. The inventors modified the human miR-30 primary transcript by replacing the mature miR-30 region (~20-bp duplex which is excised via sequential Drosha and Dicer processing) with desired siRNA sequences (FIG. 18A). The structure of miR-30 has been well-characterized, and the major Drosha and Dicer cleavage sites have been experimentally validated. The inventors generated artificial miRNAs containing the structural elements within the stem-base required for effective Drosha processing but otherwise devoid of natural miR-30 flanking sequences. With this strategy, the flanking sequences (~35-nt upstream and ~40-nt downstream) arise from the vector sequence within the multiple cloning site (MCS). Although the minimal sequence elements necessary for miR-30 processing are known, the effects of flanking sequences, and consequently the transcript structure within the nearby stem-loop base, on processing efficiency has not been evaluated. To test this, the inventors generated miR-30 shuttle variants predicted to form unique RNA structures proximal to the base of an identical miRNA stem-loop (FIGS. 18A,B). Luciferase reporters containing a siRNA target site (~25-bp) within the 3'UTR, herein referred to as RNAi luciferase reporters (FIG. 18C), were developed to assess silencing efficiencies in co-transfection studies. The variant flanking sequences influenced silencing efficacy relative to the same miRNA stem-loop flanked by natural human miR-30 sequences (FIG. 18D). Notably, one miRNA variant (miV2) yielded 20% more gene knockdown than the natural miR-30 structure (P<0.01). This improved silencing was likely the result of improved processing, as miV2 generated the most antisense RNA as determined by small transcript northern blot (FIG. 18E). Interestingly, miV2 exhibits a region of single-stranded nature (FIG. 18B, shaded region) that may promote binding of the Drosha-DGCR8 complex, as supported by models for pri-miRNA processing.

Strand-Biasing Confounds Hairpin-Based Comparisons

Figure 26A:
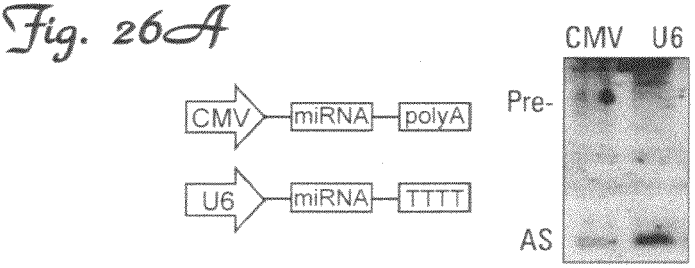
FIGS. 26A-26B.
Figure 26B:
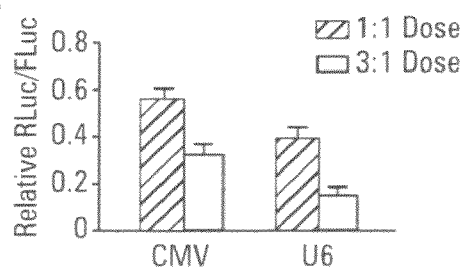

The inventors next developed miR-30 shuttles (miV1 and miV2) containing siRNA sequences based on HD2.1 [targets the transcript of the human Huntington's disease (HD) gene] to compare to the short-hairpin shHD2.1 (a shRNA previously tested in therapeutic efficacy studies in a mouse model for HD (Harper et al., 2005, PNAS, USA 102: 5820-5825)). The processing of CMV-driven miHD2.1 variants and U6-driven shHD2.1 was assessed by small transcript northern blot analysis (FIG. 4A). The miRNA-based shuttles yielded more antisense RNA than the shRNA vector which generated an abundance of unprocessed precursor stem-loop RNAs. Also, miV2 generated more antisense RNA than miV1 as previously observed in FIG. 18E. Importantly, the improvement of the artificial miRNAs over the shRNA was not the result of promoter discrepancies since the U6-miRNA vectors were even more potent than the CMV-miRNA vectors (FIG. 26; P<0.01).

The silencing efficiencies of CMV-miHD2.1(V2) and U6-shHD2.1 against endogenous HD transcripts were assessed by Q-PCR following transfection of RNAi expression vectors into human-derived HEK293 cells. Consistent with our northern blot results, miHD2.1 demonstrated approximately 50% improved silencing of endogenous HD mRNA relative to shHD2.1 (FIG. 4B; P<0.05). These findings support prior data showing that miRNA-based strategies are more potent than first-generation shRNAs. However, because recent work has shown that strand-biasing affects siRNA-mediated gene silencing, the inventors tested whether shHD2.1 and miHD2.1 (both U6-driven) preferentially load the intended antisense strand or unintended sense strand. The inventors designed RNAi luciferase reporters containing either sense or antisense target sites to evaluate the silencing activity of each strand. Co-transfection studies revealed that shHD2.1 preferentially silenced the unintended target, while miHD2.1 favored silencing of the intended strand (FIG. 4C). These data are important as they demonstrate that disparate strand-biasing can confound comparisons of shRNA- and miRNA-based approaches.

shRNA Expression and Potency is Overhang-Dependent

Figures 21A, 21B, 21C, 21D:
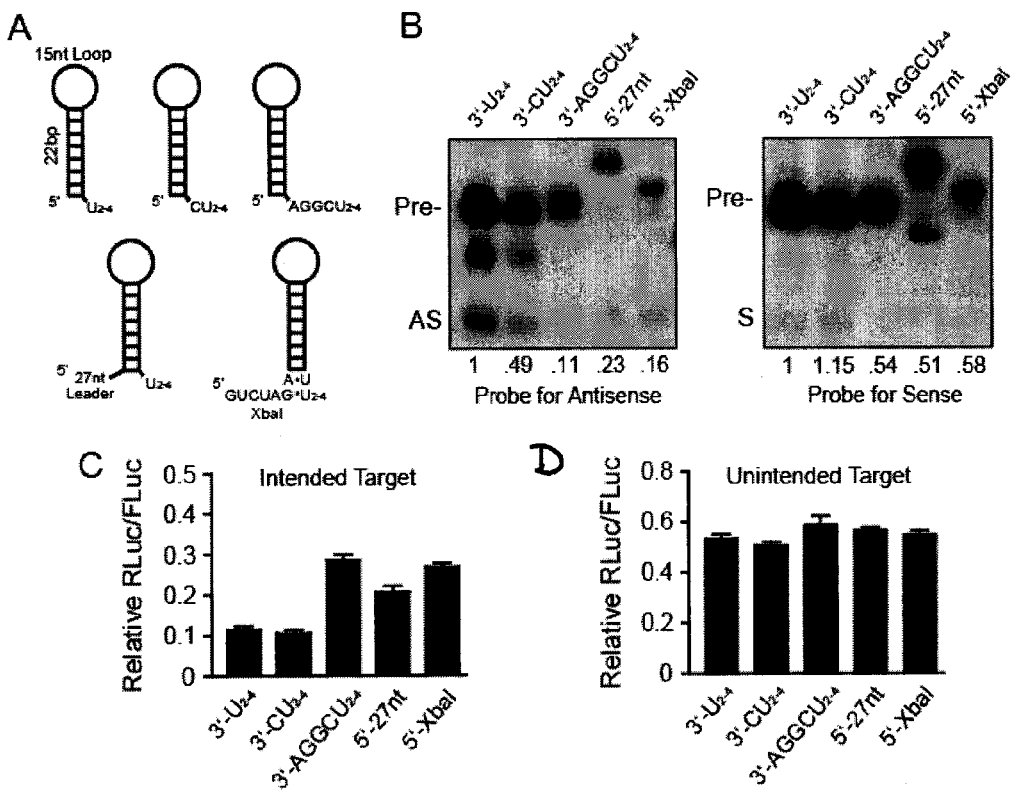
FIGS. 21A-21D. shRNA processing and silencing efficiency is overhang-dependent.

To more fairly compare shRNA- and miRNA-based silencing strategies, the inventors designed shRNAs using the predicted structure of Drosha-cleaved miR-30 stem-loops as a design guide. These shRNAs were designed to have minimized 3' overhangs (2-4 Us resulting from Pol-III termination) to resemble the 2-nt 3' overhangs which result from Drosha cleavage. Overhangs of this length provide optimal substrates for Exportin-5 and Dicer. In addition, target sequences were selected to account for the +1-G nucleotide of the mouse U6 promoter and to contain AU-rich 3' ends, both of which promote loading of the antisense strand. While designing shRNAs in this manner is becoming common practice, the initial shRNA-miRNA comparison studies tested shRNAs with sub-optimal overhangs. Hence, the inventors revisited testing the effects of shRNA overhangs (5' and 3') on processing and silencing efficiency. The inventors developed a series of vectors expressing a common shRNA but with altered overhang lengths, in certain cases, resembling those (i.e., 5' variants) found in previous shRNA and artificial miRNA comparison studies (FIG. 21A). Northern blot and densitometry analyses showed that shRNAs with the minimal $3'$-$U_{2-4}$ overhangs yield 3- and 4-fold more pre-shRNA (unprocessed) and antisense RNA (processed), respectively, than shRNAs with 5'-overhangs (FIG. 21B). Unexpectedly, shRNA expression levels appear to decrease with lengthening 5' or 3' overhangs. The inventors presume that sub-optimal overhangs lower shRNA transcript stability, considering that all variants were expressed by the same mouse U6 promoter and only differ by up to 27-nt in length.

In gene silencing studies targeting a co-transfected RNAi luciferase reporter, the inventors found that shRNAs with minimal overhangs ($3'$-$U_{2-4}$ or $3'$-$CU_{2-4}$) overhangs were most effective (P<0.001), while efficiency is compromised upon increasing 5' or 3' overhangs (FIG. 21C). Northern blot analyses and gene silencing studies targeting sense or antisense RNAi luciferase reporters demonstrated that each shRNA variant favored loading of the intended antisense strand (FIGS. 21B,C). While shRNAs with longer overhangs demonstrate slightly reduced intended:unintended silencing ratios, their decreased silencing efficiencies likely result from reduced transcript stability and processing as supported by our northern blot data.

Figures 22A, 22B:
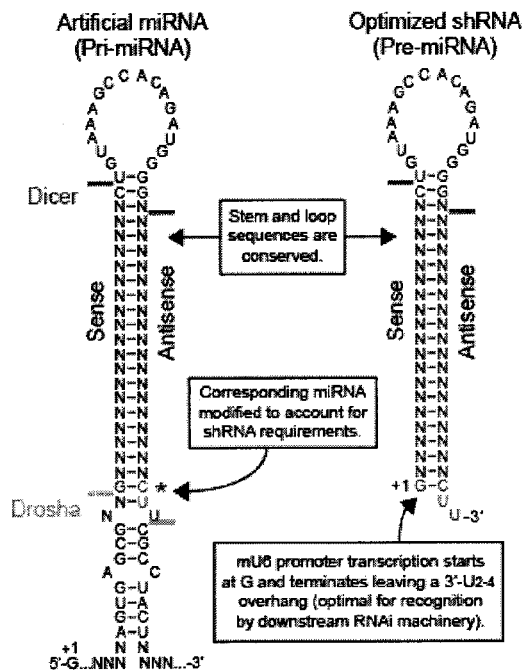
FIGS. 22A-22B. Design of comparable shRNA and artificial miRNA hairpins. Diagram depicting the design of hairpins for a fair comparison scheme. Relevant cleavage sites mapped by 3'-RACE are shown (FIG. 27). Vectors were designed to contain siRNAs targeting SCA1, GFP or HD transcripts (Ns). The stem and loop sequences are conserved. The "*" in FIG. 22A indicates that the corresponding miRNA was modified to account for shRNA requirements. The mU6 promoter transcription starts at G (indicated by an arrow in FIG. 22B) and terminates leaving a 3'-$U_{2-4}$ overhang (FIG. 22B shows 3'-$U_2$), which is optimal for recognition by downstream RNAi machinery. The Dicer cut sites are indicated with darker bars near the loop regions, and the Drosha cut site is indicated by lighter bars in FIG. 22A.

Minimizing the Variables Between Artificial miRNA and shRNA Vectors for Comparison Next, the inventors sought to compare the improved artificial miRNAs (FIG. 18, miV2) and shRNAs (FIG. 22A, 3'U$_{2-4}$) for processing and silencing efficiency. To test for consistency of results independent of target and sequence, the inventors designed shRNA- and miRNA-based vectors targeting SCA1, HD, and GFP mRNAs—the former two providing constructs to further test in therapeutic development. Importantly, and unique from other shRNA and miRNA comparisons (Boden et al., 2004, Nucleic Acids Res 32: 1154-1158; Silva et al., 2005, Nat Genet. 37: 1281-1288; Li et al., 2007, RNA 13: 1765-1774), the inventors' artificial miRNAs were adjusted to account for nucleotide restrictions associated with Pol-III transcription of shRNAs (FIGS. 22A,B). Hence, following Drosha-cleavage, the pre-miRNAs would be comparable to the shRNAs and subsequent processing of each stem-loop by Dicer would yield similar siRNA species. This is an important consideration since a single base-pair shift may alter the strand-biasing or potency of the resulting siRNA.

To evaluate the processing of the current vectors, the inventors performed 3'-RACE to identify the 3' ends of the sense and antisense strands of siRNAs generated by corresponding artificial miRNA and shRNA expression vectors (FIG. 27). To date, none of the RNAi vector comparison studies have performed this important analysis to test the equivalency of processing between the compared vectors. The inventors' 3'-RACE analyses revealed that both RNAi vectors generate at least four siRNA species which were common between the vectors. These findings are consistent with a previous report which demonstrated flexibility (i.e. base-pair shifting) in dsRNA cleavage by Dicer (Vermeulen et al., 2005, RNA 11: 674-682). Notably, the most prevalent species generated by the RNAi vectors was shared, representing approximately 50% of the 3'-RACE sequences analyzed (n=10-12 per vector per strand). These results support the integrity of comparing artificial miRNAs and shRNAs designed with the present strategy.

Next, the inventors assessed the strand-biasing of these RNAi vectors by targeting sense or antisense RNAi luciferase reporters, since inconsistent strand-biasing confounded our original comparison (FIG. 4). In all three RNAi vector-pairs (SCA1, HD, and GFP), a strong preference for silencing the intended strand was observed for both artificial miRNAs and shRNAs (FIG. 23). For the SCA1 and GFP vectors, neither of the RNAi expression strategies silenced the unintended targets, and only minimal activity of the unintended strand was observed with the HD RNAi vectors. These results demonstrate that the desired strand-biasing is consistent for each RNAi vector-pair, thus maintaining their suitability for further comparison studies.

shRNAs Show Improved Potency Relative to Artificial miRNAs

As an initial comparison of gene silencing efficacy, the RNAi vectors and their respective RNAi luciferase reporters were co-transfected into HEK293 cells. Luciferase assay data from several experiments (n=4 SCA1, n=2 HD and n=4 GFP) were compiled, revealing that optimized shRNAs are more potent than artificial miRNAs independent of the RNAi doses tested and target sequence [FIG. 24A; $P<0.001$ and $P<0.05$ for 1:1 and 3:1 (RNAi:Target) doses respectively]. Notably, this improved efficacy of the shRNAs was also observed per vector-pair in our previous strand-biasing studies (FIG. 23).

Though targeting RNAi luciferase reporters provides a quantitative and facile means for assessing gene silencing, the inventors also wanted to evaluate the capacities for these RNAi vectors to silence their natural targets. In HEK293 cells transfected with RNAi expression plasmids, silencing trends of shRNA>miRNA were also observed when targeting endogenous SCA1 or HD transcripts (FIGS. 24B,C; $P<0.05$ and $P<0.001$ respectively). Furthermore, the shRNA targeting GFP demonstrated improved potency over the corresponding artificial miRNA following co-transfection of RNAi and GFP expression plasmids into HEK293 cells (FIG. 24D; $P<0.01$).

Next, the inventors compared the processing efficiencies of our artificial miRNA and shRNA vector-pairs in vitro following transfection of RNAi expression plasmids. Small transcript northern blots demonstrate that, unlike the first-generation shRNAs (FIG. 4A), the optimized shRNAs produce at least 4-fold more antisense RNA as compared to artificial miRNAs independent of target (FIG. 24E). This improved yield likely results from higher expression levels since optimized shRNAs still generate high levels of precursor, whereas artificial miRNAs show minimal build-up of pri- or pre-transcripts.

Figure 25A:
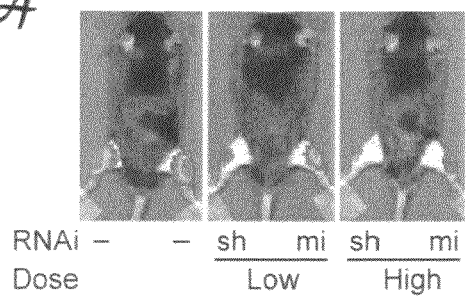
FIGS. 25A-25B. shRNAs are more potent than artificial miRNAs in vivo. Gene silencing efficacy in vivo was compared by co-electroporating SCA1 RNAi and RNAi luciferase reporter plasmids into tibialis anterior muscles of 6-8 week-old mice. Low and high doses are 1:1 and 10:1 (RNAi:Target) ratios respectively. *Renilla* luciferase activity was measured in vivo using bioluminescence imaging after 8 d. Representative "heat-map" images are shown (FIG. 25A) along with quantitative analysis (FIG. 25B) represented as mean±S.E.M (n=4; P<0.05 within each dose). Similar silencing trends were also observed at 4 d post-treatment (data not shown).
Figure 25B:
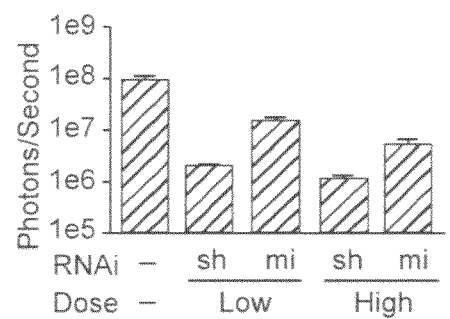

In vivo applications of RNAi are becoming widely used to study gene function or develop therapeutics. As such, the inventors compared one of the present vector-pairs (shSCA1 and miSCA1) for gene silencing in mice. Since these constructs target human SCA1, and not mouse SCA1, the inventors measured in vivo silencing of a co-delivered SCA1 RNAi luciferase reporter. RNAi and RNAi luciferase reporter plasmids were co-electroporated into the tibialis anterior muscles of mice, and bioluminescence imaging was performed to determine in vivo gene silencing at 4 and 8 days post-treatment. At 1:1 and 10:1 (RNAi:Target) ratios, shRNAs show improved potency over artificial miRNAs (FIG. 25). These results, together with the in vitro data, demonstrate that shRNAs can be more potent than miRNAs independent of target and experimental setting (in vitro and in vivo).

Discussion

The inventors have developed a novel miR-30-based siRNA shuttle which shows improved potency over the commonly used miR-30 shuttle which contains natural miR-30 flanking sequences. miRNA-based approaches provide an attractive alternative to classic shRNAs; hence, the inventors compared the efficiencies of these systems in mediating gene silencing.

The inventors present data demonstrating that shRNA and artificial miRNA comparison analyses must be carefully controlled, as differential strand-biasing between the compared vectors may generate misleading results. This possibility, in addition to the use of shRNAs with sub-optimal overhangs, may explain the discrepancies among previously published hairpin-based comparisons studies. The present analyses provide a fair comparison of shRNA- and miRNA-based vectors, taking into consideration the transcribed product, processing sites, and strand-biasing. When variables between the two systems are minimized, shRNAs demonstrate improved silencing efficacy relative to their miRNA-based counterparts. The present experiments are unique in that the inventors carefully controlled vector design (e.g., maintained stem-length and loop structures between compared vectors), assessed the equivalency of siRNAs generated and strand-biasing, and validated the improved potency of shRNAs in vivo. Furthermore, the inventors demonstrate that shRNAs yield abundant levels of precursor and fully processed antisense RNA relative to artificial miRNAs, thus providing mechanistic insight to explain the increased potency.

General users of RNAi must carefully consider the balance of efficacy and toxicity when selecting the most suitable RNAi expression strategy. The improved potency of optimized shRNAs may be offset by toxicity issues; high levels of RNAi substrates (processed and unprocessed) generated from shRNA expression vectors may saturate cellular RNAi machinery, thus interfering with endogenous miRNA biogenesis and function in cell culture and in vivo.

The robust expression of optimized shRNAs may be desirable for certain applications. For example, toxicity is likely minimized in low-copy applications such as the generation of stable cell lines via retroviral vectors, which typically transduce at few to one copy per cell. Hence, shRNAs may be better suited than miRNA-based vectors where low-level expression would preclude sufficient silencing. Alternatively, shRNAs may be advantageous when silencing highly expressed targets which may outcompete low levels of antisense RNA; for example, therapeutic targeting of invasive viruses or cancers, where limiting toxicity may not be the highest priority.

For some applications, high vector doses must be delivered to achieve efficient transduction of a cell population. Hence, shRNA strategies may be undesirable if vector copies per cell cannot be readily limited, as often occurs in vivo, and minimizing toxicity is of high priority. In addition to saturation-based toxicity, high levels of siRNAs may promote silencing of unintended targets via partial complementarity. Hence, utilizing artificial miRNAs, which exhibit lower expression, may provide a unique opportunity to limit RNAi substrate levels when large vector doses must be administered to achieve efficient cell-targeting throughout a given tissue. This concept is particularly relevant to the development of therapeutic RNAi, where transduction efficiency and vector safety are of the utmost importance.

Inevitably, the selection of which hairpin-based RNAi expression system is most suitable for a given application relies on several factors: project goals, delivery options, target expression levels, and desired silencing efficiency. The approach outlined here, where variables of strand-biasing and processing are minimized, can help guide researchers in identifying suitable vectors for their RNAi-based applications.

Material and Methods

Vector Design

An expression cassette (5'NheI-3'BglII) containing the CMV promoter, multiple cloning site (MCS) and SV40 polyadenylation (polyA) signal was cloned into TOPO-BluntII (XbaI-BamHI, Invitrogen™) in reverse orientation. A Pol-III expression cassette containing mouse U6 promoter, MCS and Pol-III-terminator (6T's) was cloned into TOPO-BluntII with the same strategy. Artificial miRNAs were generated by polymerase extension of overlapping DNA oligonucleotides (IDT). Polymerase-extended products were digested with XhoI-SpeI and cloned into the MCS of the expression vectors XhoI-SpeI (miV1) or XhoI-XbaI (miV2). miV3 resulted from an unexplained cloning error. shHD2.1 has been previously described (Harper et al., 2005, *PNAS, USA* 102: 5820-5825). Other shRNAs were cloned using a tailed-PCR strategy. PCR products containing U6-shRNA-6T's were TOPO cloned into the BluntII vector and positive clones were considered to be in reverse orientation to maintain consistency with the other expression vectors.

For in vivo studies, miRNA or shRNA expression cassettes driven by the mouse U6 promoter were cloned in the same orientation upstream of a CMV-hrGFP-SV40polyA expression cassette.

RNAi luciferase reporter vectors were constructed using psiCheck2 (Promega®). Tailed-PCR was used to amplify a 3' fragment of *Renilla* luciferase containing a single, perfect complementary RNAi target site (~25-bp: 21-bp target+2-nt 5' and 3') downstream of the stop codon. This PCR product was digested with AatII-XhoI and cloned into the same sites within psiCheck2.

See FIG. 16 and FIG. 28 for detailed information about vector construction.

3'-RACE Analyses

HEK293 cells grown in 6-well plates were transfected (Lipofectamine™ 2000, Invitrogen™) with RNAi expression plasmids (200 ng or 2 µg for shRNA and artificial miRNA plasmids respectively). Total RNA was isolated at 48 h post-transfection using 1 ml TRIzol® reagent (Invitrogen™). Subsequently, 250 ng of total RNA was treated with A-Plus™ Poly(A) polymerase (Epicentre®), and then subjected to first-strand cDNA synthesis using an anchored oligo-dT primer containing linker sequence (RLM-RACE, Ambion®; TaqMan® reverse transcription reagents, Applied Biosystems). PCR was performed using the following primers: 5'-TTAATACGACTCACTATAGGT-3' (SEQ ID NO: 210) (linker primer), 5'-ACTTCAACGCTGACCT-3' (SEQ ID NO: 211) (SCA1 antisense RACE) and 5'-CCAGGTCAGCGTTGA-3' (SEQ ID NO: 212) (SCA1 sense RACE). Products were TOPO cloned into the pCR2.1 vector (Invitrogen™) and sequenced.

Northern Blot Analyses

HEK293 cells grown in 6-well plates were transfected with 1.5 µg of RNAi expression plasmid. Total RNA was isolated at 48 h post-transfection using 1 ml TRIzol® reagent (Invitrogen™); alternatively, the small RNA fraction was harvested using mirVana Isolation Kit (Ambion®). 15-20 µg total RNA or 1-2 µg small RNA fraction was resolved on a 15% acrylamide gel. Small transcript sizes were determined with the Decade Ladder (Ambion®). Consistent loading and RNA integrity was assessed by ethidium bromide stain. RNA was transferred to Hybond™-XL membrane (Amersham Pharmacia) at 200-400 mA for 1-2 h and UV-crosslinked with the auto-crosslink function on a Stratalinker® 1800 (Stratagene®). Blots were pre-hybridized using UltraHyb-Oligo (Ambion®) at 35° C., probed with $^{32}$P-labeled oligonucleotides (Ready-To-Go T4 polynucleotide kinase; Amersham) at 30-35° C. overnight, washed three times (5 min each) in 2×SSC, 0.1% SDS at 30-35° C., and exposed to film. Alternatively, blots were probed with biotin-labeled oligonucleotides and analyzed using the Bio-Detect Kit (Ambion®). Densitometry analyses were performed using a bioimaging system (UVP) coupled with LabWorks software (UVP).

Quantitative Real-Time PCR Analyses

HEK293 cells grown in 24-well plates were transfected with 700 ng RNAi-expressing plasmids. At 48 h post-transfection, total RNA was isolated with 0.5 ml TRIzol® reagent (Invitrogen™), and random-primed first-strand cDNA synthesis was performed using 1 µg total RNA (TaqMan® reverse transcription reagents; Applied Biosystems) per manufacturer's protocol. Assays were performed on a sequence detection system using primers-probe sets specific for human HD, SCA1, GAPDH or 18S rRNA (Prism 7900HT and TaqMan® 2× Universal Master Mix; Applied Biosystems). Relative gene expression was determined by using the relative standard curve method.

GFP Silencing Analyses

HEK293 cells grown in 12-well plates were transfected with 1.2 µg and 300 ng of RNAi (SCA1 or GFP) and eGFP expression plasmids respectively. At 48 h post-transfection, fluorescent photomicrographs were captured at 4× magnification using an Olympus IX70 (microscope) and DP70 (camera) coupled with Olympus DP Controller software. Mean fluorescence in each image was determined using the histogram function in Image J software (NIH). Results for GFP RNAi-treated cells were normalized to control SCA1 RNAi-treated cells.

In Vitro Luciferase Assays

HEK293 cells grown in black 96-well plates (Costar 3603; Corning Inc.) were co-transfected in triplicate with RNAi-expressing plasmids (1-60 ng) and RNAi luciferase target plasmids (10-20 ng). In dosing studies, empty-vector was supplemented to low doses to match total DNA load. Firefly and *Renilla* luciferase activities were assessed 24 h post-transfection using the Dual-Glo Luciferase Assay System (Promega®) per manufacturer's instructions, using 50 µl per substrate. Luminescent readings were acquired with a 96-well plate luminometer (Dynex). Results were calculated as the quotient of *Renilla*/Firefly luciferase activities.

In Vivo Luciferase Assays

Animal studies were approved by the University of Iowa Animal Care and Use Committee. Eight-week old male C57/BL6 mice (Jackson Laboratories) were anesthetized with ketamine-xylazine and injected with 30 µl of 0.4 U/µl hyaluronidase (Sigma) into the tibialis anterior (TA) muscle. Two hours later, plasmids in 30 µl saline were injected into the TA muscle of re-anesthetized mice were. All groups (n=4 muscles) received 1 µg RNAi luciferase reporter plasmid along with 10 µg empty vector or RNAi plasmid (high dose) or 9 µg empty vector and 1 µg RNAi plasmid (low dose). Plasmids were prepared using the EndoFree® Plasmid Maxi Kit (Qiagen®). Plasmid-injected muscles were electroporated as previously described (McMahon et al., 2001, *Gene Ther* 8: 1264-1270) applying 175 V/cm in 10 20 ms pulses at 2 Hz (ECM 830 electroporator, BTX). At 4 and 8 days post-treatment, mice were sedated with isoflurane, and 30 µl of coelenterazine (0.3 mg/ml, Promega®) was injected into the TA muscles. Bioluminescence imaging was performed immediately using an IVIS200 imaging system (Xenogen). Light emissions were analyzed using Living Image software (Xenogen) and Igor Pro image analysis software (WaveMetrics Inc.). Data collected at 4 and 8 d revealed similar silencing trends (4 days not shown).

Statistical Analyses

Student's t-Test was used for all studies where P-values are provided. In all statistical analyses, P<0.05 was considered significant.

EXAMPLE 5

Artificial microRNAs Demonstrate Improved Safety Over Short-Hairpin RNAs

RNA interference (RNAi) is an evolutionarily conserved cellular process regulating gene expression and participating in innate defense. RNAi directs sequence-specific gene silencing by double-stranded RNAs (dsRNAs) that may be processed by Dicer into functional small RNAs, such as small interfering RNAs (siRNAs) and microRNAs (miRNAs) among others. Small RNAs associated with the RNA-induced silencing complex (RISC) or RISC-like complexes mediate post-transcriptional gene silencing by targeting transcripts for degradation or translational repression.

RNAi has been utilized as a biological tool to study gene function and is being developed as a therapeutic strategy to treat several diseases. Exogenous RNAi has been expressed in cell cultures and animals as short-hairpin RNAs (shRNAs) or artificial miRNAs, such as primary miRNA (pri-miRNAs) transcripts serving as siRNA shuttles. shRNAs are classically transcribed as sense and antisense sequences connected by a loop of unpaired nucleotides. Following transcription, shR-NAs are exported from the nucleus by Exportin-5, and processed by Dicer in the cytoplasm to generate functional siRNAs. miRNA stem-loops are typically expressed as part of larger pri-miRNA transcripts. These stem-loops are excised by the Drosha-DGCR8 generating intermediates known as pre-miRNAs, which are subsequently exported to the cytoplasm and diced into functional small RNAs.

While several studies from independent laboratories have demonstrated therapeutic efficacy of shRNAs in mouse models for neurological disease, few studies have rigorously evaluated the safety of RNAi vectors. To date, most expression-based RNAi strategies have utilized shRNAs expressed at high levels from strong Pol-III promoters. High levels of exogenously supplied RNAi substrates may cause cellular toxicity by various means. RNAi substrates may compete for endogenous RNAi machinery, thus disrupting natural miRNA biogenesis and function. Alternatively, shRNA expression can stimulate cellular responses to dsRNA, which may result in global gene silencing. Finally, toxicity may result from an increased likelihood of off-target silencing of unintended mRNAs due to partial complementarity with the seed region (positions 2-8, important for translational repression-based silencing) of antisense RNAs. These side-effects can produce severe cellular toxicity and even result in organismal death.

The inventors tested corresponding shRNA- and miRNA-based expression vectors which, upon processing, yield similar siRNA sequences with comparable strand-biasing. The inventors evaluated the safety of these vectors in vitro and in vivo and present data further supporting that artificial miRNAs show improved safety profiles over shRNAs. In addition, the inventors demonstrate that artificial miRNAs are effective in silencing a therapeutic target in a mouse model for neurodegenerative disease.

Results

Effects of Hairpin-Based RNAi Vectors on miRNA Biogenesis and Function

The inventors previously compared the efficacy of shRNAs and artificial miRNAs using a fair comparison scheme by minimizing the variables between the vectors (FIG. 29). They found shRNAs to be more potent; however, they noted that shRNAs are expressed at very high levels and yield an abundance of unprocessed precursors, whereas, artificial miRNAs are expressed at lower levels and processed efficiently. The inventors hypothesized that shRNAs saturate cellular RNAi processing machinery, and thus, are more prone to interfere with miRNA biogenesis and function.

Figure 30A:
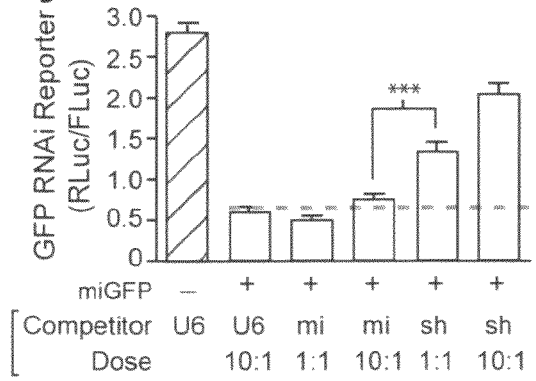
FIGS. 30A-30E.
Figure 30B:
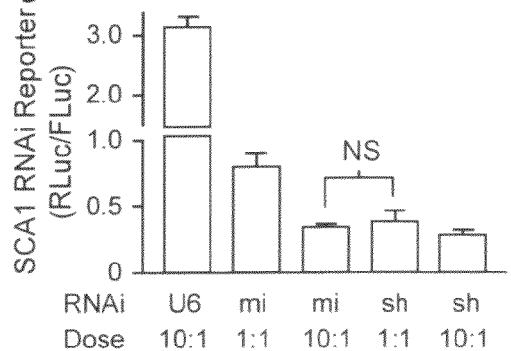
Figure 30C:
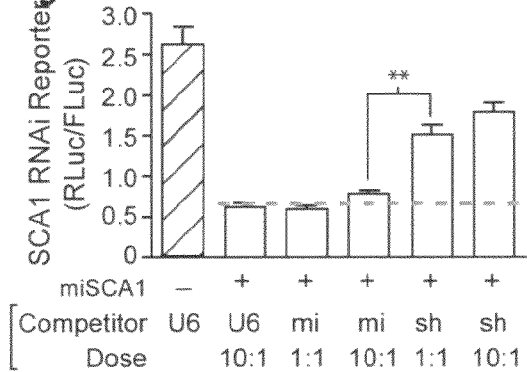
Figure 30D:
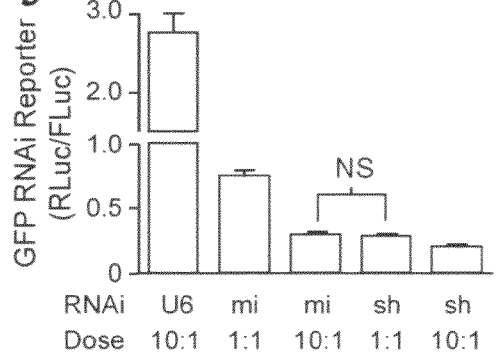

Initially, the relative safety of U6-driven shRNA- and miRNA-based RNAi vectors in vitro were tested by competition assay. The effects of these RNAi strategies on the processing and function of exogenously supplied artificial miRNAs were tested. This approach was used to simulate the processing of endogenous miRNAs while avoiding the possibility of having pre-processed mature miRNAs, which may be quite stable, present prior to the initiation of the experiment. In these studies, plasmids expressing miGFP and a GFP RNAi luciferase reporter, which contains a perfect target site for the GFP RNAi sequence, were co-transfected into HEK293 cells to establish baseline silencing mediated by a miRNA-based vector. Next, alleviation of silencing upon the co-expression of shSCA1 or miSCA1 competitors was evaluated to measure the potential interference imparted on miGFP activity. The inventors found that shSCA1 significantly decreases the function of miGFP (FIG. 30A). Notably, miSCA1, at a 10-fold higher dose, only slightly hindered miGFP activity. Interestingly, at this high dose, miSCA1 demonstrated similar silencing efficacy as the low dose of shSCA1 when targeting the SCA1 RNAi luciferase reporter in parallel experiments (FIG. 30B). These results were supported by reciprocal experiments where the effect of GFP RNAi competitors (shGFP or miGFP) on miSCA1 activity was evaluated in parallel with GFP RNAi efficacy studies (FIGS. 30C,D).

Figure 30E:
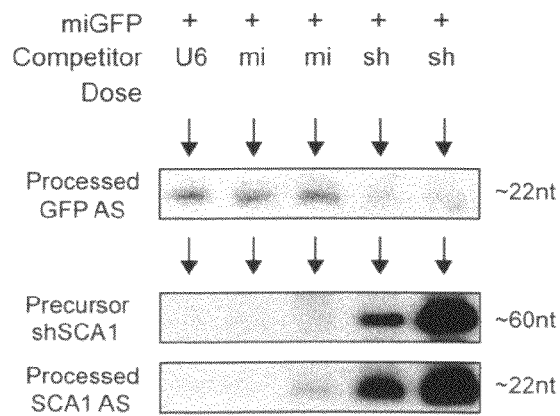

To evaluate whether shRNA expression disrupts miRNA biogenesis (e.g., by saturating Exportin-5 or Dicer) or function (e.g., by saturating RISC), the inventors performed northern blot analysis to assess the processing of miGFP in the presence of shSCA1 or miSCA1 competitors. They found that miGFP was appropriately processed to the mature form when co-expressed with miSCA1 competitors (FIG. 30E, top panel). Conversely, miGFP biogenesis was severely disrupted in the presence of shSCA1 expression vectors at low and high doses. This interference likely resulted from the robust shSCA1 expression which generated abundant precursor and processed forms relative to miSCA1 (FIG. 30E, bottom panels). These data, together with the inventors' gene silencing studies (FIG. 30B), suggest that maximal silencing can be achieved with miRNA-based approaches without build-up of undesired precursor and processed products which disrupt miRNA biogenesis and function.

Figure 31A:
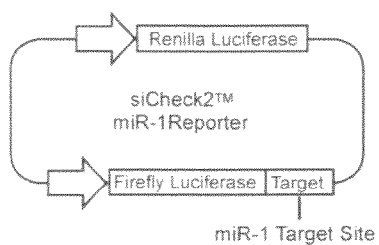
FIGS. 31A-31E.
Figure 31B:
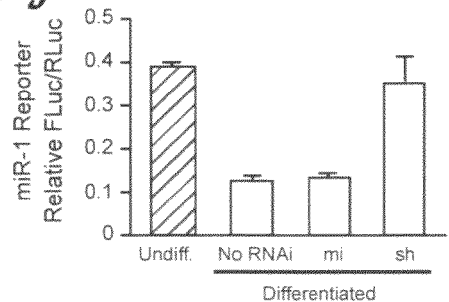

The inventors subsequently tested the effects of the shRNA- and miRNA-based RNAi strategies on endogenous miRNA biogenesis and function using mouse muscle-derived C2C12 cells, which upon differentiation induce expression of miR-1, a muscle-specific miRNA. This induction was evaluated by measuring the activity of a luciferase reporter for miR-1 function in undifferentiated and differentiated C2C12 cells (FIGS. 31A,B). Next, it was tested whether shSCA1 or miSCA1 expression disrupts the induction of miR-1 activity during differentiation. Consistent with our previous data, shSCA1 almost entirely inhibited miR-1 activation while miSCA1 expression had negligible effects (FIG. 31B).

Figure 31C:
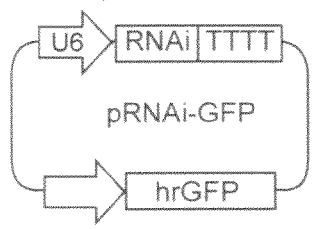
Figure 31D:
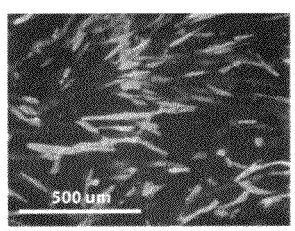
Figure 31E:
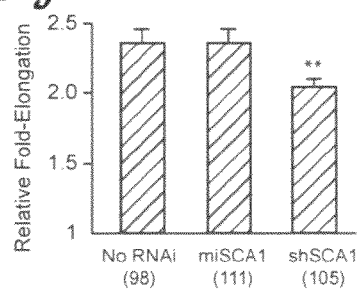

Inhibiting the function of muscle-specific miRNAs in differentiating C2C12 cells has been shown to disrupt the elongation process during myotubes formation. The inventors, therefore, measured the elongation of differentiated C2C12 cells following transfection with shRNA or artificial miRNA expression plasmids that co-express CMV-driven hrGFP (FIG. 31C). At 72 h post-treatment and differentiation, immunocytochemistry was performed to label myosin heavy-chain (MHC) to identify differentiating myotubes, and the relative lengths of MHC+/GFP+ cells were measured (FIG. 31D). The inventors found that the elongation process was significantly reduced in C2C12 cells transfected with shSCA1-expressing plasmids, but not those expressing miSCA1 (FIG. 31E, $P<0.01$).

Effects of Hairpin-Based RNAi Vectors on Cell Viability

Figure 32:
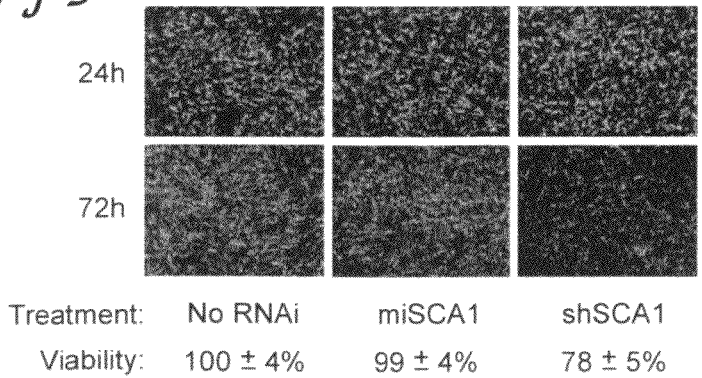
FIG. 32. The survival of RNAi-transfected C2C12 cells was assessed by monitoring the co-expression of hrGFP by fluorescence microscopy over time.

During the C2C12 studies, the inventors observed less overall hrGFP-positivity in shSCA1-treated cells at 72 h post-transfection. The inventors hypothesized that this loss was the result of shRNA-induced toxicity. Thus, the survival of RNAi-transfected C2C12 cells was assessed by monitoring the co-expression of hrGFP by fluorescence microscopy over a time-course (FIG. 32). At 24 h post-transfection, each treatment (No RNAi, miSCA1, or shSCA1) showed similar levels of fluorescence. However, at 72 h, the inventors noted a clear loss of hrGFP-positive cells in the shSCA1-treated population and no effect in either of the other treatment groups. At 72 hours post-treatment, the inventors also performed MTS assay to measure cell viability and found that shRNA-treated cells had approximately 20% reduced viability relative to No RNAi- or miRNA-treated cells (FIG. 32). Similar toxicity was observed at a 10-fold lower dose of shSCA1 (data not shown). Of note, the observed toxicity is not attributable to silencing endogenous mouse SCA1 in the C2C12 cells, as these RNAi sequences are specific for human SCA1.

Safety of Hairpin-Based RNAi Vectors in Mouse Cerebellum

Figure 33:
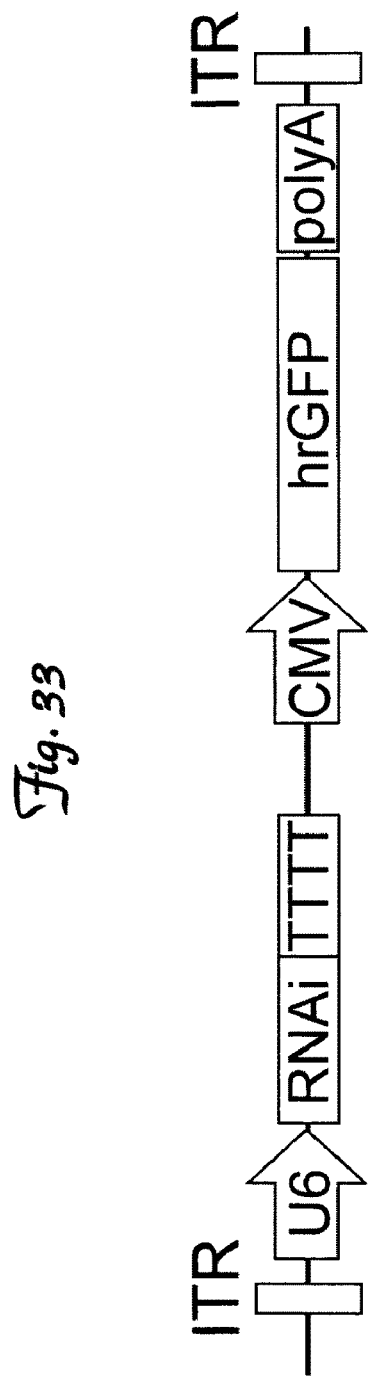
FIG. 33. This figure shows the generation of AAV serotype 2/1-expressing U6 driven shSCA1 or miSCA1.

Next, the inventors sought to test whether miRNA-based strategies show improved safety over shRNAs in vivo. The inventors focused their efforts on the cerebellum. They generated adeno-associated viral vectors (AAV serotype 2/1—FIG. 33A) expressing U6-driven shSCA1 or miSCA1. The AAV vectors also contain a hrGFP expression cassette for observing the distribution and types of cells transduced. Wild-type mice were injected with AAV1-hrGFP, AAV1-shSCA1, or AAV1-miSCA1 into the cerebellum and sacrificed 10 weeks later. Immunohistochemical analyses were performed for calbindin, which labels Purkinje cells within the molecular layer of the cerebellum. The inventors found that shSCA1 caused marked neurotoxicity, as evidenced by a clear loss of Purkinje cells in transduced (GFP-positive) regions of the cerebellum (FIGS. 33B,C). Conversely, AAV1-hrGFP- and AAV1-miSCA1-treated cerebella showed preserved integrity of Purkinje cells in transduced and untransduced regions (FIGS. 33B,C and data not shown). These results support that artificial miRNA expression in mouse cerebellum is well-tolerated, particularly when compared to the corresponding toxic shRNA.

Artificial miRNA-Mediated Silencing of a Therapeutic Target in Purkinje Cells

Previously the inventors found that shRNAs are more potent than artificial miRNAs when targeting co-transfected luciferase reporters or endogenous mRNAs in HEK293 cells. However, the present in vitro and in vivo safety analyses support the use of artificial miRNAs for developing vector-based RNAi therapeutics. As such, the inventors tested whether the potency of an artificial miRNA, miSCA1, is sufficient to silence its therapeutic target in a mouse model of spinocerebellar ataxia type I (SCA1) which expresses a mutant human ataxin-1 transgene via a Purkinje-cell specific promoter. SCA1 is a dominantly-inherited neurological disease which causes degeneration primarily in cerebellar Purkinje cells. The mutation responsible for the disease produces a toxic, polyglutamine-expanded form of ataxin-1, the SCA1 gene product, which localized to the nucleus.

Here, the inventors tested the capacities of the corresponding shSCA1 and miSCA1 vectors to silence the mutant human ataxin-1 transgene in SCA1 mice. Mice were injected with AAV1-shSCA1 or AAV1-miSCA1 into the cerebellum and histological analyses were performed seven weeks later to evaluate viral transduction (hrGFP), Purkinje cell integrity (calbindin) and gene silencing (ataxin-1). These analyses demonstrate that treatment with AAV1-miSCA1 effectively silences the SCA1 therapeutic target in Purkinje cells, as evidenced by a loss of nuclear ataxin-1 staining in regions positive for both hrGFP and calbindin. Conversely, shSCA1 expression caused neurotoxicity in SCA1 mice to a similar extent as previously observed in wild-type mice. The resulting loss of calbindin-positive Purkinje cells in shSCA1-treated cerebella likely explains the absence of ataxin-1 staining in these regions. These results demonstrate that artificial miRNAs are capable of silencing a candidate target for RNAi therapy in mouse cerebellum and provide additional support for the improved safety profile of artificial miRNAs over shRNAs.

Discussion

Here, the inventors demonstrate how the improved potency of shRNAs may be offset by toxicity issues. High levels of RNAi substrates produced by shRNA-expression vectors saturate cellular RNAi machinery, thus interfering with miRNA biogenesis and function in cell culture and in vivo. The present findings show that miRNA-based strategies are less prone to interfering with these processes in vitro, suggesting that artificial miRNAs may be less toxic. The inventors extend these findings to show that the shRNA-mediated interference occurs primarily at the level of miRNA biogenesis, though interference with the RISC is also probable. Furthermore, the inventors demonstrate that artificial miRNA expression may not disrupt cellular processes (i.e., myotube elongation) regulated by endogenous miRNAs nor cause cell death as compared to their corresponding shRNAs.

In vivo, shRNAs may cause toxicity in mouse striatum independent of HDh mRNA silencing. Similar to our work, others have observed acute liver toxicity and mortality in mice following systemic shRNA delivery (Grimm et al., 2006, *Nature* 441, 537-41). Importantly, this toxicity correlated with increased mature antisense RNA levels. However, there are important differences between our findings. First, Grimm et al. found that lowering the vector dose by approximately 10-fold significantly improved the lethal effects of some shRNAs on liver function and animal viability. In the present studies, reducing the dose led to lower transduction throughout the striatum, but did not abrogate toxicity. Second, the data by Grimm and colleagues show significant build-up of shRNA precursors in liver cells. They attributed the liver toxicity, in part, to disruption of endogenous miRNA biogenesis caused by shRNA saturation of RNAi nuclear export machinery. In the present work, the inventors detected abundant levels of unprocessed shRNAs in vitro, but interestingly, low to undetectable levels in vivo. This suggests that nuclear export was likely not limiting in the present studies. Alternatively, the striatal toxicity may be caused by excessive levels of mature antisense RNAs mediating off-target silencing of unintended mRNAs with partial complementarity.

Although understanding the mechanism of shRNA-induced toxicity in mouse striatum is important, the inventors focused on pursuing alternative RNAi strategies to alleviate the toxicity. They found that moving the HD2.4 and HD2.4mis sequences, both of which caused toxicity in the context shRNAs, into a miRNA scaffold significantly reduced neurotoxicity within the striatum with no sacrifice in gene silencing efficacy. The inventors correlated this positive effect to lower steady-state levels of mature antisense RNAs processed from the artificial mi2.4 relative to sh2.4. Whether this disparity in expression levels results from differences in transcription or stability between shRNAs and artificial miRNAs remains to be elucidated.

The improved safety profiles of miRNA-based RNAi strategies are exciting, particularly since in vivo gene silencing efficacy was not compromised relative to optimized shRNAs. These results support that we have saturated gene silencing on a per cell basis, as more antisense RNA did not increase silencing efficacy. Antisense RNA levels on a per cell basis may be further limited by adjusting the RNAi expression and viral delivery strategies. Conveniently, miRNA-based vectors are more amenable to Pol-II mediated transcription as compared to shRNAs, which have limited spacing flexibility for Pol-II based expression. Artificial miRNAs more naturally resemble endogenous RNAi substrates and are more amenable to Pol-II transcription (allowing tissue-specific expression of RNAi) and polycistronic strategies (allowing delivery of multiple siRNA sequences). This advantage allows for regulated and cell-specific expression of inhibitory RNAs. These versatile expression strategies enhance the application of as biological tools and may further limit potential toxicity in therapeutic applications. For these reasons, in addition to the present findings, artificial miRNAs are more suitable for the development of vector-based RNAi therapeutics.

Material and Methods
Vectors

Plasmids expressing U6-driven artificial miRNAs or shRNA vectors targeting SCA1 have been previously described along with the SCA1 and GFP RNAi luciferase reporter plasmids. The miR-1 Firefly luciferase reporter was cloned using a similar strategy. Briefly, a single site with perfect complementarity to miR-1 was inserted into the 3'UTR of Firefly luciferase (psiCheck™2, Promega®) using a tailed-PCR strategy with the following primers: forward—5'-AAAATCTAGATACATACTTCTTTACAT-TCCACCGCTTCGAGCAGACATG-3' (SEQ ID NO:213), reverse—5'-AAAAGGATCCTCGAGCGATTTTACCA-CATTTGTAGAGG-3' (SEQ ID NO:214). This PCR product was digested with XbaI-BamHI and cloned into the same sites within psiCheck™2. For C2C12 and AAV vector production, miRNA or shRNA expression cassettes driven by the mouse U6 promoter were cloned into a derivative of the pFBGR plasmid upstream of a CMV-hrGFP-SV40 polyA expression cassette.

In Vitro Luciferase Assays

HEK293 cells grown in black 96-well plates (Costar 3603; Corning Inc.) were co-transfected in triplicate with RNAi-expressing plasmids (10 to 100 ng) and RNAi luciferase target plasmids (10 to 20 ng). In dosing studies, empty-vector was supplemented to low doses to match total DNA load. Firefly and *Renilla* luciferase activities were assessed 24 h post-transfection using the Dual-Glo Luciferase Assay System (Promega®) per manufacturer's instructions, using 50 µl per substrate. Luminescent readings were acquired with a 96-well plate luminometer (Dynex). Results were calculated as the quotient of *Renilla*/Firefly luciferase activities.

For C2C12 studies, cells grown in 24-well plates coated with poly-1-ornithine (0.1 mg/ml, Sigma) were transfected in quadruplicate with 200 ng of endotoxin-free RNAi or empty-vector plasmids along with 40 ng of siCheck™2 or miR-1 luciferase reporter (target site in 3'UTR of Firefly luciferase) plasmids. Cells were differentiated by serum-starvation at 4 h post-transfection, and Dual Luciferase assays (Promega®) were performed 48 h later with a 96-well plate luminometer (Berthold Technologies). Of note, undifferentiated samples were harvested at 24 h post-transfection as cells were nearing 100% confluence. Results were calculated as the quotient of Firefly/*Renilla* luciferase activities.

Northern Blot Analyses

HEK293 cells grown in 6-well plates were transfected with RNAi plasmids (0.2 or 2 µg SCA1 RNAi with 1.5 µg miGFP for competition studies or 0.2 or 2 µg HD2.4 RNAi). Empty-vector plasmid was supplemented to low doses to match total DNA load. Total RNA was isolated at 48 h post-transfection using 1 ml TRIzol® reagent (Invitrogen™), and 15-20 µg was resolved on a 15% acrylamide gel. Small transcript sizes were determined with the Decade Ladder (Ambion®). Loading was assessed by ethidium bromide stain. RNA was transferred to Hybond™-XL membrane (Amersham) and UV-crosslinked. Blots were pre-hybridized using UltraHyb®-Oligo (Ambion®) at 35° C., probed with $\gamma$-$^{32}$P-labeled oligonucleotides (Ready-To-Go T4 polynucleotide kinase; Amersham) at 30-35° C. overnight, washed in 2×SSC, 0.1% SDS at 30-35° C., and exposed to film.

For in vivo studies, total RNA from striatal tissue punches was harvested using 1 ml TRIzol® reagent (Invitrogen™). Northern blots were performed as indicated above using 1-3 µg RNA.

C2C12 Elongation Analyses

C2C12 cells grown in 24-well plates coated with poly-1-ornithine (0.1 mg/ml) were transfected with 200 ng of empty-vector or RNAi plasmids co-expressing hrGFP or differentiated after 4 h. At 72 h, cells were washed twice with PBS and fixed in 4% formaldehyde for immunocytochemistry (done at room temperature). Alternatively, undifferentiated cells were fixed at 24 h post-transfection. Fixed cells were incubated in blocking buffer (2% bovine albumin, 2% horse serum, 0.1% NP-40 in PBS) for 30 min. Anti-myosin heavy-chain (MHC) primary antibody (1:1000, MF20 from the University of Iowa Hybridoma Facility) was added with fresh blocking buffer and incubated for 2 h. Cells were then washed twice with PBS, incubated with an Alexa-568-conjugated anti-mouse IgG (1:5000, Invitrogen™) for 30 min, and washed again with PBS. Fluorescence microscopy images (red-MHC and green-hrGFP) were captured at 10× magnification using an Olympus IX70 (microscope) and DP70 (camera) coupled with Olympus DP Controller software. Corresponding images were overlayed, and the lengths of GFP+/MHC+ cells were quantified using Image J software (NIH).

C2C12 Survival Studies

Cells grown in 24-well plates coated with poly-1-ornithine (0.1 mg/ml) were transfected in triplicate with 400 ng of endotoxin-free empty-vector or RNAi plasmids co-expressing hrGFP and differentiated after 4 h. At 24 h and 72 h post-transfection, fluorescence microscopy images were captured at 4× magnification using an Olympus IX70 (microscope) and DP70 (camera) coupled with Olympus DP Controller software. At 72 h, cells were trypsinized, resuspended in 1 ml of growth media, and 100 µl aliquots (in triplicate) were analyzed using the CellTiter-96 AQueous MTS assay (Promega®) per manufacturer's instructions. Absorbance was measured with a 96-well microplate reader (Molecular Devices) and normalized to cells treated with empty-vector.

Viral Vector Production and Purification

Recombinant AAV vectors were produced by a standard calcium phosphate transfection method in adherent HEK293 cells, using the Ad helper, trans-packaging and AAV vector plasmids as previously described. Vector titers were determined by QPCR, using a Prism 7900 sequence detector (Applied Biosystems), and were between 3 and $10\times10^{12}$ DNase-resistant particles (DRP)/ml (later referred to as viral genomes/ml). Viral infectivity was assessed in a TCID50 assay using the HeLa-based B50 cell line. AAV1.mi2.4, AAV1.mi2.4mis, AAV1.sh2.4 and AAV1.GFP were produced by Targeted Genetics Incorporated, and AAV1.miSCA1 and AAV1.shSCA1 were provided by the University of Iowa Vector Core facility.

AAV Injections

All animal protocols were approved by the University of Iowa Animal Care and Use Committee. Eight-week old C57/BL6 mice (Jackson Laboratories) were injected with AAV2/1-expressing shRNAs or miRNAs and sacrificed 16 weeks later. Mice were anesthetized with xylazine (100 mg/kg) and ketamine (10 mg/kg), their heads shaved, sterilized with betadine and placed in a Kopf stereotaxic frame specially adapted for mouse surgery. A midline incision was made and unilateral burr holes were created over the right striatum with a high-speed dental drill. Subsequently, 5 µl of either AAV1.sh2.4, AAV1.mi2.4 or AAV1.mi2.4mis ($4\times10^{12}$ viral genomes/ml) was injected into the right striatum (coordinates: 0.86 mm rostral to bregma, 1.8 mm lateral to midline, 3.5 mm ventral to the skull surface). All injections were performed through a 10 µl Hamilton syringe connected to an infusion pump at a rate of 0.2 µl/min with a 33-gauge, blunt tipped needle. The needle was left in situ for an additional 5 min to allow the injectate to diffuse from the needle tip. The scalp was closed with 5-0 polyvicryl suture. For cerebellar studies in SCA1 mutant mice, 1 µl of either AAV1.shSCA1 or AAV1.miSCA1 ($1\times10^{12}$ viral genomes/ml) was injected into the cerebellum (coordinates: 6.0 mm caudal to bregma, 2.0 mm lateral to midline, 1.0 mm ventral to the skull surface) as described above using a Hamilton syringe cemented with a glass micropipette tip.

Sacrifice

Mice used in histological analyses were anesthetized with a ketamine/xylazine mix and transcardially perfused with 20 ml of 0.9% cold saline, followed by 20 ml of 4% paraformaldehyde in 0.1M $PO_4$ buffer. Mice were decapitated, the brains removed and post-fixed overnight. Brains were stored in a 30% sucrose solution at 4° C. until cut on a sliding knife microtome at 40-µm thickness and stored at −20° C. in a cryoprotectant solution. Mice used for biochemical analysis were perfused with 20 ml of 0.9% cold saline. Brains were removed and sectioned into 1 mm thick coronal slices using a brain matrix (Roboz). Tissue punches were taken from the striatum using a tissue core (1.4 mm in diameter) and triterated in 50 µl of TRIzol (Invitrogen™).

Quantitative Real-Time PCR (QPCR)

For in vitro studies, HEK293 cells grown in 24-well plates were transfected with 700 ng of HD2.4 RNAi expression plasmids and cells harvested 48 h later. RNA was isolated from HEK293 cells or striatal tissue punches using 1 ml of TRIzol reagent (Invitrogen™). Random-primed first-strand cDNA synthesis was performed using 500 ng total RNA (TaqMan® reverse transcription reagents; Applied Biosystems) per manufacturer's protocol. Assays were performed on a sequence detection system using primers-probe sets specific for human HD and GAPDH or mouse HDh, CD11b (Itgam) and β-actin (Prism 7900HT and TaqMan® 2× Universal Master Mix; Applied Biosystems). Relative gene expression was determined by using the $\Delta\Delta C_T$ method, normalizing to either GAPDH or β-actin mRNA levels.

Immunohistochemical Analyses

Free-floating, coronal brain sections (40 µm thick) were processed for immunohistochemical visualization of striatal neurons (DARPP-32, 1:100, Cell Signaling Technology), microglia (Iba1, 1:1000, WAKO), cerebellar Purkinje cells (Calbindin, 1:2000, Cell Signaling Technology), or mutant human ataxin-1 (11NQ). Sections were first incubated in 0.1 M sodium periodate in Tris-buffered saline (TBS) for 20 min to remove endogenous peroxidase activity and then blocked with 5% normal goat serum for 1 h. After blocking, sections were incubated with primary antibody for 24 h, washed, and then incubated with biotin- or Cy3-labeled goat anti-rabbit IgG secondary antibodies (1:200, Vector Laboratories and Jackson Immunoresearch) for 1 h. Sections were washed again and placed in Vectastain ABC-peroxidase reagent (Vector Laboratories) for 1 h. Sections were then washed and incubated in a chromagen solution containing 0.05% 3,3'-diaminobenzidine tetrahydrochloride and 0.005% hydrogen peroxidase for up to 5 min. All staining procedures were carried out at room temperature and deletion of the primary antibody served as a control. Sections were mounted onto Superfrost™ Plus slides (Fisher Scientific) and coverslipped with Gelmount (Biomeda). Images were captured using an Olympus BX60 light microscope and DP70 digital camera, along with Olympus DP Controller software.

Statistical Analyses

Student's t-Test was used for all studies, unless indicated otherwise. For C2C12 elongation analyses, a one-way analysis of variance (ANOVA) was performed followed by Bonferroni post-hoc analyses to assess for significant differences between individual groups. In all statistical analyses, P<0.05 was considered significant.

Vector Design

An expression cassette (5'NheI-3'BglII) containing the CMV promoter, multiple cloning site (MCS) and SV40 polyadenylation (polyA) signal was cloned into TOPO-BluntII (XbaI-BamHI, Invitrogen™) in reverse orientation. A Pol-III expression cassette containing mouse U6 promoter, MCS and Pol-III-terminator (6T's) was cloned into TOPO-BluntII with the same strategy. Artificial miRNAs were generated by polymerase extension of overlapping DNA oligonucleotides (IDT). Polymerase-extended products were digested with XhoI-SpeI and cloned into the MCS of the expression vectors XhoI-SpeI (miV1) or XhoI-XbaI (miV2). miV3 resulted from an unexplained cloning error. Other shRNAs were cloned using a tailed-PCR strategy. PCR products containing U6-shRNA-6T's were TOPO cloned into the BluntII vector and positive clones were considered to be in reverse orientation to maintain consistency with the other expression vectors.

For in vivo studies, miRNA or shRNA expression cassettes driven by the mouse U6 promoter were cloned in the same orientation upstream of a CMV-hrGFP-SV40polyA expression cassette.

RNAi luciferase reporter vectors were constructed using psiCheck2™ (Promega®). Tailed-PCR was used to amplify a 3' fragment of *Renilla* luciferase containing a single, perfect complementary RNAi target site (~25-bp: 21-bp target+2-nt 5' and 3') downstream of the stop codon. This PCR product was digested with AatII-XhoI and cloned into the same sites within psiCheck™2.

See FIG. 31 for detailed information about vector construction.

Northern Blot Analyses

HEK293 cells grown in 6-well plates were transfected with 1.5 µg of RNAi expression plasmid. Total RNA was isolated at 48 h post-transfection using 1 ml TRIzol® reagent (Invitrogen™); alternatively, the small RNA fraction was harvested using mirVana™ Isolation Kit (Ambion®). 15-20 µg total RNA or 1-2 µg small RNA fraction was resolved on a 15% acrylamide gel. Small transcript sizes were determined with the Decade Ladder (Ambion®). Consistent loading and RNA integrity was assessed by ethidium bromide stain. RNA was transferred to Hybond-XL membrane (Amersham Pharmacia) at 200-400 mA for 1-2 h and UV-crosslinked with the auto-crosslink function on a Stratalinker 1800 (Stratagene®). Blots were pre-hybridized using UltraHyb-Oligo (Ambion®) at 35° C., probed with $^{32}$P-labeled oligonucleotides (Ready-To-Go T4 polynucleotide kinase; Amersham) at 30-35° C. overnight, washed three times (5 min each) in 2×SSC, 0.1% SDS at 30-35° C., and exposed to film. Alternatively, blots were probed with biotin-labeled oligonucleotides and analyzed using the Bio-Detect Kit (Ambion®). Densitometry analyses were performed using a bioimaging system (UVP) coupled with LabWorks software (UVP).

Quantitative Real-Time PCR Analyses

HEK293 cells grown in 24-well plates were transfected with 700 ng RNAi-expressing plasmids. At 48 h post-transfection, total RNA was isolated with 0.5 ml TRIzol® reagent (Invitrogen™), and random-primed first-strand cDNA synthesis was performed using 1 µg total RNA (TaqMan® reverse transcription reagents; Applied Biosystems) per manufacturer's protocol. Assays were performed on a sequence detection system using primers-probe sets specific for human HD, SCA1, GAPDH or 18S rRNA (Prism 7900HT and TaqMan 2×Universal Master Mix; Applied Biosystems). Relative gene expression was determined by using the relative standard curve method.

GFP Silencing Analyses

HEK293 cells grown in 12-well plates were transfected with 1.2 µg and 300 ng of RNAi (SCA1 or GFP) and eGFP expression plasmids respectively. At 48 h post-transfection, fluorescent photomicrographs were captured at 4× magnification using an Olympus IX70 (microscope) and DP70 (camera) coupled with Olympus DP Controller software. Mean fluorescence in each image was determined using the histogram function in Image J software (NIH). Results for GFP RNAi-treated cells were normalized to control SCA1 RNAi-treated cells.

In Vitro Luciferase Assays

HEK293 cells grown in black 96-well plates (Costar 3603; Corning Inc.) were co-transfected in triplicate with RNAi-expressing plasmids (1-60 ng) and RNAi luciferase target plasmids (10-20 ng). In dosing studies, empty-vector was supplemented to low doses to match total DNA load. Firefly and *Renilla* luciferase activities were assessed 24 h post-transfection using the Dual-Glo Luciferase Assay System (Promega®) per manufacturer's instructions, using 50 µl per substrate. Luminescent readings were acquired with a 96-well plate luminometer (Dynex). Results were calculated as the quotient of *Renilla*/Firefly luciferase activities.

In Vivo Luciferase Assays

Animal studies were approved by the University of Iowa Animal Care and Use Committee. Eight-week old male C57/BL6 mice (Jackson Laboratories) were anesthetized with ketamine-xylazine and injected with 30 µl of 0.4 U/µl hyaluronidase (Sigma) into the tibialis anterior (TA) muscle. Two hours later, plasmids in 30 µl saline were injected into the TA muscle of re-anesthetized mice were. All groups (n=4 muscles) received 1 µg RNAi luciferase reporter plasmid along with 10 µg empty vector or RNAi plasmid (high dose) or 9 µg empty vector and 1 µg RNAi plasmid (low dose). Plasmids were prepared using the EndoFree® Plasmid Maxi Kit (Qiagen). Plasmid-injected muscles were electroporated as previously described applying 175 V/cm in 10 20 ms pulses at 2 Hz (ECM 830 electroporator, BTX). At 4 and 8 d days post-treatment, mice were sedated with isoflurane, and 30 µl of coelenterazine (0.3 mg/ml, Promega®) was injected into the TA muscles. Bioluminescence imaging was performed immediately using an IVIS200 imaging system (Xenogen). Light emissions were analyzed using Living Image software (Xenogen) and Igor Pro image analysis software (WaveMetrics Inc.). Data collected at 4 and 8 d revealed similar silencing trends (4 d not shown).

Statistical Analyses

Student's t-Test was used for all studies where P-values are provided. In all statistical analyses, P<0.05 was considered significant.

EXAMPLE 6

Artificial miRNAs Mitigate shRNA-Mediated Toxicity in the Brain: Implications for the Therapeutic Development of RNA Interference The ability of small interfering RNAs (siRNAs) to silence target genes was first demonstrated in 1998 and has since emerged as a revolutionary strategy to reduce target gene expression. RNAi occurs naturally in cells as a post-transcriptional regulatory mechanism mediated by endogenous miRNAs. RNAi is hypothesized to have evolved as a cellular coping mechanism providing the cell a means to decrease the expression of various deleterious viruses and transposons. In recent years, scientists have co-opted this biological process to reduce expression of target mRNAs using exogenously applied siRNAs, shRNAs or artificial miRNAs. Aside from the widespread basic biological applications of RNAi, the ability to reduce gene expression marks a major advance towards the development of disease therapies, particularly for dominantly inherited disorders.

Among the dominant diseases that may benefit from RNAi-based therapies is Huntington's disease (HD). Partial reduction of mutant huntingtin expression by viral delivery of shRNAs is efficacious in preventing the development of motor deficits and neuropathology in transgenic mouse models of HD. In proof-of-principal studies, the therapeutic effect on disease phenotype was studied by knocking down a mutant human HD transgene in the setting of two normal mouse HDh alleles. While allele-specific targeting of disease transcripts for HD therapy would be ideal, to date, no prevalent single nucleotide polymorphism (SNP) residing on the mutant transcript has been identified. Therefore, the inventors undertook studies to identify inhibitory RNAs that would target both mouse HDh and human HD transcripts, with the intention of testing the efficacy of reducing expression of both alleles in a knock-in model of HD. This example describes the surprising finding of neurotoxicity in mouse brain caused by some, but not all, shRNA expression vectors screened in vivo, and the notable reduction in toxicity after moving those toxic inhibitory RNAs into miRNA-based delivery systems.

Results shRNAs Cause Striatal Toxicity in Mice

Figure 35A:
FIGS. 35A-35C. In vitro screening of shRNAs targeting human HD and mouse HDh transcripts.
Figure 35B:
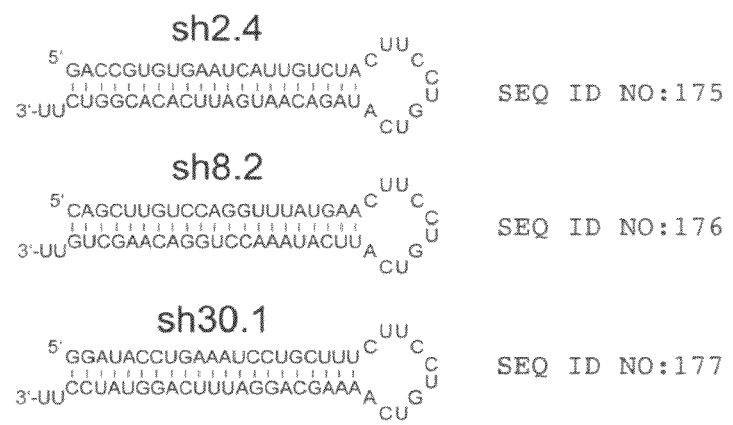
Figure 35C:
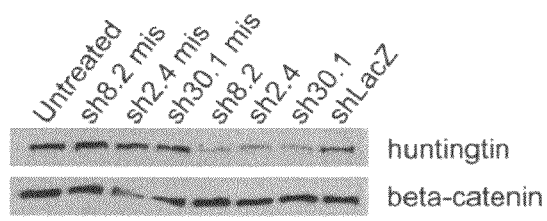

First shRNAs (driven by the mouse U6 promoter) that target conserved sequences spanning human HD and mouse HDh mRNAs were designed and screened (FIGS. 34 and 35A). Silencing of HD mRNA measured by quantitative real-time PCR (QPCR) and dot blot analysis revealed a decrease in huntingtin protein expression following transfection of shRNA expression plasmids into mouse C2C12 and human-derived HEK293 cell lines (data not shown). Of the 35 shRNAs tested, 3 were chosen for further study based on silencing efficacy. The shRNAs target sequences in exons 2, 8 and 30 of HD mRNAs, and are henceforth referred to as sh2.4, sh8.2 and sh30.1, respectively (FIG. 35B). Western blot analysis demonstrated that these shRNAs, but not mismatch (mis) control shRNAs, reduce endogenous huntingtin protein expression in mouse C2C12 cells (FIG. 35C). Similar results were seen in human-derived HEK 293 cells.

Figure 36A:
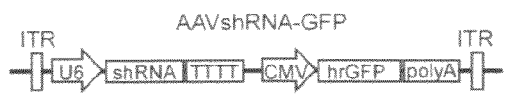
FIGS. 36A-36D. HD shRNAs cause sequence-specific striatal toxicity in mice.
Figure 36B:
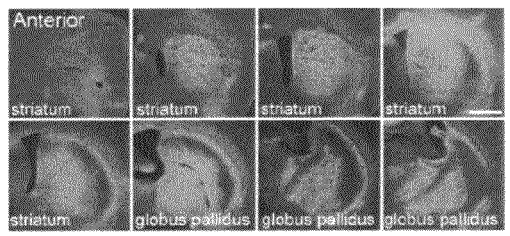
Figure 36C:
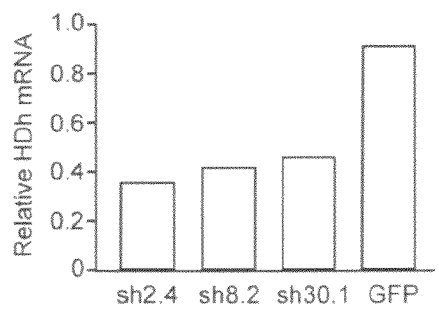
Figure 37:
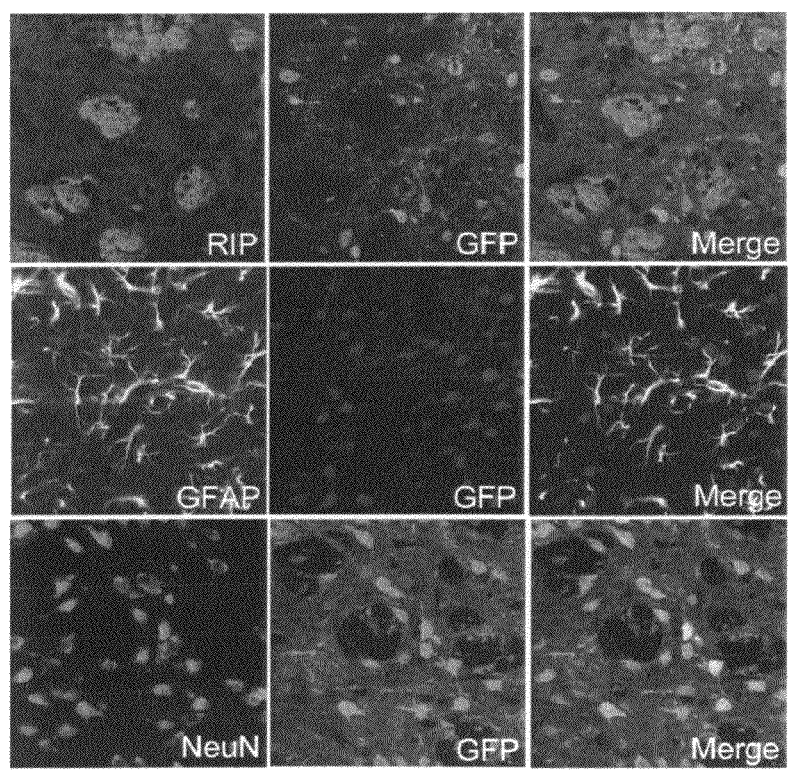
FIG. 37. GFP-positive cells co-localize with neurons in the striatum. Immunofluorescent staining of GFP-positive cells (autofluorescence) throughout the striatum co-labeled with either RIP (top panel, oligodendrocyte marker), GFAP (middle panel, astrocyte marker) or NeuN (bottom panel, neuronal marker). Scale bar=20 um for each photomicrograph.

To examine the long-term effects of brain-delivered shRNAs in the CAG140 knock-in mouse model, U6-shRNA expression cassettes were cloned into adeno-associated viral vectors (AAV serotype 2/1—FIG. 36A). AAVs also contained a humanized *Renilla* green fluorescence protein (hrGFP) expression cassette to identify the distribution and types of cells transduced. Five-week old CAG140 knock-in mice were injected bilaterally into the striatum with AAVsh2.4-GFP, AAVsh8.2-GFP, AAVsh30.1-GFP or AAV-GFP (viral control) and sacrificed 15 weeks later. Robust expression of GFP was observed in cells throughout the rostral/caudal extent of the striatum and within fibers of the globus pallidus (FIG. 36B). Immunofluorescence analyses indicated that GFP-positive cells co-localized with a neuronal marker (NeuN) but not with markers for astrocytes (GFAP) or oligodendrocytes (RIP1) (FIG. 37). QPCR performed on RNA isolated from GFP-positive striatal tissue showed a significant and statistically similar reduction of HDh mRNA expression (~60%) among the different active shRNA-expressing vectors compared to mice injected with AAV-GFP (FIG. 36C, $F(3,11)=32.3$, $P<0.001$ for post-hoc analyses comparing each AAV-shRNA group to the AAV-GFP control). Moreover, western blot analysis demonstrated a significant reduction in huntingtin protein levels following AAVshRNA-GFP administration compared to controls (FIG. 37, $t(8)=3.9$, $P<0.01$).

Figure 36D:
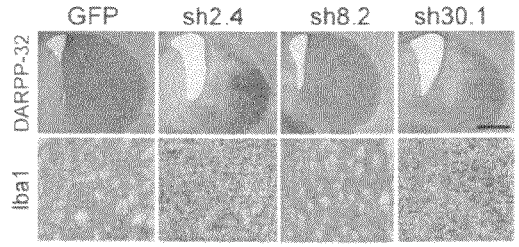

Unexpectedly, immunohistochemical analyses for dopamine- and cAMP-regulated protein (DARPP-32), a marker of medium-sized spiny projection neurons in the striatum, revealed striatal toxicity in mice injected with AAVsh2.4-GFP and AAVsh30.1-GFP (FIG. 36D, top panel). Reduction in DARPP-32 immunoreactivity was largely confined to the transduced (GFP-positive) regions of the striatum. Interestingly, this toxicity was not seen in mice injected with AAVsh8.2-GFP (FIG. 36D, top panel); striata from these mice were similar to AAV-GFP-injected control mice.

To assess whether the observed loss of DARPP-32 staining was associated with microglial activation, tissue sections were stained with an anti-Iba1 antibody to identify both resting and reactive microglia throughout the brain. AAVsh2.4-GFP and AAVsh30.1-GFP-injected striata demonstrated high Iba1 expression, whereas AAVsh8.2-GFP-injected striata were similar to control mice (FIG. 36D, bottom panel). Moreover, AAVsh2.4-GFP- and AAVsh30.1-GFP-injected mice demonstrated dramatic reactive astrogliosis compared to AAVsh8.2-GFP and control-injected mice, as evidenced by robust GFAP staining in areas of the striatum corresponding to high GFP positivity (data not shown). Notably, a mismatch control for the 2.4 sequence, AAVsh2.4mis-GFP, induced toxicity similar to sh2.4 and sh30.1, without reducing HDh mRNA expression. This, in addition to the sh8.2 data, indicates that three (two active, one inactive) of four shRNAs were toxic and that toxicity is not caused by silencing huntingtin.

Although all U6-shRNA expression cassettes were cloned into the same viral vector, the inventors tested for the possibility that toxicity correlated with steady-state levels of the expressed products. RNA samples harvested from shRNA-treated striata were analyzed by small transcript northern blot probing for the mature antisense (AS) and sense (S) RNAs generated by the respective shRNAs. Results demonstrate that sh2.4 AS RNA and sh30.1 AS RNA are expressed more robustly than sh8.2 AS RNA (n=2 per group, FIG. 38), thus correlating toxicity with increased expression levels of the shRNAs in vivo. The disparity in expression levels is interesting, particularly given the fact that each shRNA was designed using the same rules, injected at the same viral dose, driven by the same Pol-III promoter and silenced HDh mRNA to a similar degree. Notably, the sense strands and pre-processed products for the shRNAs were not detectable in brain lysates, suggesting that the toxicity is due, in part, to high levels of inhibitory RNAs rather than inappropriate sense strand loading into the RNA-induced silencing complex (RISC).

Artificial miRNAs are Expressed at Lower Levels Relative to shRNAs

Because the toxic shRNAs were expressed at higher levels than the non-toxic, active hairpin, an approach to reduce toxicity would be to lower the viral titer injected. In brain, decreasing the titers by a half log ($1e^{12}$) or a full log ($5e^{11}$) achieved silencing of HDh mRNA (47% and 51%, respectively) but did not alleviate striatal toxicity (FIG. 39). Decreasing the titers even further ($1e^{11}$ or $5e^{10}$) reduced the silencing efficacy to 15% of controls, making it non-viable as a therapeutic (FIG. 39). Thus, the inventors tested if levels of inhibitory RNAs could be minimized without compromising silencing efficacy using an artificial miRNA as a siRNA shuttle (versus a shRNA).

As shown in Example 4 above, artificial miRNAs effectively silence target gene expression relative to shRNAs, without generating excessive levels of inhibitory RNAs. Consequently, the inventors cloned two of the toxic sequences (HD2.4 and HD2.4mis) into an artificial miRNA scaffold based on human miR-30, thus creating mi2.4 and mi2.4mis (FIG. 40A). Expression levels of mi2.4 and sh2.4 were first compared by small transcript northern blot analysis at 48 h post-transfection of RNAi-expressing plasmids into HEK 293 cells. Probing for the HD2.4 antisense strand revealed that mi2.4 produces substantially lower levels of inhibitory RNAs relative to sh2.4. Notably, sh2.4 generates an abundance of precursor and processed RNAs, even at a 10-fold lower dose (FIG. 40B). Despite the dramatic difference in expression levels, mi2.4 reduced endogenous HD transcripts almost as effectively as sh2.4 (50% and 60% silencing, respectively) in HEK 293 cells (FIG. 40C).

Artificial miRNAs Mitigate Striatal Toxicity in Mice

Next AAV2/1-expressing mi2.4 or the mi2.4 mismatch control were generated (FIG. 36B, 40A) to test whether the development of striatal toxicity could be prevented relative to AAVsh2.4-GFP. Because shRNA-induced toxicity was not dependant on the disease model, subsequent studies were performed in wild-type mice. Mice were injected into the right striatum with AAVsh2.4-GFP, AAVmi2.4-GFP or AAVmi2.4mis-GFP and sacrificed 4 months post-injection. The time-course, volume and titer were identical to those used in our earlier shRNA studies (FIG. 36). QPCR performed on RNA isolated from mouse striata showed a statistically significant reduction of HDh mRNA (~70%) following treatment with either sh2.4- or mi2.4-expressing vectors compared to uninjected striata or striata treated with mi2.4mis (FIG. 39A, $F(2,8)=77.6$, $P<0.001$ for post hoc analyses comparing sh2.4 and mi2.4 versus uninjected and mi2.4mis). Importantly, the degree of HDh mRNA silencing between sh2.4 and mi2.4 was similar and not significantly different ($P>0.05$). Additional QPCR analyses were performed on these samples to measure CD11b mRNA, a readout for microglial activation, as an initial assessment for toxicity. Striata treated with sh2.4 showed nearly a 4-fold increase of CD11b mRNA relative to uninjected striata, while mi2.4- and mi2.4mis-treated striata showed only minimal induction (FIG. 5B, $F(2,8)=23.6$, $P<0.001$ for post-hoc analyses comparing sh2.4 to all other groups). To determine if these differences in toxicity could be attributed to levels of HD2.4 inhibitory RNAs, the inventors performed northern blot analysis on the same RNA samples used for the QPCR analyses. Although silencing efficacies between the sh2.4- and mi2.4-treated groups were comparable, northern blot analysis, probing for the HD2.4 antisense strand, demonstrated considerably more mature antisense RNAs in sh2.4-treated mice relative to mi2.4-treated mice (FIG. 39C). These results corroborate our in vitro findings and correlate the improvement in toxicity with reduced levels of HD2.4 antisense RNA.

Figure 41:
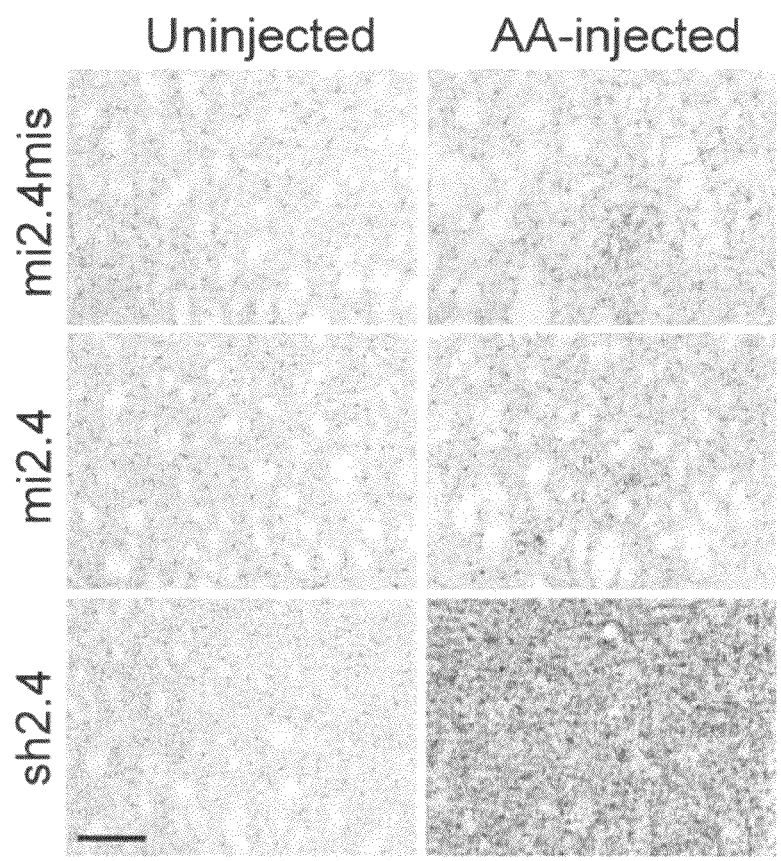
FIG. 41. Increased microglial activation in AAVsh2.4-GFP treated mice. Immunohistochemistry for the microglia marker, IbaI, performed on striatal tissue sections from mice injected with either AAVsh2.4-GFP (bottom panel), AAVmi2.4-GFP (middle panel) or AAVmi2.4mis-GFP (top panel). Both the AAV-injected (right panel) and uninjected (left panel) hemispheres are shown. Scale bar=100 um for each photomicrograph.

The inventors further assessed striatal toxicity by histological analyses. Immunolabeling for DARPP-32 expression revealed significant attenuation of striatal toxicity in AAVmi2.4-GFP-injected cohorts relative to AAVsh2.4-GFP-injected mice (FIG. 39D, middle panel). Moreover, the intense microglial activation (Iba1 positive cells) seen in AAVsh2.4-GFP-injected mice was scarcely present in AAVmi2.4-GFP-injected mice (FIG. 39D, lower panel and FIG. 41). Of note, mi2.4mis-treated brains also showed no apparent toxicity by these analyses, whereas, 2.4mis was toxic when delivered as a shRNA. Thus, sequences encoding HD2.4 and HD2.4mis were toxic in the setting of a shRNA in brain, but not in the context of a miRNA scaffold.

Discussion

Here, it has been show that some shRNAs cause toxicity in mouse striatum independent of HDh mRNA silencing. Similar to the present work, Grimm and colleagues observed acute liver toxicity and mortality in mice following systemic shRNA delivery, which correlated with increased mature antisense RNA levels (Grimm et al., 2006, Nature 441, 537-41). However, there are important differences between the present findings. First, Grimm et al. found that lowering the vector dose by approximately 10-fold significantly improved the lethal effects of some shRNAs on liver function and animal viability. In the present studies, reducing the dose led to lower transduction throughout the striatum, but did not abrogate toxicity. Second, the data by Grimm and colleagues show significant build-up of shRNA precursors in liver cells. They attributed the liver toxicity, in part, to saturation of endogenous RNAi export machinery. In the present work, the inventors detected abundant levels of unprocessed shRNAs in vitro, but interestingly, low to undetectable levels in vivo. This suggests that export was likely not limiting in the present studies. Alternatively, the striatal toxicity may be caused by the build-up of antisense RNAs and subsequent off-target silencing of unintended mRNAs. The present data on sh8.2 is also consistent with this; sh8.2 was not toxic when delivered at the same dose as sh2.4 and sh30.1. And though silencing activity was similar between the three shRNAs, levels of mature product for sh8.2 was significantly lower.

The inventors found that moving the HD2.4 and HD2.4mis sequences, both of which caused toxicity in the context of a shRNA, into a miRNA scaffold significantly reduced neurotoxicity within the striatum with no sacrifice in gene silencing efficacy. The inventors correlated this positive effect to lower steady-state levels of mature antisense RNAs processed from the artificial mi2.4 relative sh2.4. Whether this disparity in expression levels results from differences in transcription or stability between shRNAs and artificial miRNAs remains unknown. However, the latter provides a more likely explanation since sh2.4 and mi2.4 are expressed from the same mouse U6 promoter and only differ in size by approximately 100 nucleotides.

In addition to improved safety profiles, artificial miRNAs are amenable to Pol-II mediated transcription. Conversely, shRNAs have limited spacing flexibility for expressing shRNAs from Pol II based promoters. This advantage of miRNA-based systems allows for regulated and cell-specific expression of inhibitory RNAs. These versatile expression strategies advance the application of artificial miRNAs as biological tools and may further limit potential toxicity in therapeutic applications.

In some diseases, it is possible to specifically target disease-linked SNPs that exist on the mutant transcript. For HD however, no prevalent SNP has been reported. Because earlier work showed that a minimum of 50% huntingtin expression is required to offset the embryonic lethality noted in huntingtin null mice, knowing the consequences of reducing huntingtin expression in adult brain is important to moving non-allele specific RNAi forward as a HD therapy. The present data with sh8.2 and mi2.4 are encouraging, and suggests that the mammalian brain can tolerate greater than 50% reduction in HD mRNA for 4 months, the last time point studied. The long-term safety and efficacy of sh8.2 is currently being tested in a study including histochemical, biochemical and behavioral readouts in CAG140 HD mice.

In summary, the present experiments show that reducing HDh mRNA levels in adult mammalian brain is tolerated. The inventors also make the important observation that the toxicity of shRNAs following their expression in brain is alleviated by moving the inhibitory RNA sequences into an artificial miRNA scaffold. Thus, miRNA-based approaches are more suitable for achieving RNAi in brain to address basic research questions or develop disease therapies.

Materials and Methods

Expression Vectors and AAV shRNA expression cassettes were generated by PCR and cloned into pCR-Blunt-II TOPO vectors (Invitrogen™). Each candidate shRNA expression cassette consisted of a mouse U6 promoter, an shRNA that targets huntingtin sequences, mismatch control sequences containing four base-pair changes relative to the respective huntingtin shRNAs or *E. coli* β-galactosidase (shLacZ) and an RNA polymerase III termination sequence (six thymidine nucleotides). For artificial miRNAs, siRNAs sequences based on HD2.4 or HD2.4mis were embedded into an artificial miRNA scaffold comparable to human miR-30, to generate mi2.4 and mi2.4mis (general structure shown in FIG. 4A). The artificial miRNA stem-loops were cloned into a mouse U6 expression vector so that greater than 30 nucleotides (5' and 3') flank the stem-loop in the transcribed product.

AAV shuttle plasmids pAAVsh2.4-GFP, pAAVsh2.4mis-GFP, pAAVsh8.2-GFP, pAAVsh30.1-GFP, pAAVmi2.4-GFP and pAAVmi2.4mis-GFP contain the respective RNAi expression cassettes driven by the mouse U6 promoter. The AAV shuttles also contained a humanized *Renilla* GFP (hrGFP) gene under the control of the human cytomegalovirus immediate-early gene enhancer/promoter region, a chimeric human β-globin eGFP expression cassette followed by the splice donor/human immunoglobulin splice acceptor site, and a bovine growth hormone poly (A) signal. These transcriptional units are flanked at each end by AAV serotype 2 145-bp inverted terminal repeat sequences. The trans-packaging plasmids, pBSHSPR2C1, were constructed as follows: genomic DNA was extracted from AAV1 (American Type Culture Collection) and the cap coding sequence was amplified by PCR using Pfx polymerase (Invitrogen™). The AAV2 cap gene was excised from the AAV2 helper plasmid pBSH-SPRC2.3 and replaced with the amplified AAV1 cap sequence using a Swa I restriction site in the rep/cap intergenic junction and a BsrG I site engineered just upstream of the AAV2 poly(A) signal. The resulting trans-packaging construct, pBSHSPR2C$_1$, contains the AAV2 rep gene under the control of a minimal eukaryotic promoter, and the AAV1 cap ORF positioned between the AAV2 rep/cap intergenic junction and the AAV2 poly(A) signal. The plasmid pAd Helper 4.1 expresses the E2a, E4-orf6 and VA genes of adenovirus type 5 (Ad5) for AAV amplification.

Recombinant AAV vectors were produced by a standard calcium phosphate transfection method in HEK 293 cells, using the Ad helper, trans-packaging and AAV shuttle plasmids. Vector titers were determined by real-time PCR and were between 5 and $20 \times 10^{12}$ DNase-resistant particles (DRP)/mL. Vector infectivity was assessed in a TCID50 assay using the HeLa-based B50 cell line.

Animals

All animal protocols were approved by the ACUCA at the University of Iowa. CAG140 heterozygous knock-in mice and wildtype littermates were bred and maintained in the animal vivarium at the University of Iowa. Mice were genotyped and repeat length identified by separate PCR reactions using primers flanking the CAG repeat. Mice were housed in groups of either two or three per cage and in a controlled temperature environment on a 12 hour light/dark cycle. Food and water were provided ad libitum.

AAV Injections

CAG140 knock-in or wildtype mice were injected with AAVshRNAs or AAV-miRNAs (at the indicated titer) at 5 wk of age and sacrificed at 4 months post-injection. Procedures were as follows: in the initial study, 5 μl injections of either AAVsh2.4GFP, AAV30.1sh-GFP, AAVsh8.2-GFP or AAV-GFP were made bilaterally into striata (coordinates: 0.86 mm rostral to bregma, ±1.8 mm lateral to midline, 3.5 mm ventral to the skull surface). For the miRNA/shRNA comparison study, 5 μl injections of vector were injected unilaterally. Injection rates for all studies were 0.2 μl/min. Mice used in histological analyses were anesthetized with a ketamine/xylazine mix and transcardially perfused with 20 ml of 0.9% cold saline, followed by 20 ml of 4% paraformaldehyde in 0.1M PO$_4$ buffer. Brains were removed, post-fixed overnight, and 40-μm thick sections collected. Mice used for molecular analyses were perfused with 20 ml of 0.9% cold saline, brain removed and blocked into 1 mm thick coronal slices. Tissue punches were taken using a tissue corer (1.4 mm in diameter). All tissue punches were flash frozen in liquid nitrogen and stored at −80° C. until used.

Molecular Studies

For in vitro shRNA screening, shRNA expression plasmids were transfected (Lipofectamine 2000, Invitrogen™) into human HEK 293 cells or mouse C2C12 cells, which naturally express full-length human or mouse huntingtin, respectively. Huntingtin levels were assessed by protein dot blot (anti-huntingtin primary antibody MAB2166, 1:5000; Chemicon) or western blot (protein loading control, anti-β Catenin, 1:4, 000, AbCam). Knock down was also assessed by QPCR using a human huntingtin-specific TaqMan® primer/probe set with normalization to a human GAPDH primer/probe set. This QPCR strategy was also used to evaluate HD knockdown mediated by sh2.4 and mi2.4 in FIG. 40B.

For in vivo QPCR analyses, tissue was dissected from GFP-positive striatum and relative gene expression was assessed using TaqMan® primer/probe sets for mouse HDh, CD11b, and beta-actin. All values were quantified using the $\Delta\Delta C_T$ method (normalizing to beta-actin) and calibrated to either AAV-GFP injected striata (screening study) or uninjected striata (miRNA-shRNA comparison study).

For northern blot analyses, tissue was dissected from GFP-positive striatum. RNA was harvested by TRIzol® reagent (Invitrogen™) and RNA (1 to 5 μg and 15 μg for in vivo and in vitro studies, respectively) was resolved on 15% polyacrylamide/urea gels, and RNA was visualized by ethidium bromide staining and UV exposure to assess loading and RNA quality. Samples were then transferred to Hybond™-N+/XL membranes (Amersham Pharmacia) and UV cross-linked. Blots were probed with $^{32}$P-labeled oligonucleotides at 30-36° C. overnight, washed in 2×SSC at 30-36° C., and exposed to film.

For in vivo western blot analysis, tissue was dissected from GFP-positive striatum, lysed in 150 μl of lysis buffer and protein level quantified with the DC protein assay (Bio-Rad). 10 μg total protein was separated on an 8% SDS-polyacrylamide gel before transferring to a 0.45 um PVDF membrane. The membrane was blocked with 2% milk in PBS-Tween 20 (0.05%) and incubated with either an anti-huntingtin antibody (1:5000, Chemicon) or an anti-β-actin antibody (1:10, 000, Sigma) followed by a conjugated goat anti-mouse secondary antibody (1:10,000, Jackson ImmunoResearch) and ECL-Plus substrate (Amersham Biosciences) and then exposed to film.

Immunohistochemical Analyses

Forty-micron thick, free-floating coronal brain sections were processed for immunohistochemical visualization of striatal neurons (DARPP-32, 1:100, Cell Signaling Technology) and microglia (Iba1, 1:1000, WAKO) using the biotin-labeled antibody procedure. Primary antibody incubations were for 24 hours at room temperature. Sections were incubated in goat anti-rabbit biotinylated IgG secondary antibodies (1:200, Vector Laboratories, 1 h at room temperature). In all staining procedures, deletion of the primary antibody served as a control. Sections were mounted onto Superfrost™ Plus slides and coverslipped with Gelmount (Biomeda). Images were captured using an Olympus BX60 light microscope and DP70 digital camera, along with Olympus DP Controller software.

Statistical Analyses

All statistical analyses were performed using Sigma Stat statistical software. QPCR analyses for huntingtin and CD11b expression were performed using a one-way analysis of variance (ANOVA), as was northern blot densitometry analysis. Upon a significant effect, Bonferroni post-hoc analyses were performed to assess for significant differences between individual groups. Western blot densitometry analysis was performed using a two-tailed Student's t-test. In all cases, P<0.05 was considered significant.

Figure Preparation

All photographs were formatted with Adobe® Photoshop® software, all graphs were made with Prism Graph software and all figures were constructed with Adobe® Illustrator software.

EXAMPLE 7

RNAi-Mediated Silencing of Genes

The inventors have previously shown that genes can be silenced in an allele-specific manner. They have also demonstrated that viral-mediated delivery of siRNA can specifically reduce expression of targeted genes in various cell types, both in vitro and in vivo. This strategy was then applied to reduce expression of a neurotoxic polyglutamine disease protein. The ability of viral vectors to transduce cells efficiently in vivo, coupled with the efficacy of virally expressed siRNA shown here, extends the application of siRNA to viral-based therapies and in vivo targeting experiments that aim to define the function of specific genes.

Huntington's disease (HD) is one of several dominant neurodegenerative diseases that result from a similar toxic gain of function mutation in the disease protein: expansion of a polyglutamine (polyQ)-encoding tract. It is well established that for HD and other polyglutamine diseases, the length of the expansion correlates inversely with age of disease onset. Animal models for HD have provided important clues as to how mutant huntingtin (htt) induces pathogenesis. Currently, no neuroprotective treatment exists for HD. RNA interference has emerged as a leading candidate approach to reduce expression of disease genes by targeting the encoding mRNA for degradation.

Although the effect of partial reduction of wildtype htt in adult neurons is unknown, it is advantageous to target only mutant htt for degradation, if possible. Disease allele-specific RNAi are designed using approaches that led to allele specific silencing for other neurogenetic disease models. This allows directed silencing of the mutant, disease-causing expanded allele, leaving the normal allele intact.

Constitutive expression of shRNA can prevent the neuropathological and behavioral phenotypes in a mouse model of Spinocerebellar Ataxia type I, a related polyQ disease. However, the constitutive expression of shRNA may not be necessary, particularly for pathologies that take many years to develop but may be cleared in a few weeks or months. For this reason, and to reduce long-term effects that may arise if nonspecific silencing or activation of interferon responses is noted, controlled expression may be very important. In order to regulate RNAi for disease application, doxycycline-responsive vectors have been developed for controlled silencing in vitro.

Most eukaryotes encode a substantial number of small noncoding RNAs termed micro RNAs (miRNAs). mir-30 is a 22-nucleotide human miRNA that can be naturally processed from a longer transcript bearing the proposed miR-30 stem-loop precursor. mir-30 can translationally inhibit an mRNA-bearing artificial target sites. The mir-30 precursor stem can be substituted with a heterologous stem, which can be processed to yield novel miRNAs and can block the expression of endogenous mRNAs.

Two strategies are possible to target a particular sequence, such as the gene involved in Huntington's Disease (FIGS. 42A and 42B). One can develop non-allele specific RNAi molecules, and candidates based on 8.2 inhibitory RNAs have been developed. Alternatively, one can develop allele-specific RNAi molecules. The inventors have worked to develop RNAi molecules that target several key single nucleotide polymorphisms (SNPs). These RNAi molecules, however, may be limited to the treatment of specific families/patients.

Another approach, which is the approach used in the present invention, the inventors targeted the expansion region. This approach has the advantage of being able to treat entire HD populations, and not just those with specific SNPs. These RNAi molecules are different because instead of targeting a SNP for allele specificity, these sequences take advantage of structural integrity at the sites flanking the expansion region. The siRNA data shows that they are effective. The present inventors have also moved them into miRNA expression vectors, which were also effective.

The inventors have generated and tested the following RNAi molecules:

| siRNA | Sequence | |
|---|---|---|
| HDAS 07 | AUGAAGGCCUUCGAGUCCCUC | (SEQ ID NO: 215) |
| HDAS 18 | GGCGACCCUGGAAAAGCUGAU | (SEQ ID NO: 216) |
| HDAS 19 | UGGCGACCCUGGAAAAGCUGA | (SEQ ID NO: 217) |
| HDAS 20 | AUGGCGACCCUGGAAAAGCUG | (SEQ ID NO: 218) |

Sequence miHD7A1
(SEQ ID NO: 219)
AAAACUCGAGUGAGCGCUGAAGGCCUUCGAGUCCCUCA
*CCGUAAAGCCAC AGAUGGG*UGAGGGACUCGAAGGCCUUCAU
CGCCUACUAGUAAAA Sequence miHD7A2
(SEQ ID NO: 220)
AAAACUCGAGUGAGCGCUGAAGGCCUUCGAGUCUUUUA
*CCGUAAAGCCAC AGAUGGG*UGAGGGACUCGAAGGCCUUCAU
CGCCUACUAGUAAAA Sequence miHD7B1
(SEQ ID NO: 221)
AAAACUCGAGUGAGCGCAUGAAGGCCUUCGAGUCCCU
*CCGUAAAGCCAC AGAUGGG*GAGGGACUCGAAGGCCUUCAUC
CGCCUACUAGUAAAA Sequence miHD7B2
(SEQ ID NO: 222)
AAAACUCGAGUGAGCGCAUGAAGGCCUUCGAGUCUUUU
*CCGUAAAGCCAC AGAUGGG*GAGGGACUCGAAGGCCUUCAUC
CGCCUACUAGUAAAA The different fonts show the various parts of the miRNA. In sequential order, the stem sequence of the miRNA is shown in bold, then the sense strand in regular type, then the loop sequence in bold italics, then the anti-sense strand in regular type, and last, part of stem sequence in bold.

Figure 43A:
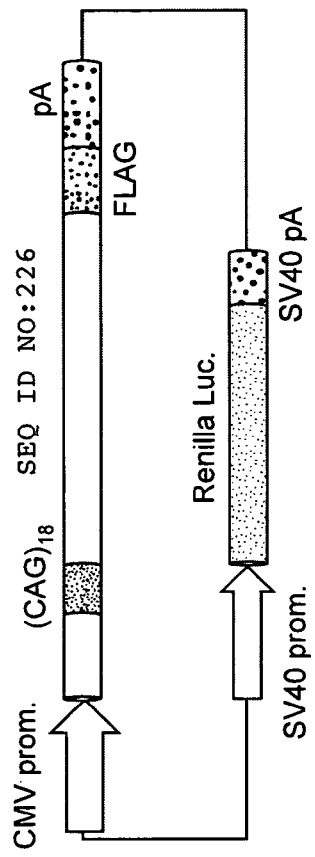
FIGS. 43A-43B. Constructs to assess allele-specific silencing. Two plasmids were generated expressing full-length wild type (FIG. 43A, pCMV-FLHtt 18Q-Flag) or mutant huntingtin (FIG. 43B, pCMV-FLHtt 83Q-V5).
Figure 43B:
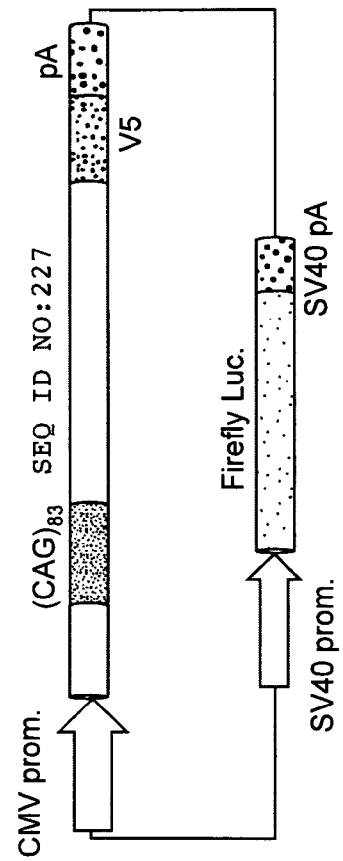

The inventors generated constructs to assess allele-specific silencing of Htt (FIGS. 43A and 43B). Two plasmids were generated expressing full-length wild type (FIG. 43A, pCMV-FLHtt 18Q-Flag) or mutant huntingtin (FIG. 43B, pCMV-FLHtt 83Q-V5). Wild type and mutant full-length huntingtin are expressed under the control of the CMV promoter and each cDNA have distinct epitope tags to differentiate its expression by western blot. To normalize transfection efficiencies either *renilla* (WT htt) or firefly (mutant htt) luciferase were included on the same plasmid. This design allowed assessment of allele specificity in the same cell after co-transfection.

Western blot and Q-PCR results indicate that the candidate siRNAs were allele-specific in targeting mutant Htt, but not wild type Htt (FIGS. 44A-44C). HEK293 cells were co-transfected with plasmids expressing wild type and mutant huntingtin and with different siRNA sequence. Total RNA and protein lysates were obtained 24 hours after transfection. After screening by Q-PCR and western blot, some of the siRNA design sequences were observed to preferentially silence the mutant allele. FIG. 44A shows wild type Htt and FIG. 44B shows mutant Htt. As seen in FIG. 44C, siRNA sequence number 7 (S7) reduced mutant htt by 40% and the wild type huntingtin by 6%.

The inventors found that formulated LNP siRNAs were distributed broadly following intrastriatal infusion, that formulated LNP siRNA reduced Htt in adult mouse brain at biologically relevant dose, and siRNAs targeting sequences targeting the expansion provided for allele specific silencing.

Figure 45:
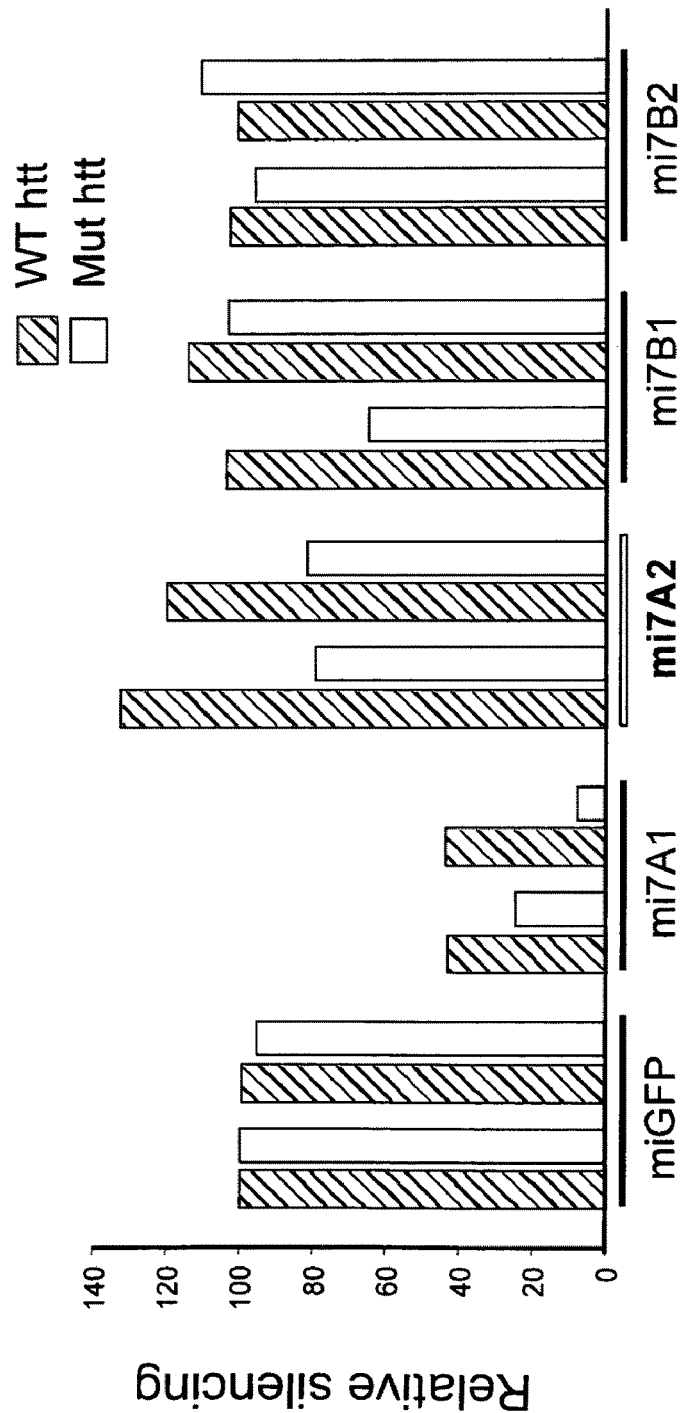
FIG. 45 shows the results of miRNA shuttles for allele-specific silencing of htt. Data represents the densitometry analysis of wild type and mutant Htt expression for different protein lysates.

The inventors also found that miRNA shuttles for allele specific silencing of htt could effectively be used (FIG. 45). miRNA shuttles based on the siRNA sequence 7 (S7) were generated. To assess silence specificity, HEK293 cells were co-transfected with wild type and mutant huntingtin plasmids and mi7A1, mi7A2, mi7B1, mi7B2 or miGFP as a control. Cells were harvested 24 hours after transfection and wild type and mutant Htt silencing was determined by western blot. Mi7A 1 and mi7A2 had the most preferential silencing profile, the latter the most beneficial.

Figure 46:
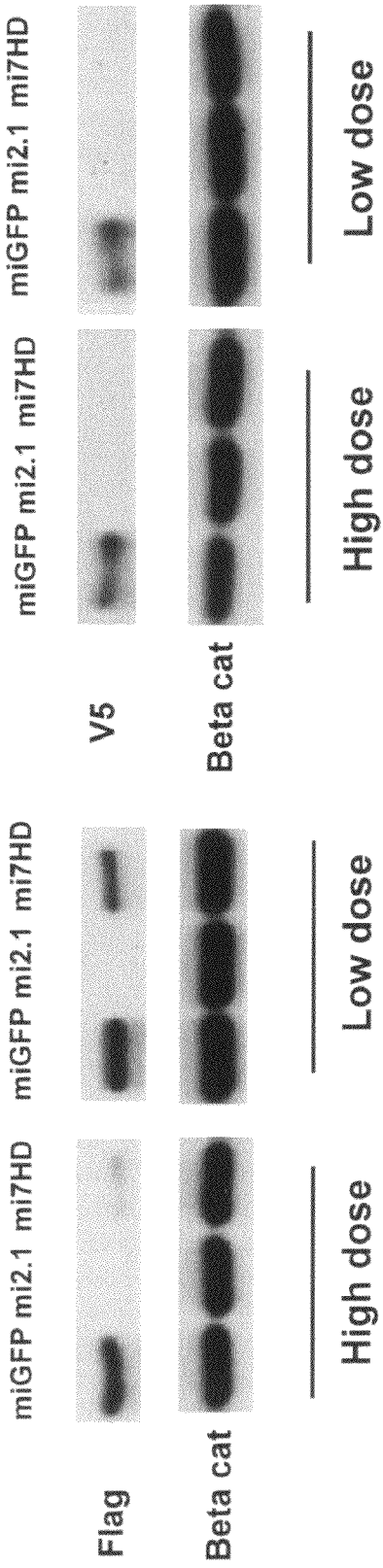
FIGS. 46A-46B. Dose response of mi7A1 sequence.

Sequence mi7A1 silences very efficiently either wild type or mutant huntingtin. This is possibly due to an excess of mi7A1 production. The specificity of silencing of mi7A1 at high and low doses was compared. HEK293 cells were transfected with two different amounts of mi7A 1 and protein lysates were obtained 24 hours after transfection. Silencing of both wild type and mutant huntingtin was determined by western blot with specific antibodies against the epitope tags (FIGS. 46A and 46B). Data shows that preferential silencing for the mutant huntingtin is achieved when mi7A1 is transfected at a low dose. FIG. 46A shows normal Htt, and FIG. 46B shows mutant Htt.

Figure 47:
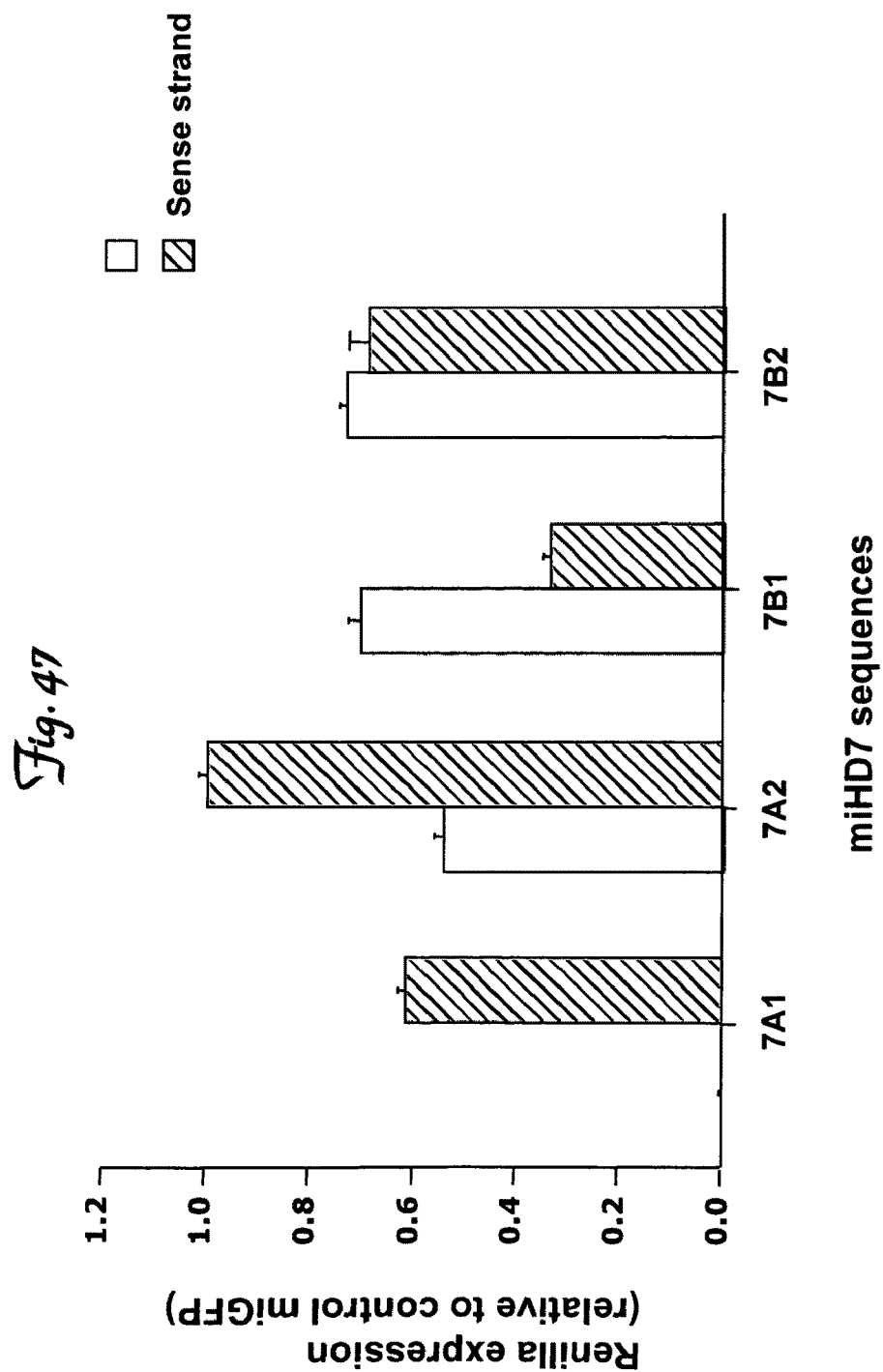
FIG. 47. Strand biasing of miR shuttles. Data represents relative luciferase expression of the reporter constructs for each specific strand after mi7 shuttle transfection. All data is compared to cells transfected with each reporter constructs and a miRNA control (miGFP).

The inventors also evaluated the strand biasing of miR shuttles (FIG. 47). Different mutations were introduced to the 3' end of the sense strand of the mi7 sequences (mi7A2 and mi7B2) to promote antisense strand loading into the RISC. To determine which strand was preferentially loaded several luciferase reporter constructs based on psicheck2 vector were designed. HEK293 cells were cotransfected with both mi7 shuttle and a reporter construct for each strand and 24 hours later cell extracts were obtained. Sequences 7A1 and 7A2 showed exceptional strand biasing.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nucleic acid encoding an artificial primary miRNA transcript (pri-miRNA) consisting of, in order of position, a 5'-flanking region, a first siRNA region, a loop region, a second siRNA region, and a 3'-flanking region, wherein the 5'-flanking region comprises:
   (a) a 5'-joining sequence contiguously linked to the first siRNA region, wherein the 5' joining sequence consists of 5-7 nucleotides,
   (b) a 5'-bulge sequence positioned upstream from the 5'-joining sequence consisting of 1-10 nucleotides, and
   (c) a 5'-spacer sequence positioned upstream from the 5'-bulge sequence, wherein the 5'-spacer sequence is UGGUACCGUU (SEQ ID NO: 180).

2. The nucleic acid of claim 1, wherein the 5'-flanking region is contiguously linked to the first siRNA region, the loop region is positioned between the first siRNA region and the second siRNA region, and the second siRNA region is contiguously linked to the 3'-flanking region.

3. The nucleic acid of claim 1, wherein the first siRNA region is a non-guide region and the second siRNA region is a guide region.

4. The nucleic acid of claim 1, wherein the first siRNA region is a guide region and the second siRNA region is a non-guide region.

5. The nucleic acid of claim 1, wherein the 5' joining sequence consists of 6 nucleotides.

6. The nucleic acid of claim 1, wherein the 5'-joining sequence encodes GUGASSS, wherein S is either a G or C nucleotide.

7. The nucleic acid of claim 1, wherein the 5' joining sequence encodes GUGAGCG.

8. The nucleic acid of claim 1, wherein the 5'-bulge sequence comprises a cloning site.

9. The nucleic acid of claim 8, wherein cloning site encodes an XhoI site.

10. The nucleic acid of claim 1, wherein the 5'-bulge sequence encodes UAAACUCGA.

11. The nucleic acid of claim 1, wherein the 5'-flanking region further comprises a 5'-upstream sequence positioned upstream from the 5'-spacer sequence.

12. The nucleic acid of claim 11, wherein the 5'-upstream sequence is about 30-2000 nucleotides in length.

13. The nucleic acid of claim 1, wherein the 3'-flanking region comprises a 3'-joining sequence contiguously linked to the second siRNA region.

14. The nucleic acid of claim 13, wherein the 3' joining sequence consists of 5-7 nucleotides.

15. The nucleic acid of claim 13, wherein the 3'-joining sequence is at least about 85% complementary to the 5'-joining sequence.

16. The nucleic acid of claim 13, wherein the 3'-joining sequence encodes CGCYUAC, wherein Y is C or U.

17. The nucleic acid of claim 13, wherein the 3'-joining sequence encodes CGCCUAC.

18. The nucleic acid of claim 13, wherein the 3'-flanking region further comprises a 3'-bulge sequence positioned downstream from the 3'-joining sequence.

19. The nucleic acid of claim 18, wherein the 3'-bulge sequence comprises a cloning site.

20. The nucleic acid of claim 19, wherein cloning site encodes a SpeI/XbaI site or a SpeI site.

21. The nucleic acid of claim 18, wherein the 3'-bulge sequence consists of about 1-10 nucleotides.

22. The nucleic acid of claim 18, wherein 3'-bulge sequence encodes UAG.

23. The nucleic acid of claim 18, wherein the 5'-bulge sequence is complementary to the 3'-bulge sequence at only one nucleotide at each end of the bulge sequence.

24. The nucleic acid of claim 18, wherein the 3'-flanking region further comprises a 3'-spacer sequence positioned downstream from the 3'-bulge sequence.

25. The nucleic acid of claim 24, wherein the 3'-spacer sequence consists of 10-12 nucleotides.

26. The nucleic acid of claim 24, wherein the 3'-spacer sequence is AGCGGCCGCCA (SEQ ID NO: 181).

27. The nucleic acid of claim 24, wherein the 3'-spacer sequence is at least about 70% complementary to the 5'-spacer sequence.

28. The nucleic acid of claim 24, wherein the 3'-flanking region further comprises a 3'-downstream sequence positioned downstream from the 3'-spacer sequence.

29. The nucleic acid of claim 28, wherein the 5'-flanking region further comprises a 5'-upstream sequence positioned upstream from the 5'-spacer sequence, and wherein the 5'-upstream sequence is less than 20% homologous to the 3'-downstream sequence.

30. The nucleic acid of claim 28, wherein the 3'-downstream sequence is about 30-2000 nucleotides in length.

31. The nucleic acid of claim 1, wherein the loop region is from 15-19 nucleotides in length.

32. The nucleic acid of claim 31, wherein the loop region is 17 nucleotides in length.

33. The nucleic acid of claim 1, wherein the loop region encodes CCNNNNNNNNNNNNNNNGG (SEQ ID NO: 183).

34. The nucleic acid of claim 1, wherein the loop region encodes CCGUGAAGCCACAGAUGGG (SEQ ID NO: 185).

35. An RNA encoded by nucleic acid of claim 1.

36. An expression cassette comprising a promoter contiguously linked to the nucleic acid of claim 1.

37. The nucleic acid of claim 1, wherein the loop region encodes CUNNNNNNNNNNNNNNNGG or (SEQ ID NO: 182).

38. The nucleic acid of claim 1, wherein the loop region encodes CUGUGAAGCCACAGAUGGG or (SEQ ID NO: 184).

* * * * *